(12) United States Patent
Marsh et al.

(10) Patent No.: US 11,980,749 B2
(45) Date of Patent: May 14, 2024

(54) AUTOINJECTOR

(71) Applicant: medmix Switzerland AG, Haag (CH)

(72) Inventors: William Geoffrey Arthur Marsh, Stratford-upon-Avon (GB); Anthony Paul Morris, Balsall Common (GB); Matthew Meredith Jones, Warwick (GB); Aled Meredydd James, Solihull (GB)

(73) Assignee: MEDMIX SWITZERLAND AG, Haag (CH)

( * ) Notice: Subject to any disclaimer, the term of this patent is extended or adjusted under 35 U.S.C. 154(b) by 0 days.

(21) Appl. No.: 17/977,749

(22) Filed: Oct. 31, 2022

(65) Prior Publication Data

US 2023/0129080 A1   Apr. 27, 2023

Related U.S. Application Data

(63) Continuation of application No. PCT/US2022/048041, filed on Oct. 27, 2022, which
(Continued)

(30) Foreign Application Priority Data

Oct. 27, 2021 (EP) .................................. 21205085
Dec. 23, 2021 (EP) .................................. 21217555
Apr. 14, 2022 (EP) .................................. 22168393

(51) Int. Cl.
*A61M 5/32* (2006.01)

(52) U.S. Cl.
CPC .......... *A61M 5/3204* (2013.01); *A61M 5/326* (2013.01); *A61M 2005/3261* (2013.01)

(58) Field of Classification Search
CPC ........ A61M 2005/2013; A61M 5/3243; A61M 2005/3267; A61M 5/3272; A61M 5/3271; A61M 2005/3268; A61M 5/3269
See application file for complete search history.

(56) References Cited

U.S. PATENT DOCUMENTS 10,188,799 B2   1/2019   Saussaye et al.
10,376,641 B2   8/2019   Hirschel et al.
(Continued)

FOREIGN PATENT DOCUMENTS

CH   711240 A2    12/2016
EP   2753382 B1   12/2015
(Continued)

OTHER PUBLICATIONS

European Search Report dated Mar. 22, 2022 in corresponding European Application No. 21205085.0.

*Primary Examiner* — Emily L Schmidt
(74) *Attorney, Agent, or Firm* — GLOBAL IP COUNSELORS, LLP

(57) ABSTRACT

An autoinjector basically includes a housing, a pre-filled syringe, a drive chassis, and a needle guard. The pre-filled syringe is mounted in the housing. The drive chassis is configured to move a plunger in the pre-filled syringe to dispense medicament via an urging force from a drive spring. The needle guard is moveable in the housing between a storage state, a dispensing state, and a lock-out state. The needle guard is biased towards an extended position by a lock-out spring. The needle guard selectively engages the housing to establish a frontmost position of the needle guard in the storage state, and an offset position of the needle guard in the lock-out state. The offset position is axially offset from the frontmost position in the distal direction.

14 Claims, 55 Drawing Sheets

Related U.S. Application Data is a continuation of application No. 17/668,071, filed on Feb. 9, 2022.

(56) References Cited

U.S. PATENT DOCUMENTS

| | | |
|---|---|---|
| 10,589,035 B2 | 3/2020 | Mehawej et al. |
| 10,661,014 B2 | 5/2020 | Sarkinen et al. |
| 10,905,827 B2 | 2/2021 | Kramer et al. |
| RE48,593 E | 6/2021 | Hourmand et al. |
| 11,052,199 B2 | 7/2021 | Fabien et al. |
| 11,185,642 B2 | 11/2021 | Kramer et al. |
| 2005/0027255 A1 | 2/2005 | Lavi et al. |
| 2006/0229569 A1 | 10/2006 | Lavi et al. |
| 2017/0165428 A1 | 6/2017 | Säll |
| 2018/0147360 A1* | 5/2018 | Kemp ............... A61M 5/2033 |
| 2019/0046735 A1* | 2/2019 | Ingerslev ............. A61M 5/001 |
| 2019/0240407 A1 | 8/2019 | Constantineau et al. |
| 2019/0328968 A1 | 10/2019 | Giambattista |
| 2019/0374717 A1 | 12/2019 | Swanson et al. |
| 2020/0108211 A1 | 4/2020 | Jacobsen |
| 2020/0139048 A1 | 5/2020 | Buchine et al. |
| 2020/0147321 A1 | 5/2020 | Andrée et al. |
| 2020/0289753 A1 | 9/2020 | Andrée et al. |
| 2021/0030962 A1* | 2/2021 | Moeller ............. A61M 5/2033 |
| 2021/0085883 A1 | 3/2021 | Daniel |
| 2021/0093793 A1* | 4/2021 | Finkelstein ........ A61M 5/31511 |
| 2021/0106757 A1 | 4/2021 | Hemmingsen et al. |
| 2021/0113776 A1 | 4/2021 | Hopkins et al. |
| 2021/0128836 A1 | 5/2021 | Kiilerich |
| 2021/0137944 A1 | 5/2021 | Wotton et al. |
| 2021/0196894 A1 | 7/2021 | Appy et al. |
| 2021/0196896 A1 | 7/2021 | Alexandersson |
| 2021/0213210 A1 | 7/2021 | Jensen |

FOREIGN PATENT DOCUMENTS

| | | |
|---|---|---|
| EP | 2907537 B1 | 8/2017 |
| EP | 2654833 B1 | 2/2019 |
| EP | 3122400 B1 | 7/2019 |
| EP | 3129085 B1 | 7/2019 |
| EP | 2742962 B1 | 12/2019 |
| EP | 2750739 B1 | 2/2020 |
| EP | 3653241 A1 | 5/2020 |
| EP | 2624882 B1 | 4/2021 |
| EP | 3079740 B1 | 8/2021 |
| EP | 3501578 B1 | 10/2021 |
| GB | 2577549 B | 4/2020 |
| WO | 2015004051 A1 | 1/2015 |
| WO | 2018091257 A1 | 5/2018 |
| WO | 2019175665 A2 | 9/2019 |
| WO | 2020126270 A1 | 6/2020 |
| WO | 2020169842 A1 | 8/2020 |
| WO | 2021078610 A1 | 4/2021 |
| WO | 2021100039 A1 | 5/2021 |
| WO | 2021161029 A1 | 8/2021 |

\* cited by examiner

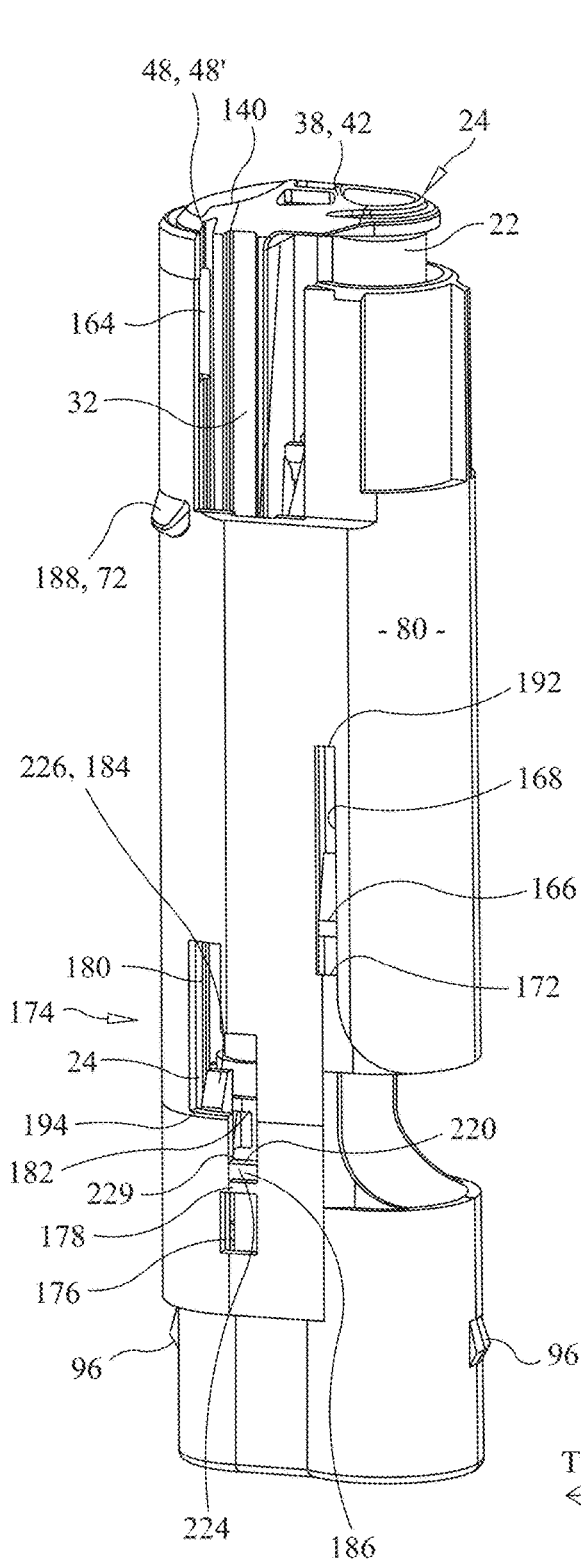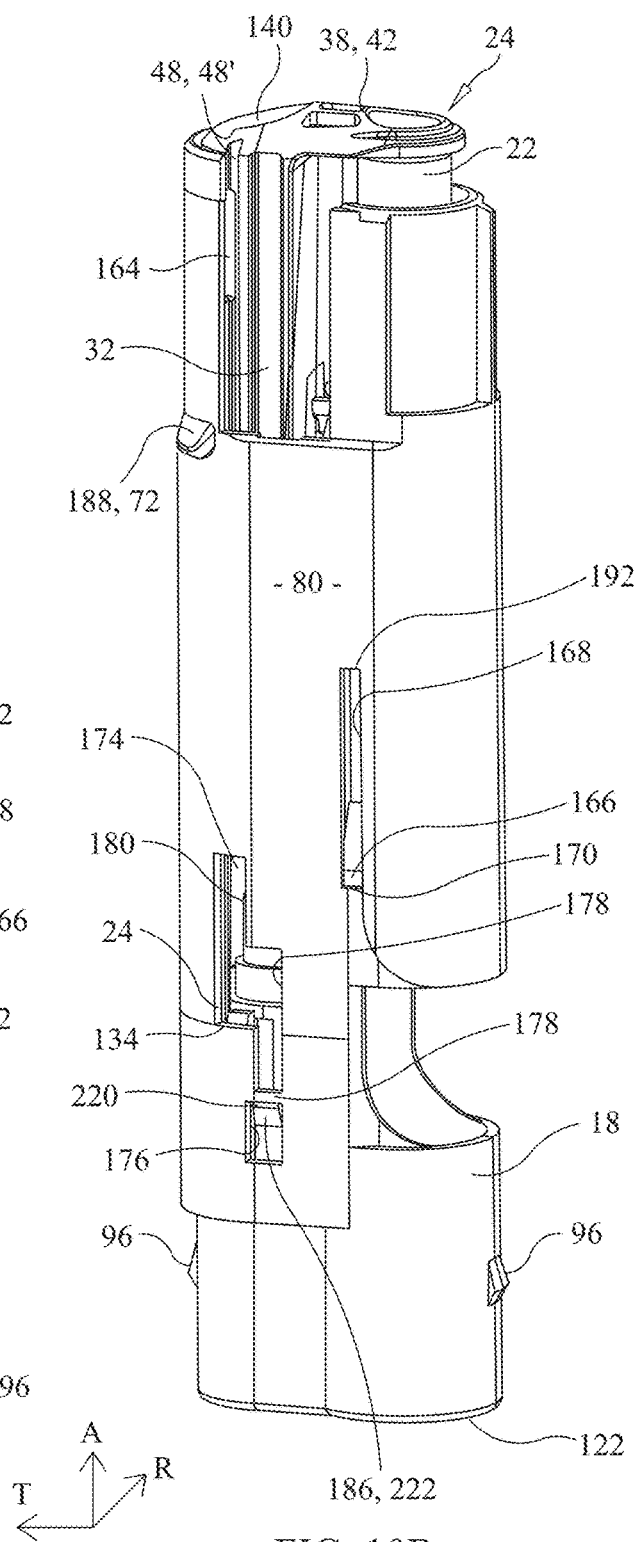
FIG. 10A
FIG. 10B

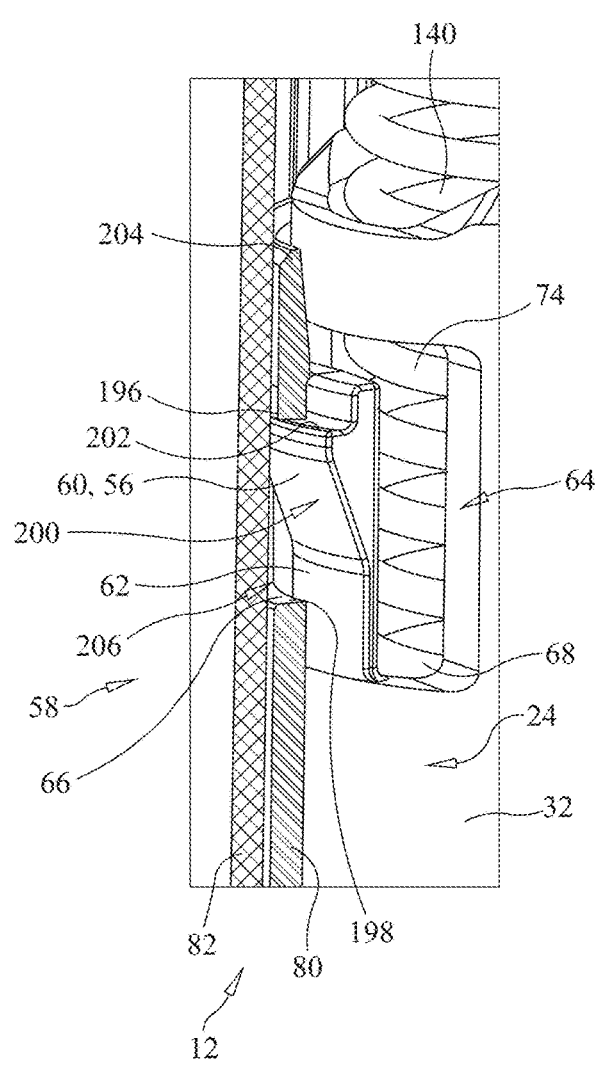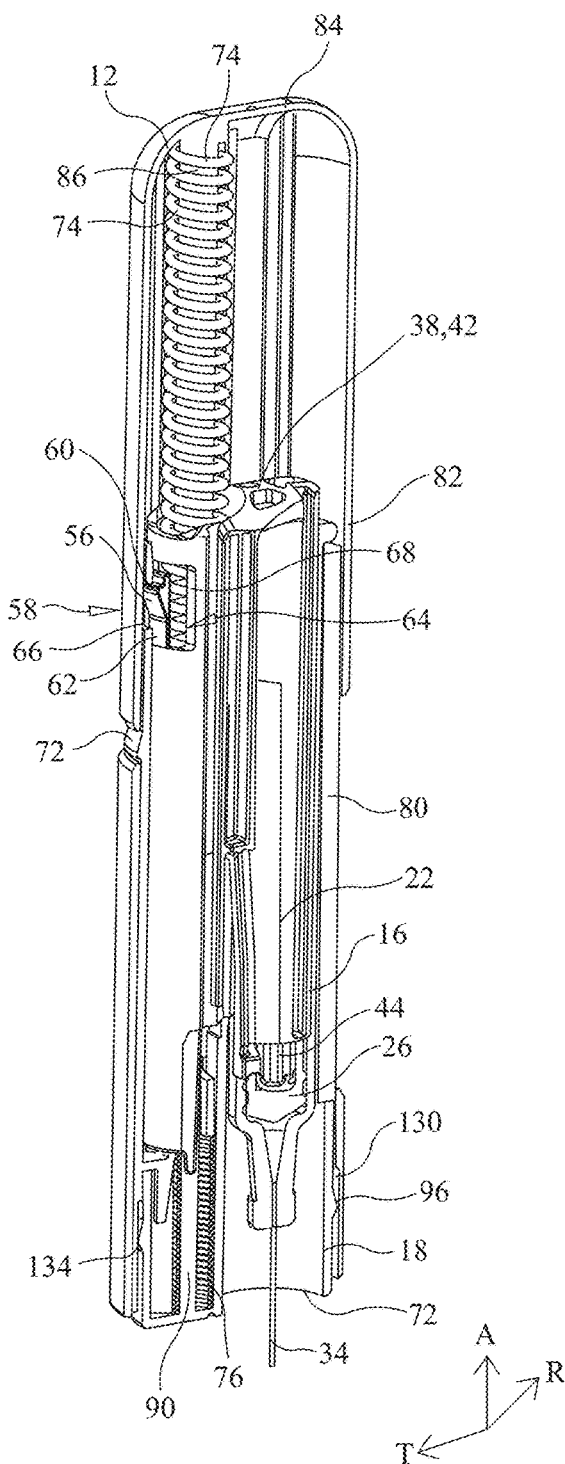
FIG. 11A
FIG. 11B

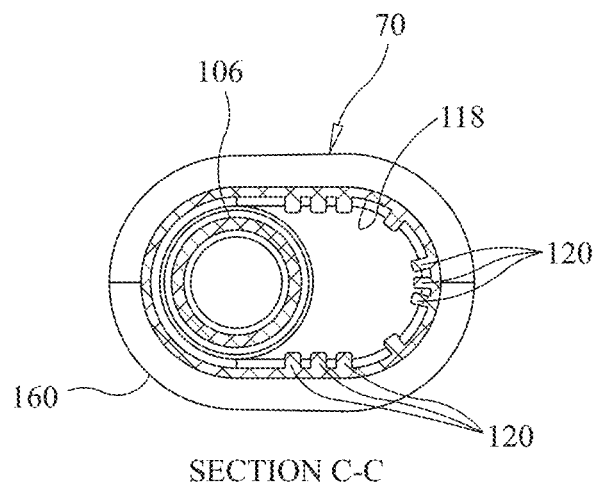
FIG. 12D
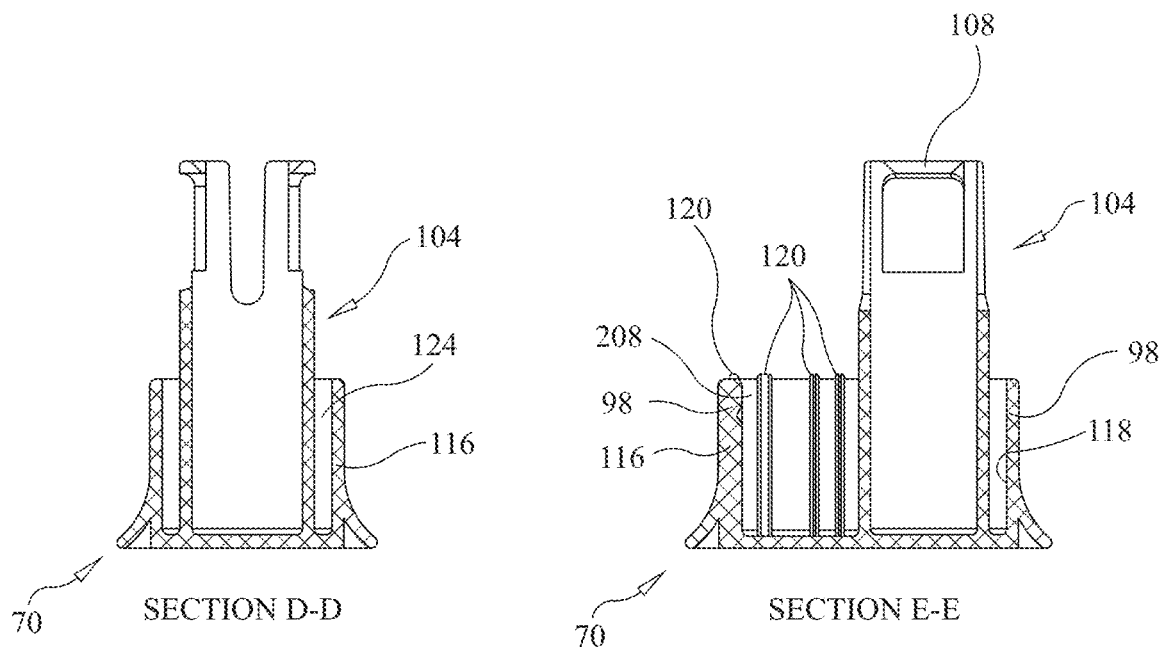
FIG. 12E
FIG. 12F

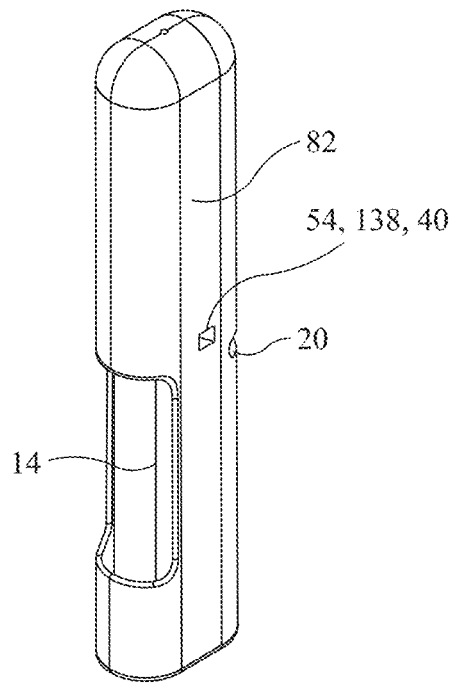
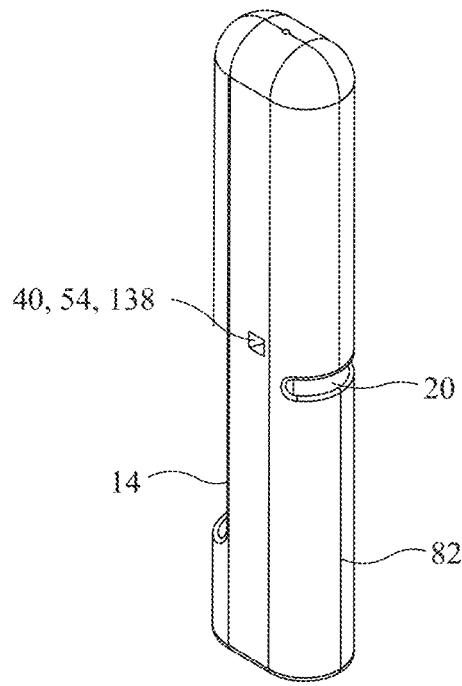
FIG. 13A  FIG. 13B
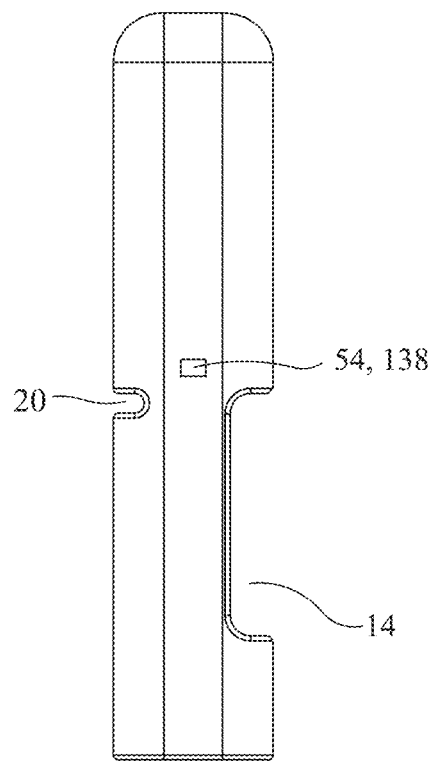
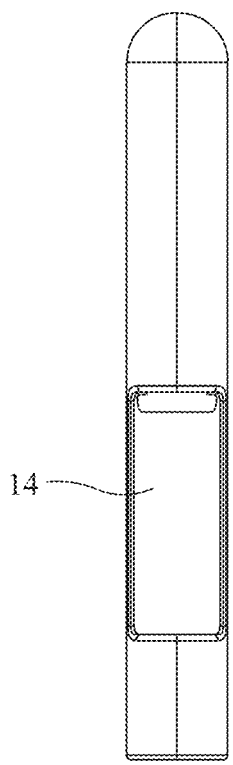
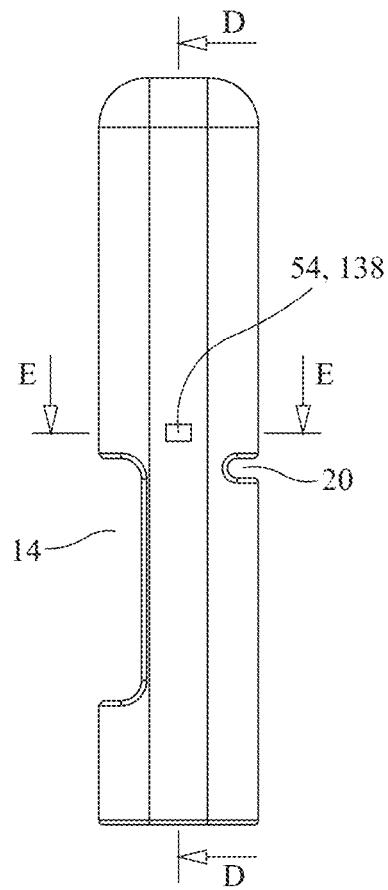
FIG. 13C  FIG. 13D  FIG. 13E

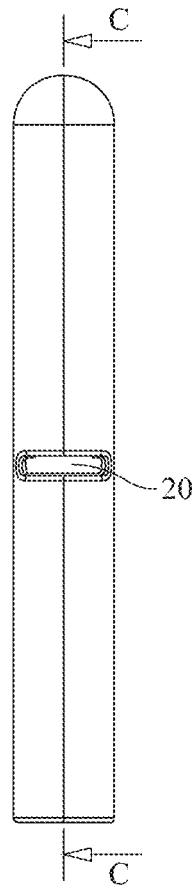
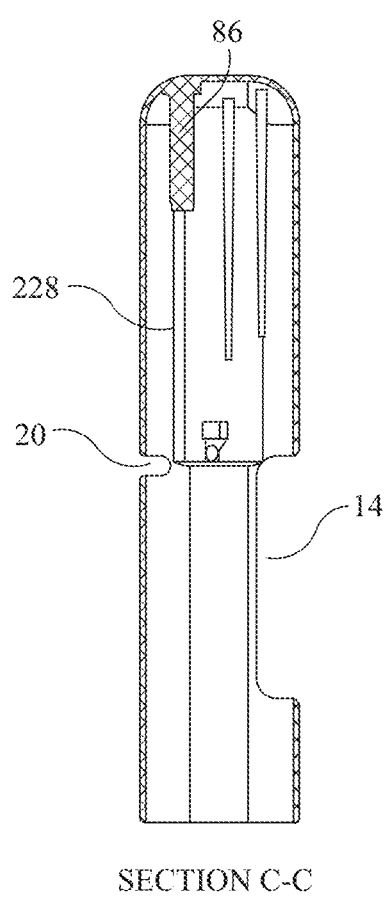
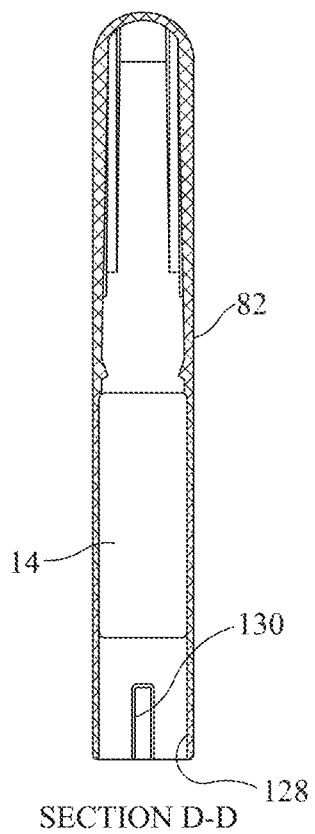
FIG. 13F  FIG. 13G  FIG. 13H
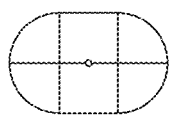
FIG. 13I
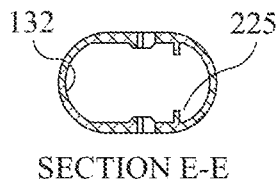
FIG. 13J

SECTION F-F

SECTION E-E

SECTION G-G

SECTION D-D

SECTION E-E

SECTION F-F

SECTION B-B

SECTION C-C

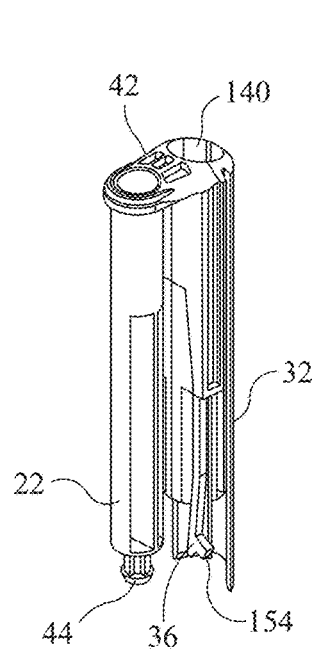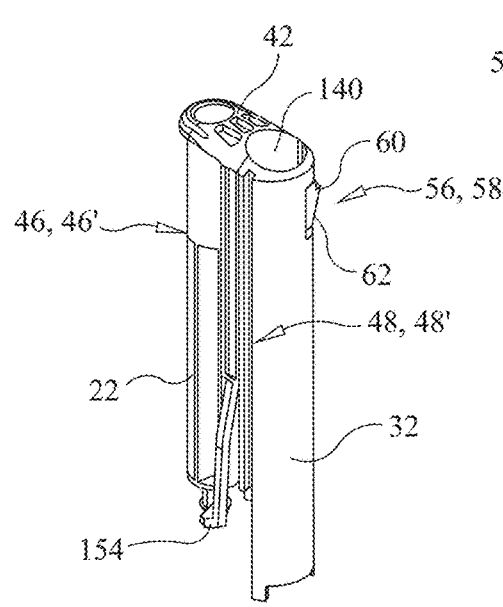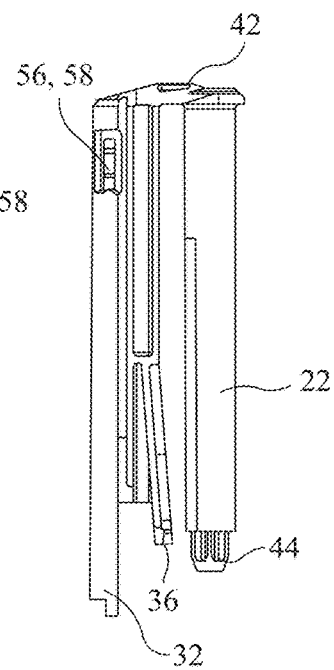
FIG. 17A  FIG. 17B  FIG. 17C
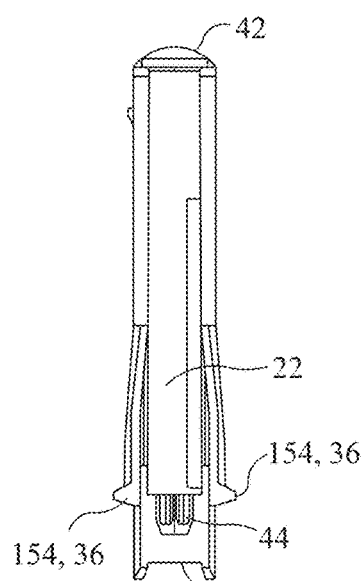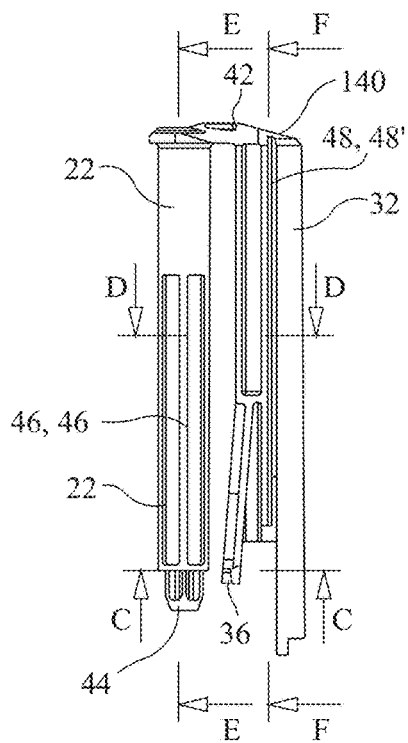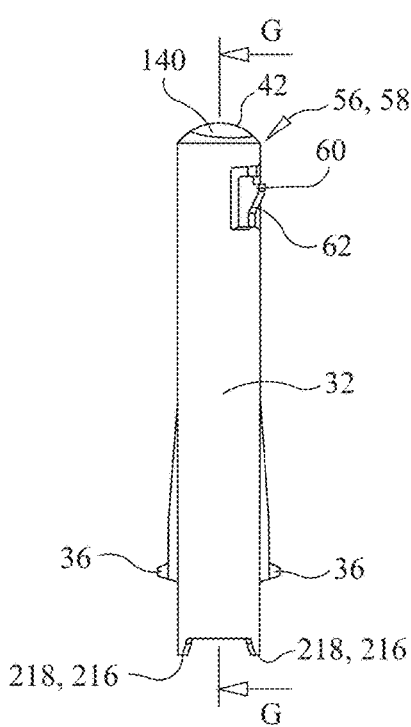
FIG. 17D  FIG. 17E  FIG. 17F

SECTION E-E

SECTION F-F

SECTION G-G

SECTION D-D

SECTION C-C

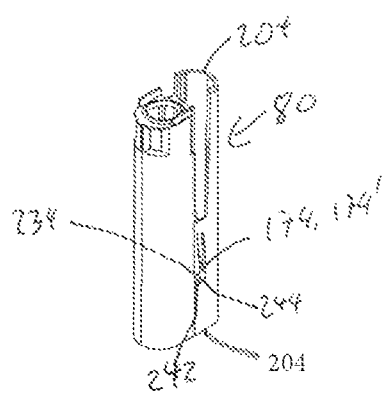
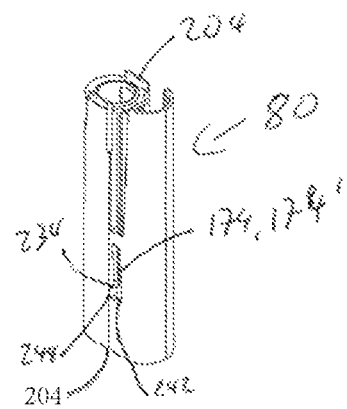
FIG. 19A　　　　　　　　　FIG. 19B
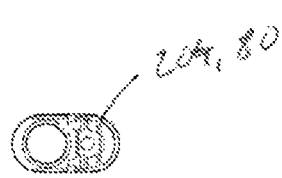
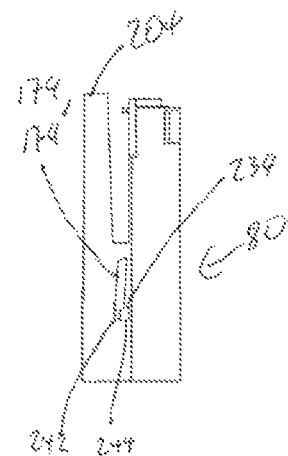
FIG. 19C　　　　　　　　　FIG. 19D
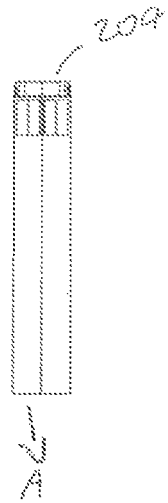
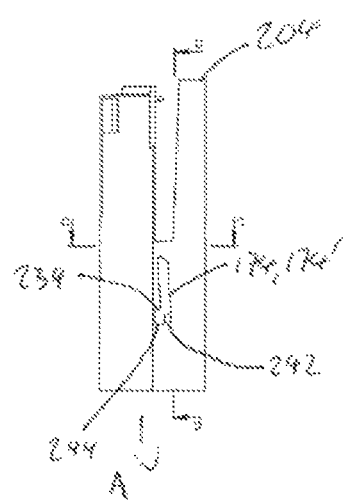
FIG. 19E　　　　　　　　　FIG. 19F

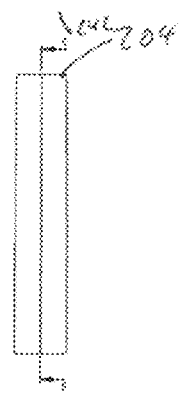
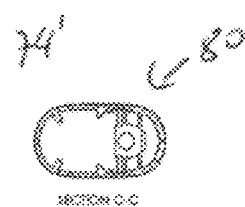
FIG. 19G  FIG. 19H
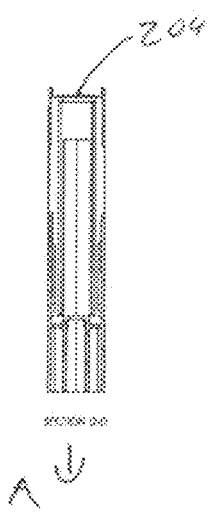
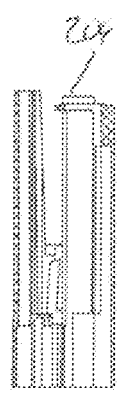
FIG. 19I  FIG. 19J

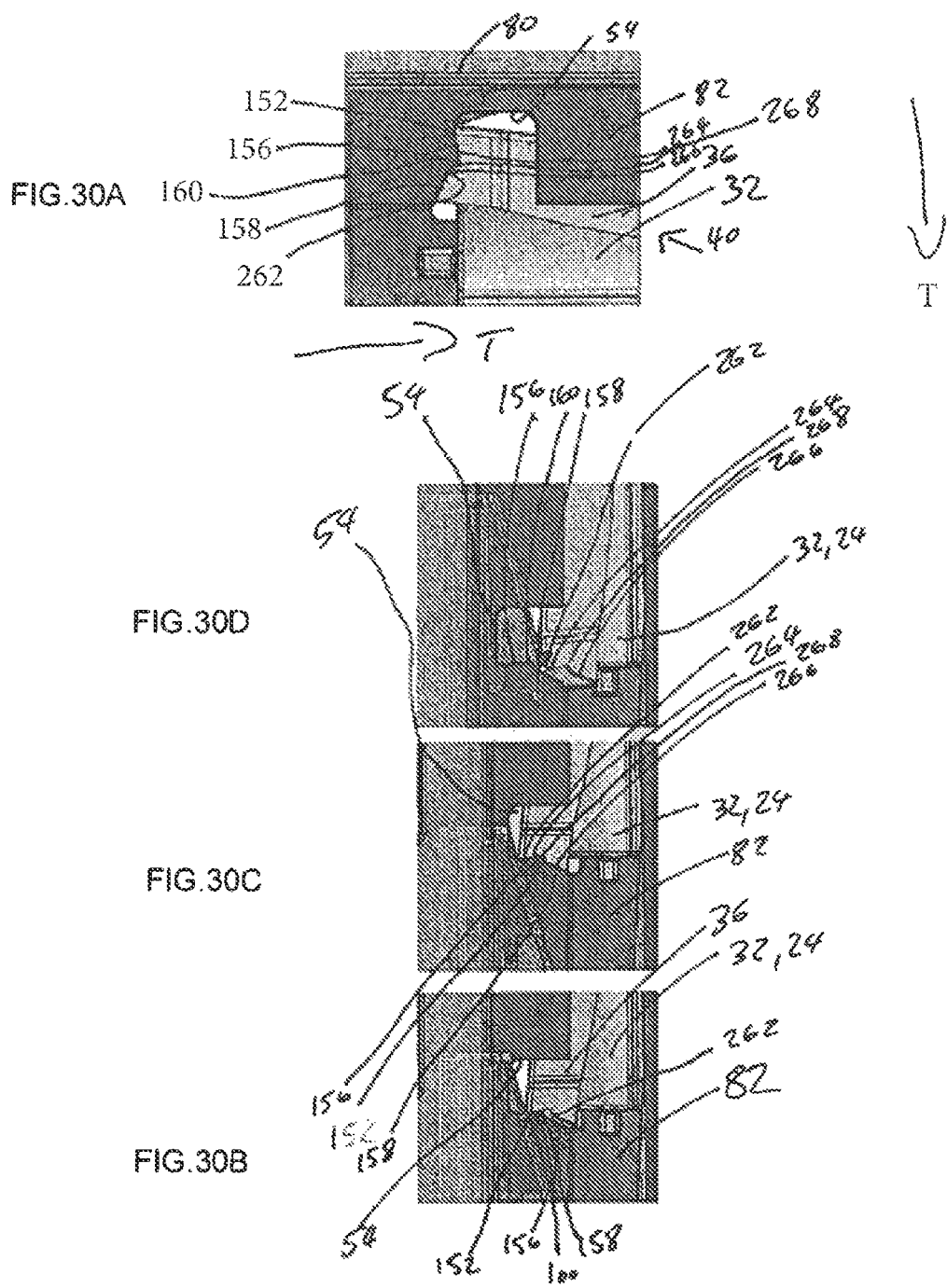

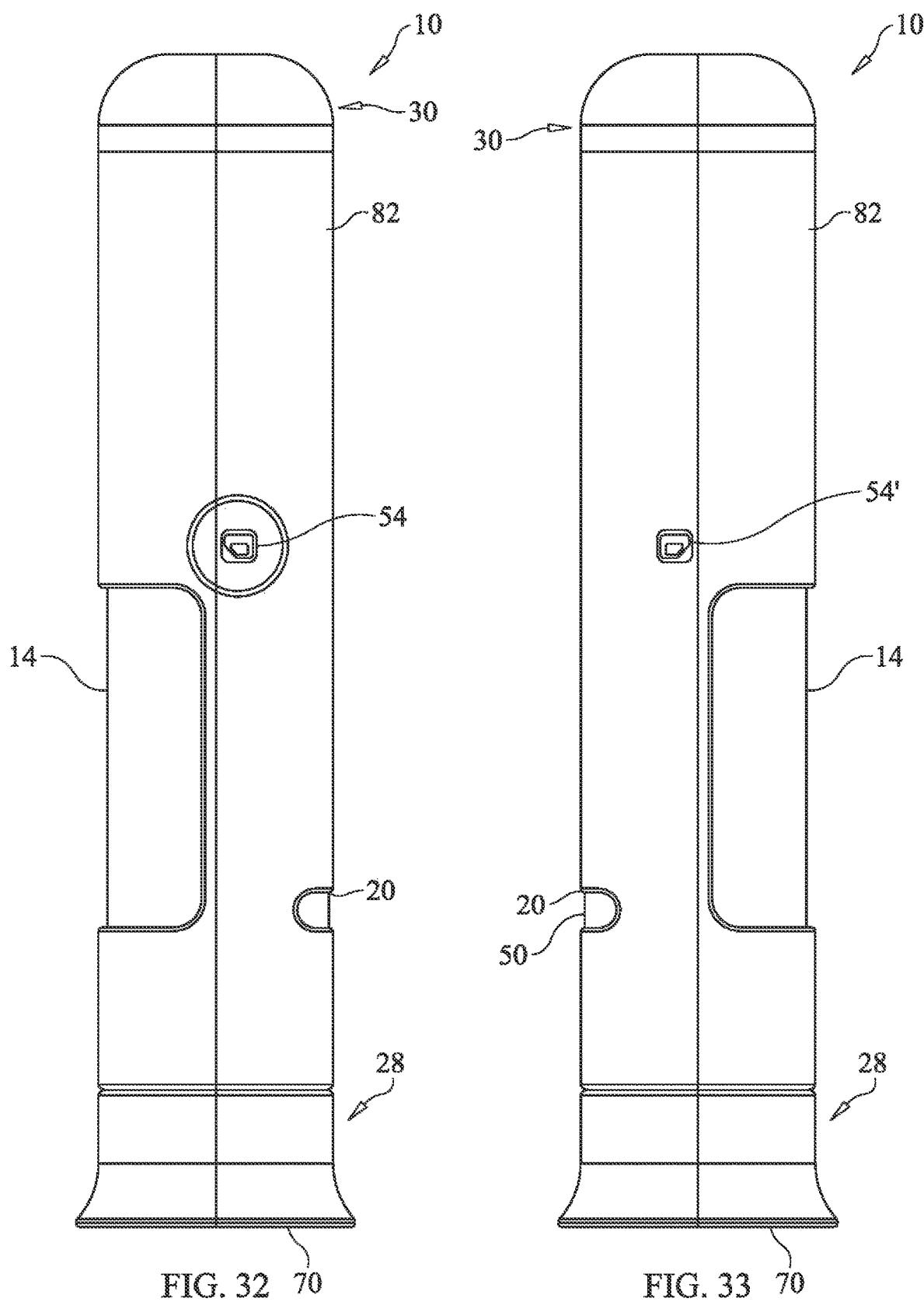

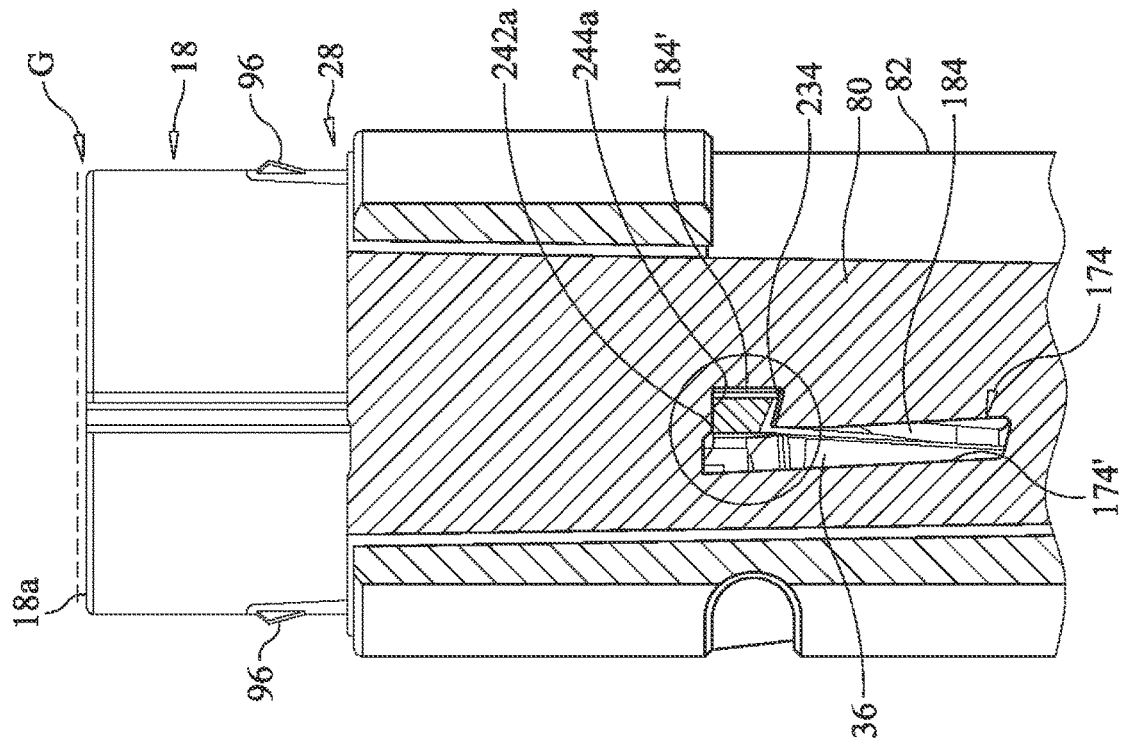
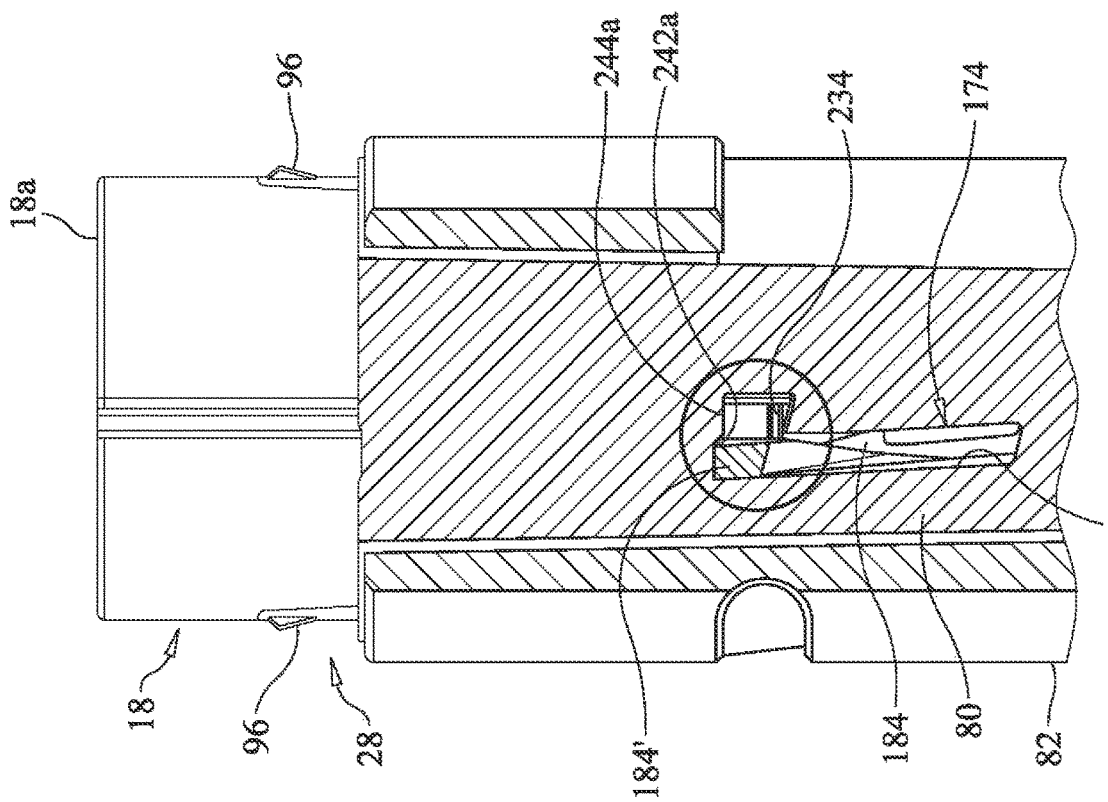

AUTOINJECTOR

CROSS-REFERENCE TO RELATED APPLICATION

This application is a continuation of International Application PCT/US22/48041, filed Oct. 27, 2022, which claims priority to U.S. patent application Ser. No. 17/668,071, filed on Feb. 9, 2022; European Patent Application No. 22168393, filed on Apr. 14, 2022; European Patent Application No. 21217555, filed on Dec. 23, 2021; and European Patent Application No. 21205085, filed on Oct. 27, 2021, the contents of which are hereby incorporated by reference in their entirety.

BACKGROUND

Technical Field

This disclosure generally relates to an autoinjector. More specifically, the present disclosure relates to an autoinjector having an axially moveable needle guard that moves between a storage state, a dispensing state and a lock-out state in which states the needle guard adopts different axial positions.

Background Information

Autoinjectors are typically disposable devices configured to dispense medicament from a pre-filled syringe. Such devices are single-use and intended for administration by a patient (i.e., self-administration) or caregiver. At point of use, the user removes a protective cap from the proximal end of the autoinjector and positions the autoinjector at the injection site (typically the skin of the thigh or belly) and presses the autoinjector axially in a proximal direction, to achieve needle insertion of a needle of the pre-filled syringe into the skin and to initiate dispensing. In some autoinjectors, an axially moveable needle guard is provided to initiate dispensing of the medicament. Examples of autoinjectors having an axially moveable needle guard to initiate dispensing of the medicament are disclosed in U.S. Pat. Nos. 10,376,641 and 11,185,642.

SUMMARY

Generally, the present disclosure is directed to various features of an autoinjector having an axially moveable needle guard. One object presented in the present disclosure is to make available an autoinjector formed from a very small number of components and a very simple process, compared to the state of the art. A further object presented in the present disclosure is to make available an as compact design as possible.

This object is satisfied by an autoinjector comprising the subject matter of claim 1.

In view of the state of the known technology and in accordance with a first aspect of the present disclosure, an autoinjector is provided that basically comprises a housing, a pre-filled syringe, a drive chassis, a drive spring, a needle guard and a lock-out spring. The pre-filled syringe is mounted in the housing and fixed relative to the housing. The drive chassis comprises a dispensing limb axially movable in the housing to move a plunger in the pre-filled syringe to dispense the medicament via a needle of the pre-filled syringe. The drive spring is arranged within the housing, and configured to drive a plunger support of the drive chassis into the pre-filled syringe. The needle guard is axially moveable in the housing for movement between a storage state surrounding a needle of the pre-filled syringe, a dispensing state exposing the needle, and a lock-out state surrounding the needle. The lock-out spring is arranged between the needle guard and the housing. The needle guard is configured to compress the lock-out spring on moving from the storage state to the dispensing state. The needle guard is configured to be moved by a relaxation of the lock-out spring from the dispensing state to the lock-out state. The needle guard includes at least one arm having an abutment surface that is configured to engage a first stop surface of the housing to establish a frontmost position of the needle guard with respect to the housing in the storage state, and configured to engage a second stop surface of the housing to establish an offset position of the needle guard with respect to the housing in the lock-out state, the offset position is axially offset with respect to the housing from the frontmost position of the needle guard in a more distal direction.

With the autoinjector according to the first aspect, it is possible to eliminate the risk that the needle guard will be locked with the housing before use.

Also, other objects, features, aspects and advantages of the disclosed autoinjector will become apparent to those skilled in the art from the following detailed description, which, taken in conjunction with the annexed drawings, discloses preferred embodiments of the autoinjector.

BRIEF DESCRIPTION OF THE DRAWINGS

Referring now to the attached drawings which form a part of this original disclosure:

FIG. 10A is a perspective view of the position of a needle guard of the autoinjector relative to the housing in the storage state;

FIG. 10B is a perspective view of the position of the needle guard of the autoinjector relative to the housing in the lock-out state;

FIG. 11A is a part sectional view of an audible feedback member of the autoinjector in the dispensing state at end of dose;

FIG. 11B is an enlarged view of the audible feedback member of the autoinjector in the dispensing state at the end of dose;

FIGS. 12A to 12F are various views of an example of a cap of an autoinjector;

FIGS. 13A to 13J are various views of an example of an outer body of an autoinjector;

FIGS. 17A to 17L are various views of an example of a drive chassis of an autoinjector;

FIGS. 19A to 19J are various views of the inner body of FIG. 18;

FIGS. 30A to 30I are views of the autoinjector of FIG. 21 following activation of the autoinjector during the dispensing state;

FIG. 32 is a side elevational view of an autoinjector in a storage state in accordance with another embodiment;

FIG. 33 is an opposite side elevational view of the autoinjector of FIG. 32 in the storage state;

FIG. 42 is an enlargement of the dispensing end portion of the autoinjector of FIGS. 32 to 41 in the storage state;

FIG. 43 is an enlargement of the dispensing end portion of the autoinjector of FIGS. 32 to 41 in the lock-out state;

DETAILED DESCRIPTION OF EMBODIMENTS

Figure 1A:
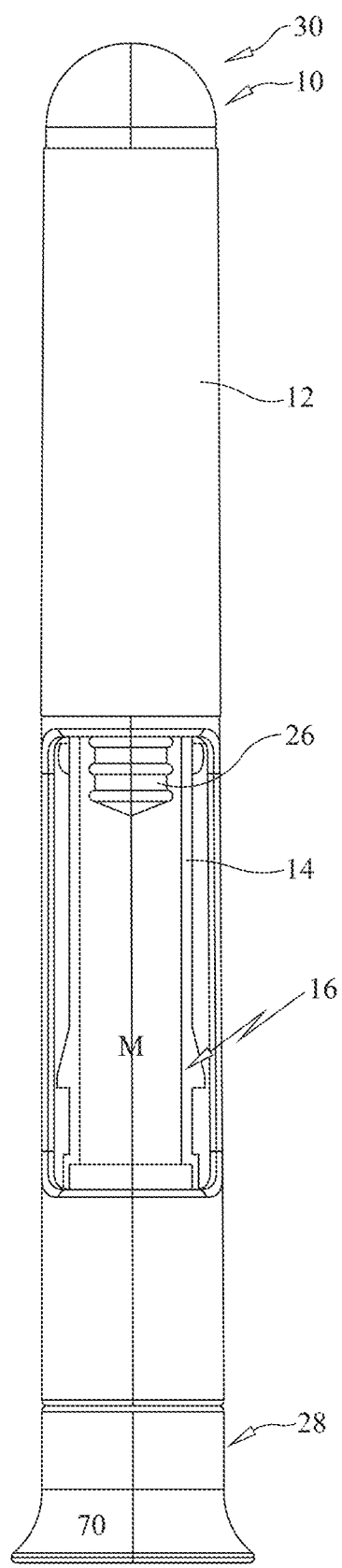
FIG. 1A is a side elevational view of an autoinjector in a storage state.

References made in the following regarding directions are made in the context of the drawing and can naturally vary if the viewing position is changed. Moreover, similar parts or parts having similar functions will be referred to in the following using the same feature and/or reference numeral.

Figure 1B:
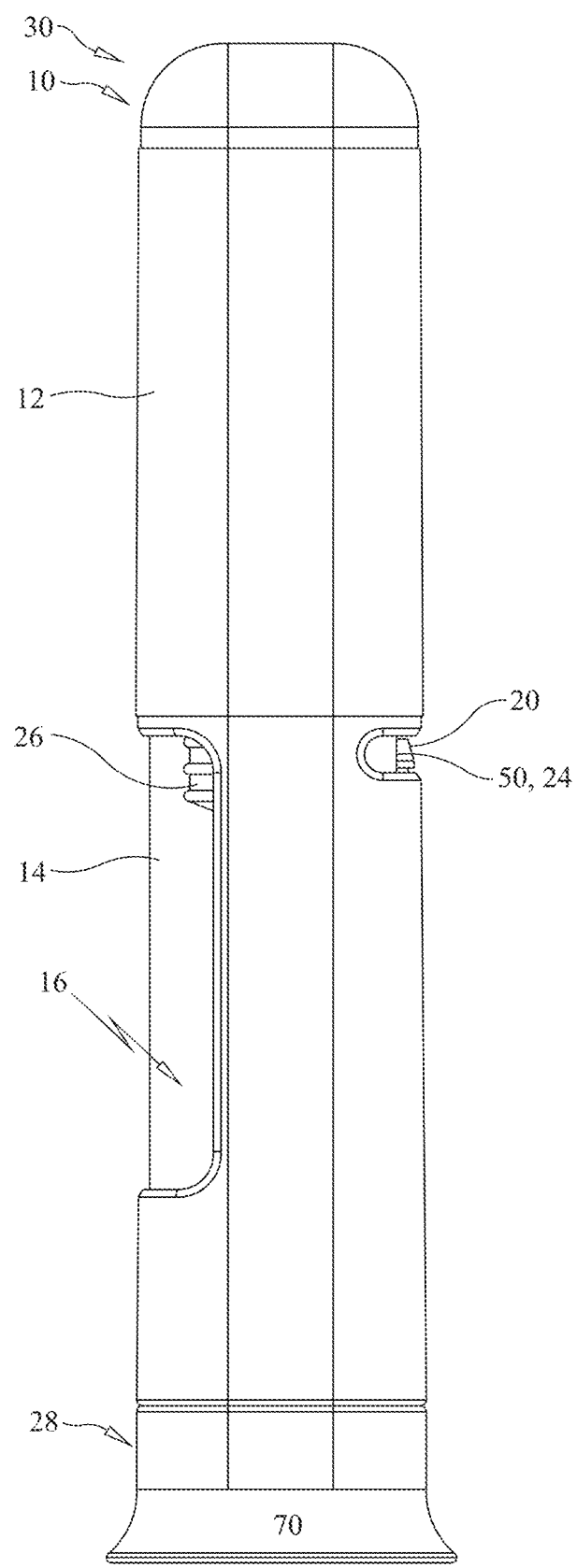
FIG. 1B is a further side elevational view of the autoinjector of FIG. 1A in the storage state.

Referring initially to FIG. 1, an autoinjector 10 is illustrated in accordance with a first embodiment. FIGS. 1A and 1B show side views of an autoinjector 10. The autoinjector 10 is a medical instrument that serves the purpose of administering a single dose of medicament M. The autoinjector 10 can not only be used by medical staff, but also by a patient themselves to administer the medicament M.

The autoinjector 10 has a housing 12 with a syringe window 14 (see FIG. 1A) present therein. A pre-filled syringe 16 is arranged within the housing 12 and visible via the syringe window 14. The pre-filled syringe 16 is filled with the medicament M.

A needle guard 18 (see e.g., FIG. 2A) is arranged at a proximal end 28 of the autoinjector 10. The needle guard 18 has the function of protecting a patient from a needle 34 (see e.g., FIG. 4B) before and after use of the autoinjector, i.e., in a storage state and in a lock-out state of the autoinjector 10.

In this connection it should be noted that the terms "proximal" and "distal" refer to the position of the needle 34 relative to a patient with "proximal" meaning closest to a main mass of the body of a patient and "distal" meaning it is more distant from the main mass of the body of a patient. Also, the term "proximal direction" refers to a longitudinal direction towards the proximal end of the autoinjector 10, and the term "distal direction" refers to a longitudinal direction towards the distal end of the autoinjector 10. The transverse direction T refers to a direction that is perpendicular to the proximal direction and the distal direction.

FIG. 1B shows a status indicator window 20 in which a first part outer surface 50 of a drive chassis 24 of the autoinjector 10 is visible.

A cap 70 is arranged at the proximal end 28 of the autoinjector 10 disposed opposite to a distal end 30 of the autoinjector 10. The cap 70 covers both the needle 34 and the needle guard 18 in the storage state of the autoinjector 10.

Figures 2A, 2B:
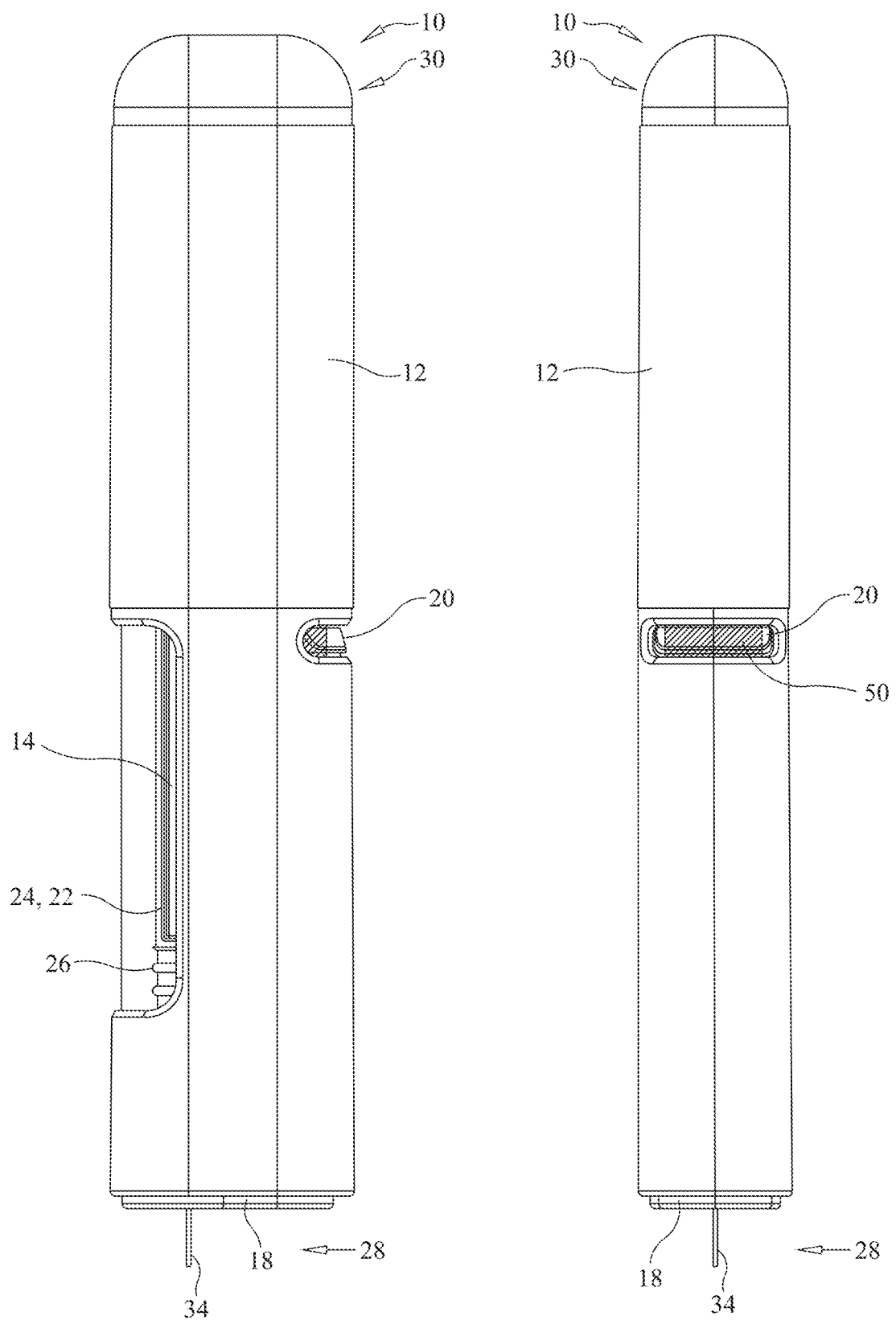
FIG. 2A is a side elevational view of the autoinjector of FIG. 1A in a dispensing state.
FIG. 2B is a further side elevational view of the autoinjector of FIG. 1A in the dispensing state.

FIGS. 2A and 2B show the autoinjector 10 of FIG. 1 with the cap 70 removed and the needle guard 18 moved distally, i.e., moved away from the proximal end 28, and into the autoinjector 10. The distal movement of the needle guard 18 into the autoinjector also brings about an engagement of a release mechanism 40 (see e.g., FIG. 4).

On engaging the release mechanism 40, the drive chassis 24 (see also FIG. 3) is moved proximally and a dispensing limb 22 thereof moves a plunger 26 through the pre-filled syringe 16 in order to dispense the medicament M via the needle 34.

In this connection it should be noted that the plunger 26 can be a part separate from the dispensing limb 22 and can be pre-arranged within the pre-filled syringe and configured to be engaged by the dispensing limb 22.

In other designs of the autoinjector 10, the plunger 26 can be a part of the dispensing limb 22.

FIG. 2A shows the presence of the dispensing limb 22, the drive chassis 24 and the plunger 26 in the syringe window 14 following the movement of the drive chassis 24 in the proximal direction, i.e., at an end of dose state of the autoinjector 10.

FIG. 2B shows a second part outer surface 52 of the drive chassis 24 in the status indicator window 20.

In the drawings shown above, the status indicator window 20 on the side of autoinjector 10 shows a device status in clear, binary form, which is likely to be very useful particularly to naive users. Before (and possibly during) dispensing, the color displayed through the window is printed on the drive chassis 24 (see also FIG. 3). At the end of the dispensing, the molded color (indicated with the hashed lines) of the drive chassis 24 is displayed through the status indicator window 20.

Other configurations of display, for example employing graphics to indicate that dispensing is in progress, icons or text, are possible.

Moreover, before dispensing, the dispensable fluid volume of the medicament M is clearly visible through the syringe window 14 that is formed as a large wrap-around window in the housing 12. The geometry of this window 14 is intended to maximize the viewing angle for the user.

The progress of the dispensing can also be viewed through the window 20 as a movement of the plunger 26 and of the drive chassis 24 is visible through the syringe window 14.

At the end of dispensing, the syringe window 14 is filled with the drive chassis 24 and the plunger 26 to provide additional visual indication that the autoinjector 10 has been used. This means that two forms of different visual indication of the end of dose are present. The part of the drive chassis 24 visible through the syringe window 14 could be provided with a surface decoration or marking, e.g., printed in a different color to provide further visual communication of the end of the dose.

Figure 3:
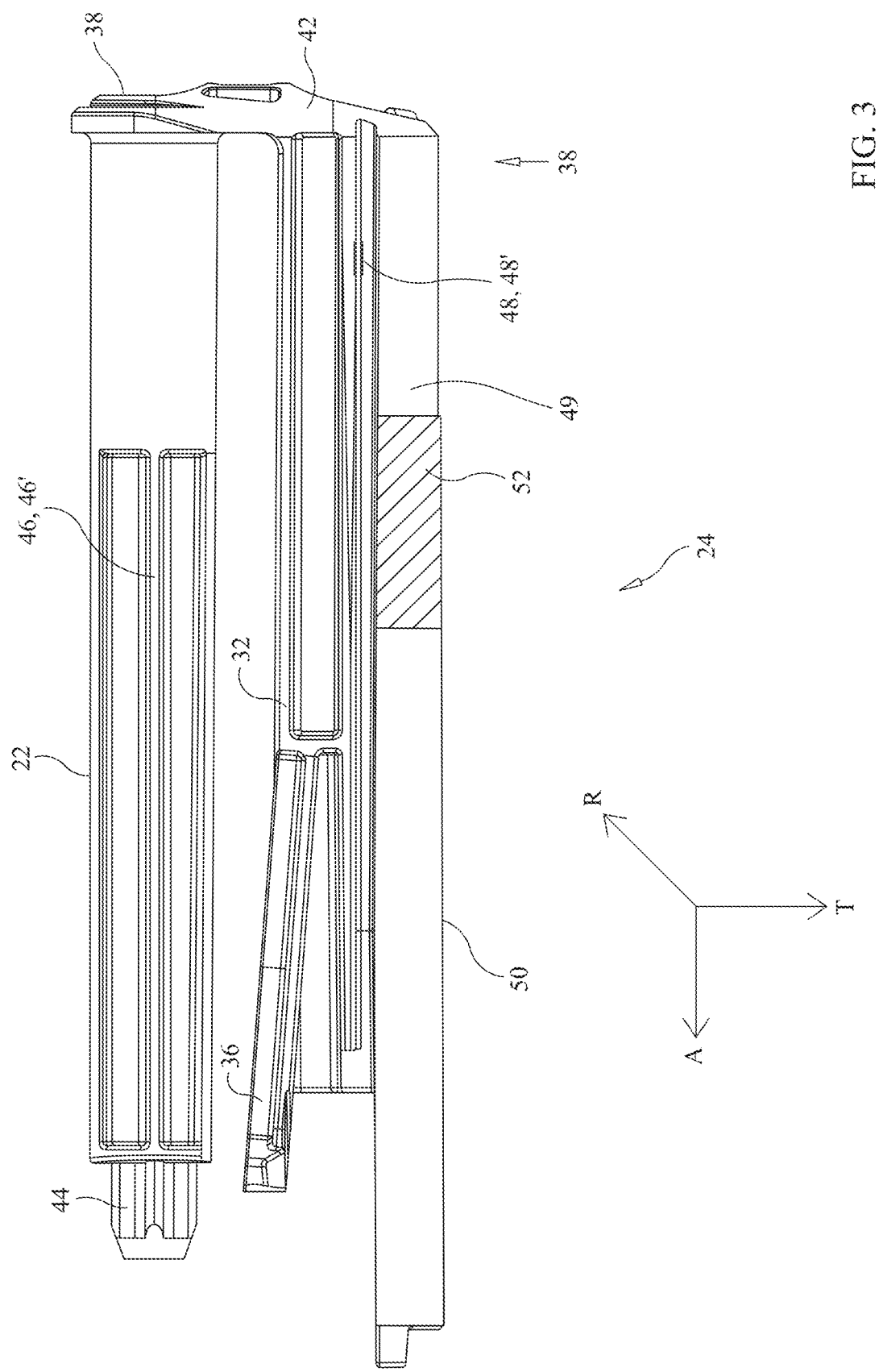
FIG. 3 is a side elevational view of a drive chassis for the autoinjector of FIG. 1A.

FIG. 3 shows the drive chassis 24. The drive chassis 24 comprises the dispensing limb 22 and a trigger limb 32. The trigger limb 32 and the dispensing limb 22 are arranged in parallel to one another. The drive chassis 24 is a component that is configured to move in a straight line within the housing in order to drive the medicament M out of the pre-filled syringe on activation of the autoinjector 10.

The trigger limb 32 and the dispensing limb 22 are arranged in an at least generally U-shaped manner respectively in a U-shaped manner and are connected to one another at a distal end 38 of the drive chassis 24 via a web 42, i.e., axially offset from one another in a transverse direction T with a length of the trigger limb 32 being longer than a length of the dispensing limb 22.

In this connection it should be noted that in other designs the dispensing limb 22 can also have the same length as the trigger limb 32 or even be longer than the trigger limb 32.

A plunger support 44 is arranged at an end of the dispensing limb 22 remote from the web 42. The plunger support 44 is configured to engage the plunger 26 that moves through the pre-filled syringe 16, i.e., the plunger support 44 is configured to act on the pre-filled syringe 16 of the autoinjector 10 via the plunger 26 that is arranged within the pre-filled syringe 16.

A trigger arm 36 is arranged to extend proximally from the trigger limb 32 in both a transvers direction T and a radial direction R relative to an axial direction A, with the axial direction A extending in parallel to the trigger limb 32. The trigger arm 36 is arranged extending from the trigger limb 32 in a direction remote from the distal end 38.

The trigger arm 36 is fixedly attached to the trigger limb 32 and moveable relative to the trigger limb 32.

The trigger arm 36 is connected to the trigger limb at a position corresponding to a length of the trigger limb 32 corresponding to 20 to 80% of a length of the trigger limb 32 from the distal end 38.

In this connection it should be noted that the drive chassis 24 is formed in one piece, i.e., the trigger limb 32, the dispensing limb 22, the plunger support 44 and the trigger arm 36 are integrally formed in one piece, preferably from one and the same material, e.g., in the same injection mold, or, if manufactured by additive manufacturing techniques, in one production cycle.

The drive chassis 24 can be installed in the autoinjector 10 shown in connection with FIGS. 1A, 1B and 2. The drive chassis 24 can then be linearly guided within the housing 12 of the autoinjector 10 on moving the autoinjector 10 from a storage state into a dispensing state of the autoinjector.

For this purpose, the drive chassis 24 can have first and second guiding aids 46, 48 cooperating with corresponding structures present within the housing 12. In the present example, the first and second guiding aids 46, 48 are formed by first and second grooves 46', 48' that respectively extend in the axial direction A along the dispensing limb 22 respectively the trigger limb 32. The first and second grooves 46', 48' cooperate with lugs 164, 228 (see e.g., FIG. 10A respectively FIG. 13G) present on an inside wall of the housing 12.

Alternatively, the drive chassis 24 can comprise lugs cooperating with corresponding grooves in the housing 12 as the first and second guiding aids 46, 48. Alternatively, the trigger limb 32 and the dispensing limb 22 can be shaped in such a way that they cooperate with guide structures present within the housing 12, by way of example, the trigger limb 32 and the dispensing limb 22 can have a round outer shape in a cross-section therethrough perpendicular to the axial direction A, with the round outer shapes of the trigger limb 32 and the dispensing limb 22 then being guided in complementary shaped parts of the housing 12.

Figure 4A:
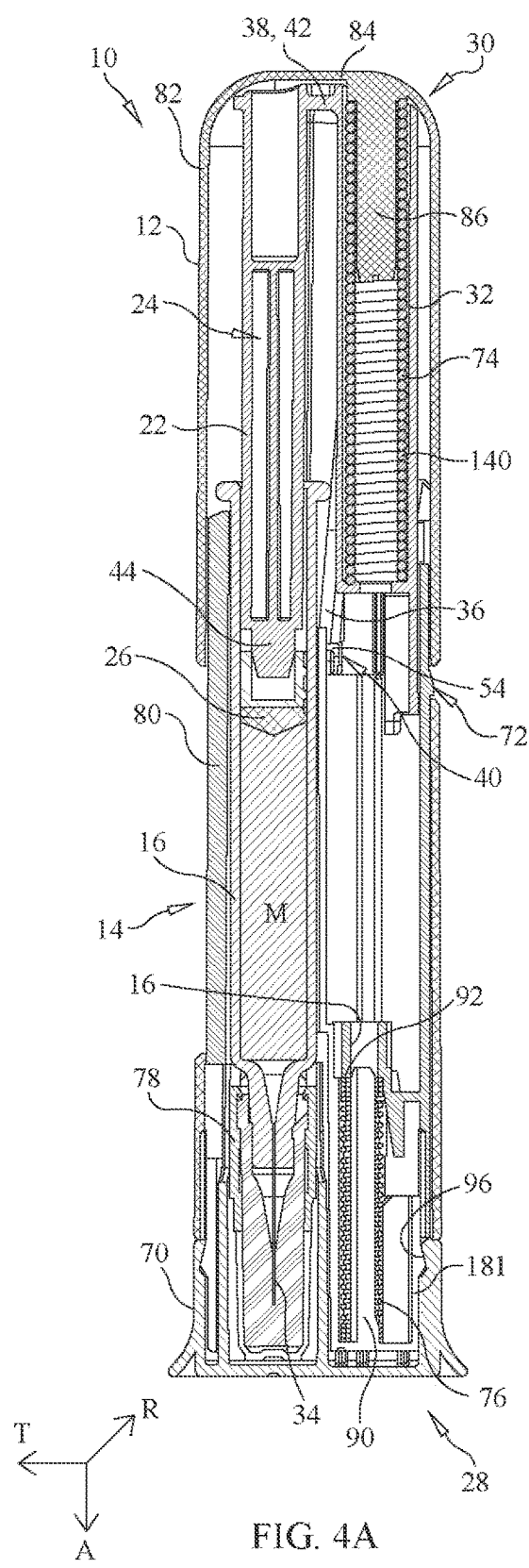
FIG. 4A is a sectional view of the autoinjector of FIG. 1A in the storage state.

In the storage state the trigger arm 36 is held at a stop feature 54 (see e.g., FIG. 4A). On moving the autoinjector 10 from the storage state into the dispensing state of the autoinjector, the trigger arm 36 is deflected out of engagement from the stop feature 54. For this purpose, the trigger arm 36 is moveable relative to the trigger limb 32, i.e., the position of the trigger arm 36 can be moved relative to the trigger limb 32.

In this connection it should be noted that the stop feature 54 is arranged at a height along the axial direction A of the housing 12 corresponding to a length of 45% of the length of the housing 12 from the distal end 30 of the autoinjector 10.

In this connection it should be noted that the stop feature 54 can be arranged at a height along the axial direction A of the housing 12 selected in the range of 30 to 70% of the length of the housing 12 from the distal end 30 of the autoinjector 10.

In this connection it should be noted that the trigger arm 36 is configured to move radially in the radial direction R and transversely in the transverse direction T with respect to the trigger limb 32.

The trigger limb 32 has an outer surface 49 comprising the first part outer surface 50 (hashed surface) and the second part outer surface 52 (black outer surface). The first and second part outer surfaces 50, 52 are present at a transverse side of the trigger limb 32, i.e., pointing in the transverse direction T. The first and second part outer surfaces 50, 52 are visible via the status indicator window 20 in different states of use of the autoinjector 10. Specifically, as indicated in FIG. 1B, the first part outer surface 50 is visible via the status indicator window 20 in the storage state of the autoinjector 10 and the second part outer surface 52 is visible via the status indicator window 20 in the dispensing state towards an end of dose and in the lock-out state of the autoinjector 10 following an end of dose.

A first limb of the U-shaped drive chassis 24 is formed by the dispensing limb 22 and a second limb of the U-shapes drive chassis 24 is formed by the trigger limb 32. A distal end of the syringe window 14 is arranged at approximately the same height as a distal end of the status indicator window 20. The syringe window 14 and the status indicator window 20 are arranged in a part of the housing 12 where an inner body 80 and an outer body 82 (see FIGS. 4A to 4C) overlap. The third part of the drive chassis 24 that may be visible in the syringe window 14 is the dispensing limb 22 in addition to which the plunger 26 of the pre-filled syringe 16 is also visible. In this connection it should be noted that the first and second parts 50, 52 of the drive chassis 24 are not visible in the syringe window 14. So that a user (not shown) can distinguish between the different states of use, i.e., between the first and second part outer surfaces 50, 52, the appearances of the first and second part outer surfaces 50, 52 differ from one another, i.e., these are different from one another.

In the present example, the second part outer surface 52 comprises a marking printed thereon in the form of a hashed structure, other kinds of surface decorations and/or markings can be employed. The first part outer surface 50 is, for example, formed in the same color as the remaining drive chassis 24. However, the first part outer surface 50 can also have some other color comprise some form of surface marking and/or decoration or other form of visual indicator.

By way of example words such as "full and/or ready" and "empty and/or used" could printed on the first and second part outer surfaces 50, 52. Additionally and/or alternatively, the first and second part outer surfaces 50, 52 can be colored differently from one another, e.g., in red or green or the like.

Figure 4B:
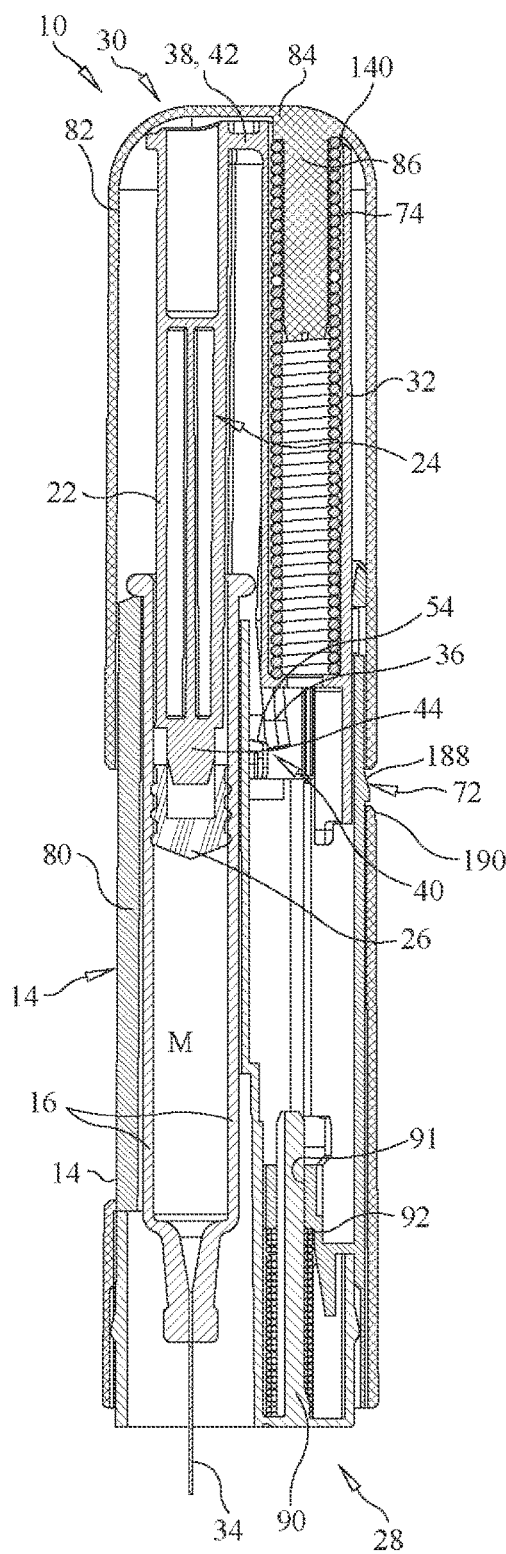
FIG. 4B is a sectional view of the autoinjector of FIG. 1A in the activated state shortly before the dispensing state.
Figure 4C:
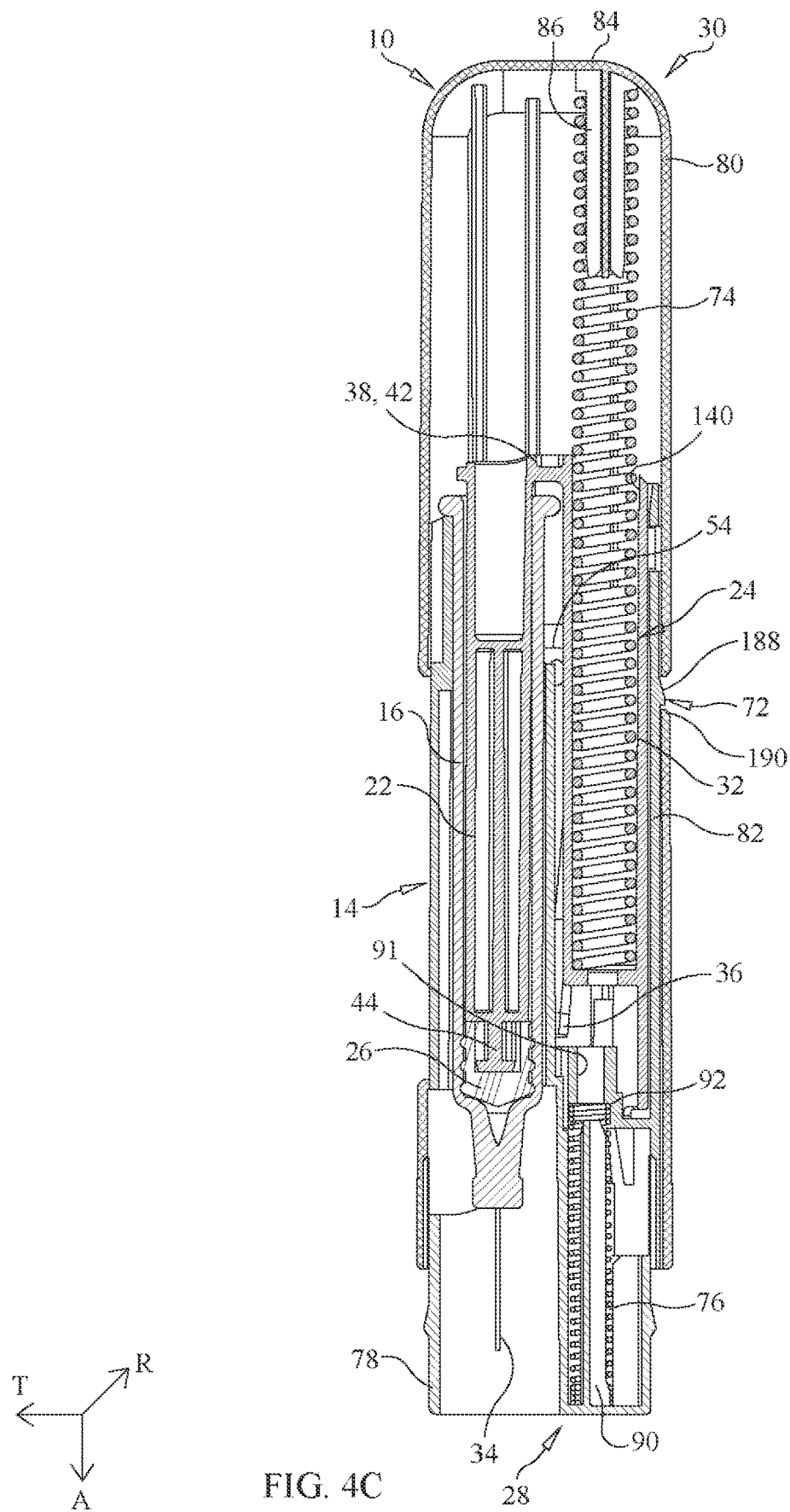
FIG. 4C is a sectional view of the autoinjector of FIG. 1A in a lock-out state.

The autoinjector 10 shown in FIGS. 4A to 4C comprises the needle guard 18 the removable cap (only FIG. 4A), the pre-filled syringe 16 arranged within the housing 12, a drive spring 74, a lock-out spring 76, and a removable needle shield 78 (RNS). FIG. 4A shows the autoinjector 10 of FIG. 1A in the storage state. FIG. 4B shows the autoinjector 10 of FIG. 1A in the activated state shortly before the dispensing state. FIG. 4C shows the autoinjector 10 of FIG. 1A in the lock-out state. In the storage state of the autoinjector 10, a cap 70 is installed at the proximal end 28 of the autoinjector 10. On removal of the cap 70, the needle guard 18 of the autoinjector 10 becomes accessible. The needle guard 18 is mounted axially moveable in the housing 12 for movement between the storage state, the dispensing state and the lock-out state. The needle guard 18 adopts different axial positions relative to the housing 12 in each one of the storage state, the dispensing state and the lock-out state. As indicated in FIG. 4B, the needle guard 18 is moved in the distal direction along the axial direction A to make the needle 34 accessible from the outside, i.e., so that a patient can insert the needle 34 into his skin.

The needle guard 18 can be moved automatically in the distal direction along the axial direction A as the patient moves the autoinjector 10 towards the injection point, as the contact with the patients' skin will automatically move the needle guard into the housing 12 of the autoinjector 10. For this purpose, the needle guard 18 is configured to be axially moved in the distal direction between the storage state and the dispensing state. On moving the needle guard from the storage state into the dispensing state the lock-out spring 76 is biased between the needle guard 18 and an inner body 80 of the housing 12. Once a medicament M has been administered, i.e., dispensed from the autoinjector 10, the needle guard 18 is configured to be axially moved in the proximal direction between the dispensing state and the lock-out state on removing the autoinjector 10 from the injection site. This movement of the needle guard 18 is automatically brought about by a relaxation of the lock-out spring 76. The housing 12 is a two-part housing formed of the inner body 80 and an outer body 82 that are fixed in position relative to one another and that are snap fit to one another via a connection 72.

As shown in FIG. 4B, the connection 72 is formed by a nose 188 formed at the inner body that is configured to latch to a window 190 formed in the outer body 82. In this connection it should be noted that the connection 72 can also be brought about via a different kind of connection. For example, the nose 188 can be formed at the outer body 82 and project towards the inner body 80 and engage the window 190 then formed at the inner body 80. Alternatively, different forms of connector can be used to form the connection 72.

The trigger arm 36 is actuated on by the needle guard 18 of the autoinjector 10 on moving the autoinjector 10 from the storage state into the dispensing state of the autoinjector 10. As can be seen from a comparison of FIGS. 4A and 4B, the trigger arm 36 is deflected in the transverse direction T. Moreover, the trigger arm 36 is also deflected in the radial direction R.

The drive spring 74 is arranged within the housing 12 of the autoinjector 10. The drive spring 74 is specifically arranged between a distal housing wall 84 and the drive chassis 24. More specifically, the drive spring 74 is arranged between the distal housing wall 84 of the outer body 82 and within the trigger limb 32 of the drive chassis 24. In order to fix a position of the drive spring 74, the drive spring 74 can be arranged at a projection 86 projecting proximally from the distal housing wall 84 of the outer body 82. The drive spring 74 is received within a passage 140 formed in the trigger limb 36 of the drive chassis 24. This means that the trigger limb 36 is configured to receive the drive spring 74. In the present example, the passage 140 has a cylindrical shape that is complementary to an outer shape of the drive spring 74.

As can be seen from a comparison of FIGS. 4A, and 4B with FIG. 4C the drive spring 74 is relaxed in comparison to the other two states in the lock-out state. This is because a release of the engagement between the trigger arm 36 and the stop feature 54 permits a proximal movement of the drive chassis 24 relative to the housing, i.e., relative to the inner and outer bodies 80, 82 under relaxation of the previously biased drive spring 74. The drive spring 74 also biases the trigger arm 36 in the storage state of the autoinjector 10 with respect to the housing 12 of the autoinjector 10 by urging this against the stop feature 54 by means of the inherent spring bias of the drive spring 74.

The drive spring 74 is further configured to drive the plunger support 44 of the drive chassis of the autoinjector 10 into the pre-filled syringe 16. This is due to the fact that the drive chassis 24 is linearly guided within the housing 12 and is permitted to move proximally once the trigger arm 36 is released from its engagement with the stop feature 54.

The needle guard 18 surrounds the needle 34 of the pre-filled syringe 16 in the storage state and in the lock-out state. Once the cap 70 is removed and the autoinjector 10 has been moved into the dispensing state, the needle guard 18 does not surround the needle 34 of the pre-filled syringe 16.

As indicated in FIGS. 4A to 4C, the autoinjector 10 further comprises the lock-out spring 76 that is arranged between the needle guard 18 and the housing 12, more specifically between the inner body 80 and the needle guard 18. The lock-out spring 76 is biased between an end wall 88 of the needle guard 18 and a proximal end 92 of the inner body 80. The end wall 88 is arranged proximally with respect to the inner body 80 and the drive chassis 24.

Moreover, the needle guard 18 comprises a projection 90 projecting distally from the proximal end 28. The lock-out spring 76 is arranged at the projection 90, in particular, the projection 90 projects into the lock-out spring 76. The needle guard 18 is configured to compress the lock-out spring 76 on moving between the storage state and the dispensing state. This is possible as the lock-out spring 76 abuts a proximal end 92 of the inner body 80 of the autoinjector 10 and the projection 90 is guided through an aperture 91 present in the inner body 80.

Following a use of the autoinjector 10 and removal of the autoinjector from an injection site, the needle guard 18 is configured to be moved by a relaxation of the lock-out spring 76 between the dispensing state and the lock-out state in a proximal direction. In this connection it should be noted that the projection 90 could also be provided at the inner body 80 such that it projects towards the proximal end 28 of the needle guard 18. If this option is selected, then a length of the projection 90 has to be adapted such that the projection does not prevent a movement of the needle guard in the distal direction and/or such that it does not project beyond the needle guard 18 in the dispensing state so as to not come into contact with a patient's skin, e.g., if it cooperates with an aperture (not shown) of the needle guard 18.

In the storage state of the autoinjector 10, the needle guard 18 is arranged at a first axial position. In the dispensing state the needle guard 18 is arranged at a second axial position and in the lock-out state the needle guard 18 is arranged at a third axial position. The first, second and third axial positions respectively differ from one another, with the third axial position being more proximal than the first and second axial positions and the first axial position being more proximal than the second axial position with respect to the housing 12. In this connection it should be noted that the third axial position can be the same or very similar to the first axial position in other designs of the autoinjector 10. This means that an outer length of the autoinjector 10 with the cap 70 removed is longest in the lock-out state, shortest in the dispensing state and of medium length in the storage state.

Figure 5A:
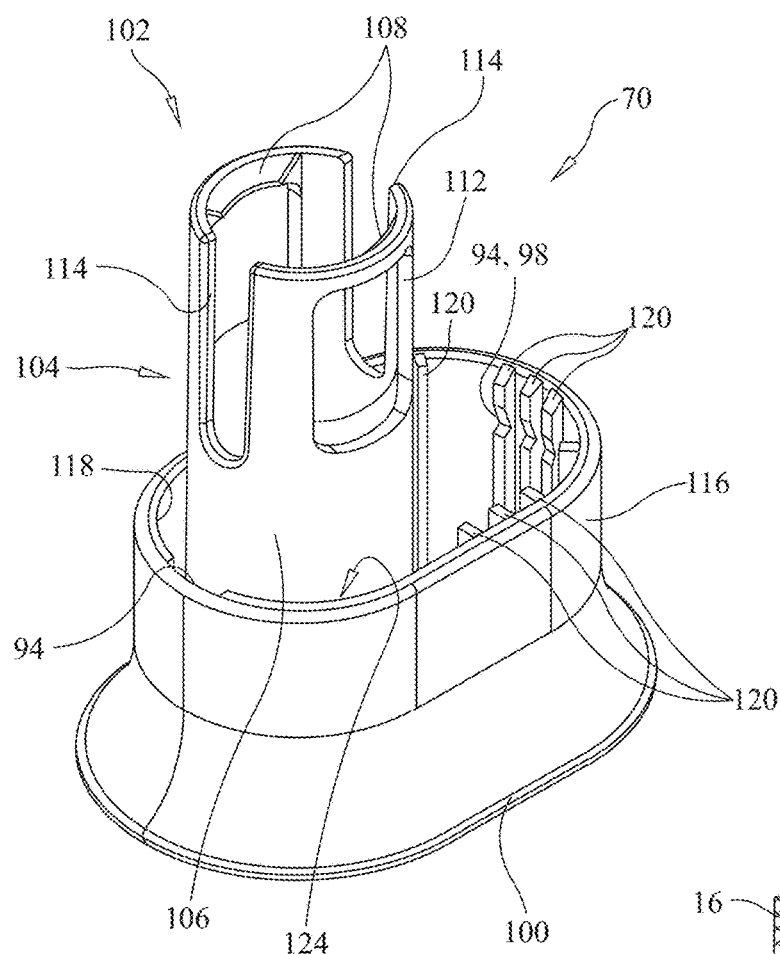
FIG. 5A is a view of a cap of the autoinjector of FIG. 1A.

FIG. 5A shows a perspective view of the removable cap 70. The cap 70 is of single piece design. The needle guard 18 is configured to cooperate with the cap 70 via one or more snap-fit connections 94, wherein each snap fit connection 94 comprises a protruding edge 96 (see e.g., FIG. 6) cooperating with a corresponding snap-fit area 98. In this connection it should be noted that each of the following components can be respectively integrally formed in one piece, preferably from one and the same material, e.g., in the same injection mold, namely the outer body 82, the inner body 80, the drive chassis 24, the needle guard 18, the cap 70, and/or the needle shield 78.

As shown in FIG. 5A, the removable cap 70 has a base 100. The cap 70 tapers outwardly in the region of the base 100 such that the base 100 of the cap 70 has a larger outer diameter than the remaining cap 70. This is particularly beneficial as the base 100 can act as a stand for the autoinjector 10 in the storage state of the autoinjector 10.

A needle guard facing end 102 of the cap 70 comprises a needle shield holder 104 at an end of the cap 70 disposed opposite to the base 100. The needle shield holder 104 is configured to hold the removable needle shield 78 covering the needle of the pre-filled syringe 16 in the storage state of the autoinjector 10. The inner wall 106 of the needle shield holder 104 further comprises two windows 112. A respective one of the inwardly facing projections 108 is arranged at each of the windows 112. Two recesses 114 are formed in the inner wall 106 of the needle shield holder 104 of the cap 70. The recesses are arranged between respective parts of the needle shield holder 104 having the windows 112. The needle shield holder 104 projects distally from the base 100 of the cap 70 and is surrounded by an outer wall 116 of the cap 70. An inner surface 118 of the outer wall 116 of the cap 70 comprises several ribs 120.

Figure 5B:
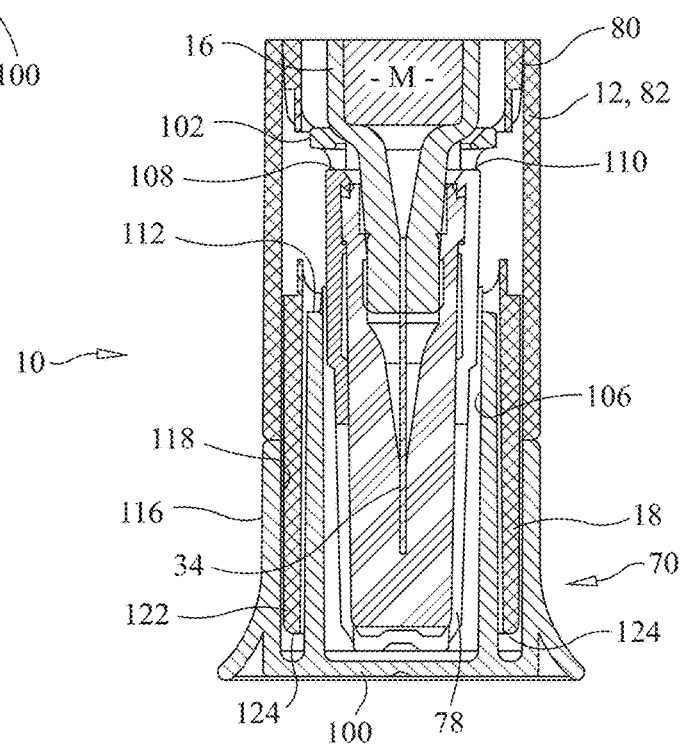
FIG. 5B is a part sectional view of the autoinjector in the region where the cap of FIG. 5A is installed at the needle guard end of the autoinjector.

As indicated in FIG. 5B, a front end 122 of the needle guard 18 is arranged within an opening 124 of the cap 70. The opening 124 is formed between the outer wall 116 of the cap 70 and the needle shield holder 104.

The ribs 120 are configured to press radially inwardly, i.e., in the radial direction R, and transversely inwardly, i.e., in the transverse direction T, against the needle guard 18 in the storage state of the autoinjector 10.

As also shown in FIG. 5B, the removable needle shield 78 is arranged within the needle shield holder 104. For this reason, an inner wall 106 of the needle shield holder 104 comprises inwardly facing projections 108 at the needle guard facing end 102 that engage a syringe facing surface 110 of the needle shield 78.

Figure 6:
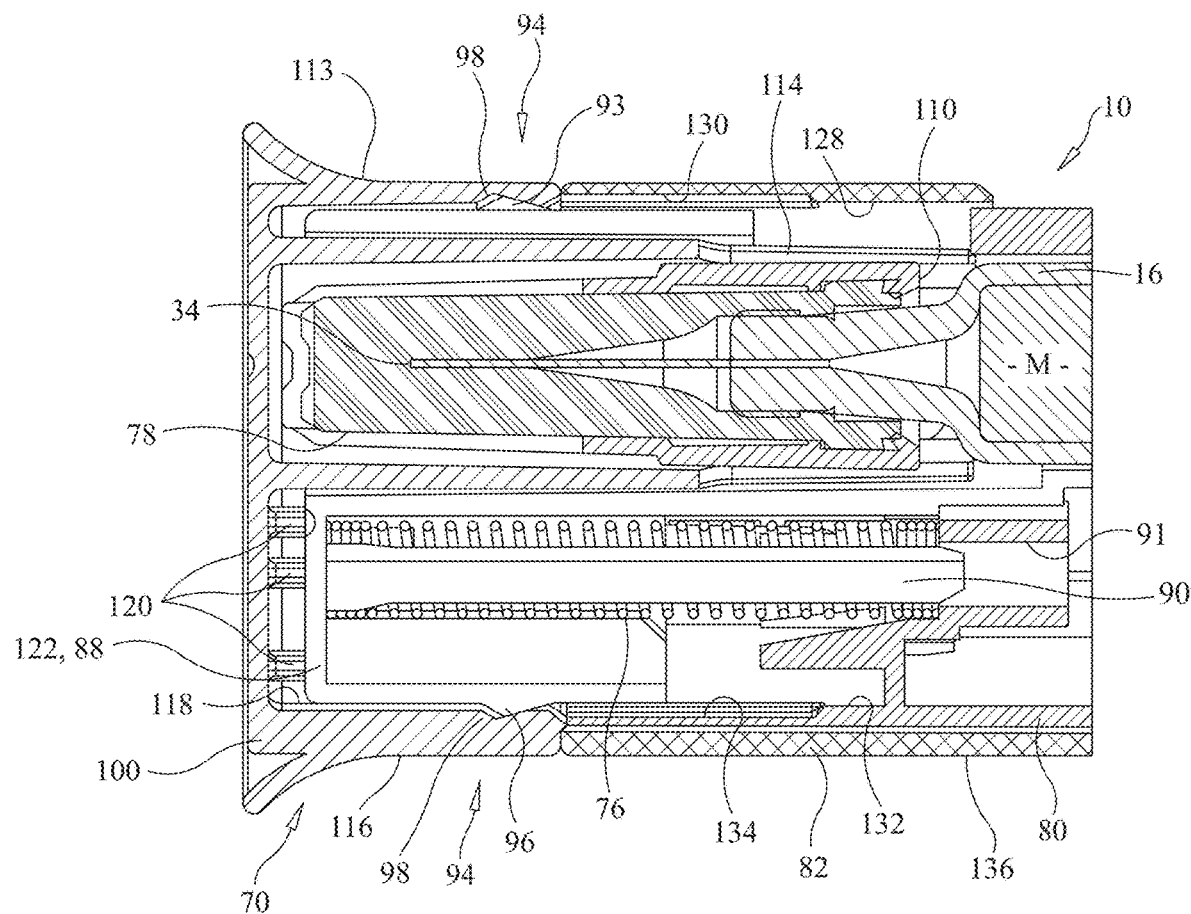
FIG. 6 is a part sectional view of the autoinjector showing the cap installed at the needle guard end of the autoinjector.

As indicated in FIG. 6, the protruding edges 96 are provided at an outer surface 126 of the needle guard 18. The snap-fit areas 98 are provided at the inner surface 118 of the cap 70.

The snap-fit connection 94 holds the cap 70 in place in the storage state of the autoinjector. The cap 70 is removably connected to the needle guard 18 and, on removal of the cap 70, the needle shield 78 is also removed from the autoinjector 10, as the projections 108 of the cap press on the syringe facing surface 110 of the removable needle shield 78 to entrain the removable needle shield in the proximal direction on removal of the cap 70.

In order to permit an as compact as possible design of the autoinjector 10, an inner surface 128 of the outer body 82 comprises a groove 130 in which one of the protruding edges 96 can axially move relative to the outer body 82 on an axial movement of the needle guard 18.

Similarly, an inner surface 132 of the inner body 80 comprises a further groove 134 in which a further one of the protruding edges 96 can axially move relative to the inner body 80 on an axial movement of the needle guard 18 relative to the housing 12.

The snap-fit projection 96 thereby forms detent features on the needle guard 18 that engage with corresponding features on the cap in order to provide a tight axial fit between the components following assembly.

A reverse arrangement of the detent features can also be possible, e.g., snap-fit areas can be present at the housing 12 and corresponding snap-fit projections could be present at the cap 70.

The proximal side of these detent features (snap-fit projections 96) on the needle guard is relatively steep, i.e., the proximal side of the snap-fit projections 96 is steeper than the distal side of the snap-fit projections 96 in the axial direction, so that once the cap 70 is removed, if the user attempts to re-attach it, the force to reengage the detent features is high enough to cause the needle guard 18 to be moved distally until the detent features are hidden within the housing 12.

In this way, re-attachment of the detent features will not be possible (although the cap can be held in place by the engagement of the RNS 78 and the syringe glass). The distance by which the needle guard 18 is moved in order to hide the detent features is designed to be less than the distance required to trigger dispensing, so that attempted re-attachment of the cap 70 in this way does not trigger dispensing.

When the cap 70 is attached to the autoinjector 10, i.e., to the needle guard 18 via the snap-fit connection 94, the cap 70 prevents axial movement of the needle guard 18 when attached to the needle guard 18 in the storage state.

As further indicated in FIG. 6, the outer wall 116 of the cap 70 contacts an outer wall 136 of the housing 12 in the storage state of the autoinjector 10. The outer wall 116 of the cap 70 and the outer wall 136 of the housing 12 do not overlap in an axial direction A of the autoinjector 10. Moreover, the outer wall 116 of the cap 70 and the outer wall 136 of the housing 12 radially overlap in the storage state of the autoinjector 10. It should be noted in this connection that the outer wall 136 of the housing is the outer wall 136 of the outer body 82 forming a part of the two-part housing 12.

Clip features in the form of the projections 108 on the cap 70 act on the distal surface of the rigid needle shield (RNS) 78 to grip onto it and remove it from the pre-filled syringe 16 when the cap 70 is pulled off by the user. In this connection it should be noted that a 'three plate tool' construction can be used to mold the cap 70, including the clip features (projections 108) in a single component in a common injection mold (not shown) where state of the art devices typically construct similar caps from two or more separate components. The projections 108 are supported by the needle guard 18 during removal of needle shield 78, helping to prevent them from splaying outwards and disengaging, as the needle shield holder 104 is biased radially inwardly by the needle guard 18.

Figure 7A:
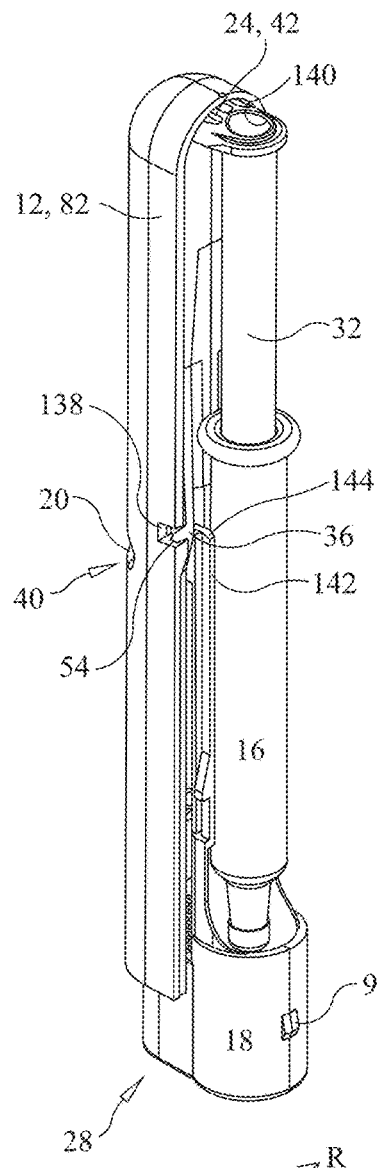
FIGS. 7A to 7C are part sectional views of the autoinjector, with a part of the housing removed, such that one can see components of a release mechanism of the autoinjector on activating the autoinjector.
Figure 7B:
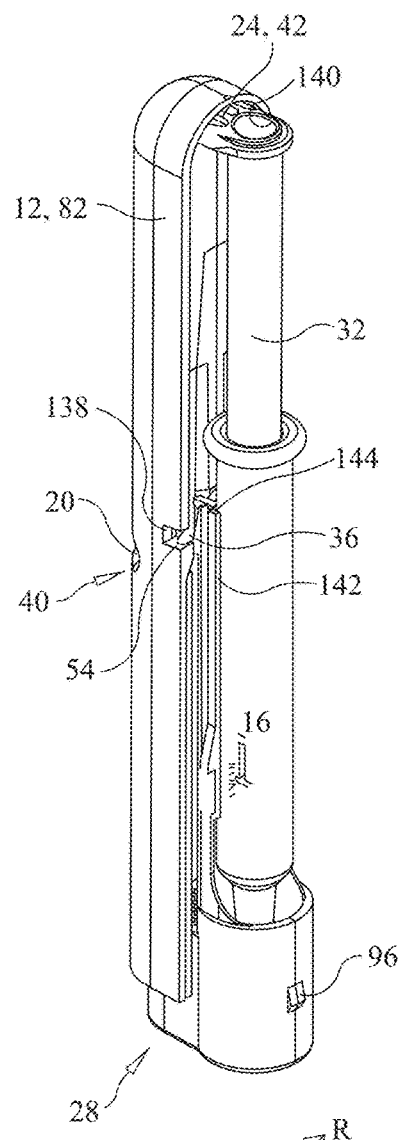
Figure 7C:
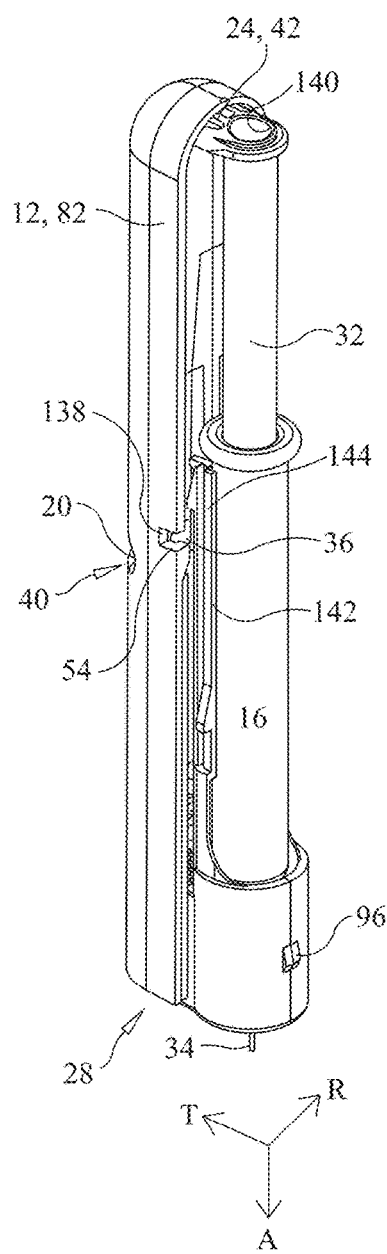

FIG. 7A to 7C show part sectional views of the autoinjector 10, with a part of the housing 12 removed, such that one can see components of the needle guard 18, the drive chassis 24, the pre-filled syringe 16 and the housing 12 on activating the autoinjector 10. FIG. 7A to 7C illustrate a distal movement of the needle guard 18 into the housing 12 and how this then engages the release mechanism 40 comprising the trigger arm 36 and the stop feature 54 before the drive chassis 24 is moved proximally in order to administer the medication M stored in the pre-filled syringe 16.

The needle guard 18 comprises a plunger arm 142 as part of the release mechanism 40 of the autoinjector 10. The plunger arm 142 extends distally from the front end 122 of the needle guard 18. As can be seen the relative position of the plunger arm 142 relative to the housing 12 varies and a distance the needle guard 18 projects beyond the housing 12 at the proximal end 28 reduces between FIG. 7A to 7C.

Figure 8A:
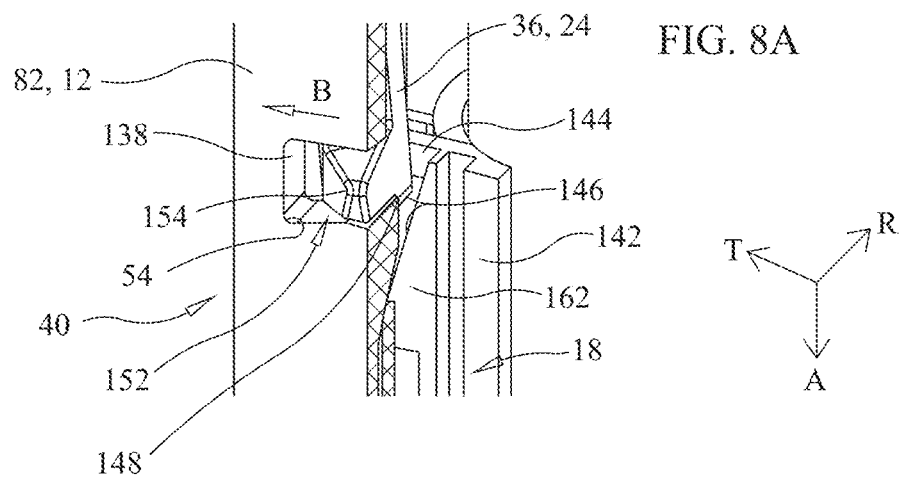
FIGS. 8A to 8C are detailed views of the release mechanism of the autoinjector of FIG. 7.
Figure 8B:
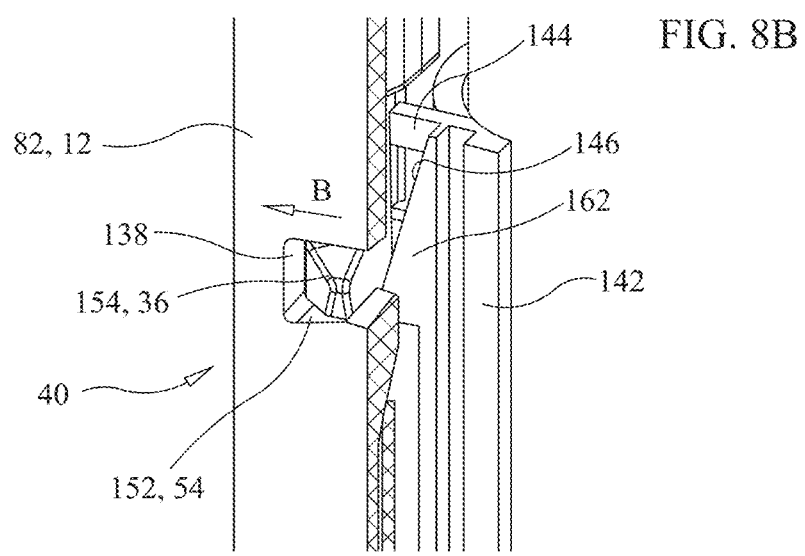
Figure 8C:
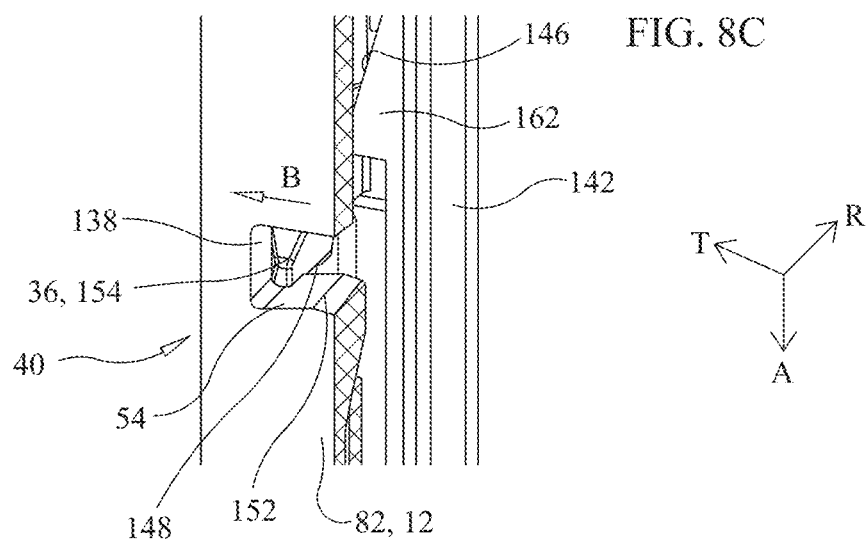

FIG. 8A to 8C show detailed views of the different positions of the release mechanism 40 of the autoinjector 10 corresponding to the views shown in FIGS. 7A to 7C. FIG. 8A shows an enlarged view of the components of the release mechanism 40 of the autoinjector 10 which comprises the trigger arm 36 of the drive chassis 24, and the stop feature 54 present in an opening 138 of the housing 12 with which the trigger arm 36 cooperates. In this connection it should be noted that the opening 138 of the housing 12 is indicated as a through-going opening, i.e., it is open both at an outer wall of the housing 12 as well as an inner wall of the housing 12. It should however be noted that it can also be formed as a recess in the inner wall of the housing 12 such that it does not go through the wall of the housing 12.

The drive chassis 24 is mounted in the housing 12, the drive chassis 24 is biased with respect to the housing 12 via the drive spring 74. The drive chassis 24 is further fixed with respect to the housing 12 and a movement relative to the housing 12 in the storage state of the autoinjector 10 via the trigger arm 36 that is held at the opening 138.

In the storage state of the autoinjector 10, the drive spring 74 biases the trigger arm 36 in the axial direction A against the stop feature 54. The trigger arm 36 is present at the right hand side in the opening 138 (of the present Figure).

In order to activate the autoinjector 10 and to release the drive chassis 24 for its proximal movement, the autoinjector 10 comprises the release mechanism 40.

The release mechanism permits a relative movement between the needle guard 18 and the drive chassis 24. This relative movement is achieved by an axial movement of the needle guard 18 towards the drive chassis 24 which releases the fixing of the drive chassis 24 with respect to the housing 12 on activation of the autoinjector 10.

For this purpose, the plunger arm 142 is configured to cooperate with the trigger arm 36 of the drive chassis 24 for activation of the release mechanism 40. On moving the plunger arm 142 in the distal direction the plunger arm 142 contacts and thereby deflects the trigger arm 36 in the transverse direction T as indicated by the arrow B and a comparison of the position of the trigger arm 36 relative to the opening 138 shown in FIGS. 8A to 8C.

The plunger arm 142 of the needle guard 18 comprises a blocking rib 144. The blocking rib 144 is configured to block a radial movement of the trigger arm 36 when the plunger arm 142 contacts the trigger arm 36. In this connection it should be noted that the blocking rib 144 is also configured to block a radial movement of the trigger arm 36 during the storage state prior to the plunger arm 142 contacting the trigger arm 36 due to an axial movement of the needle guard 18. In order to engage the trigger arm 36, the plunger arm 142 comprises a cam 162. The cam 162 has an engagement surface 146 configured to engage the trigger arm 36. The engagement surface 146 projects from the cam 162 of the plunger arm 142 at a position adjacent to the blocking rib 144 in the transverse direction T such that it faces the trigger arm 36. The trigger arm 36 comprises a web 148. The web 148 extends axially (proximally) below the projection 154 from the trigger arm 36 and provides a contact surface in the transverse direction T facing the cam 162 of the plunger arm 142 for engagement with the cam 142 following axial (distal) movement of the needle guard 18. On distally moving the needle guard 18, the engagement surface 146 engages the web 148. This means that the web 148 and the engagement surface 146 are provided to further facilitate the contact between the trigger arm 36 and the plunger arm 142. In a non-shown embodiment, the web 148 can comprise a deflection surface 150 inclined with respect to the trigger arm 36 relative to the axial direction A, i.e., a movement direction of the drive chassis 24. In this connection it should be noted that the deflection surface 150 can be inclined with respect to the axial direction A at an angle selected in the range of 0 to 40°, especially in the range of 5 to 35° and most preferably in the range 10 to 30°.

The engagement surface 146 is also inclined with respect to a movement direction of the drive chassis 24, i.e., with respect to the axial direction A. The engagement surface 146 is inclined to gradually deflect the trigger arm 36 in the direction transverse to the axial direction A of movement of the needle guard 18 in order to shift the trigger arm 36 from the right hand side of the opening 138 of FIG. 8A to the left hand side of the opening 138 of FIG. 8C. In this connection it should be noted that the engagement surface 146 can be inclined with respect to the trigger arm 36 at an angle selected in the range of 5 to 50°, especially in the range of 7 to 30° and most preferably in the range 8 to 20°. In this connection it should be noted that the engagement surface 146 and the web 148 are arranged to face one another in a cooperating manner. When the engagement surface 146 contacts the web 148 respectively the deflection surface 150, the trigger arm 36 is configured to be moved, in particular disengaged, from the stop feature 54, through a deflection in the direction of the arrow B.

The opening 138 at which the stop feature 54 is arranged comprises a surface 152 that has a convex shape. The trigger arm 36 is configured to cooperate with the convex surface 152 of the stop feature 54. For this purpose, the trigger arm 36 comprises a projection 154 engaging the stop feature 54. The projection 154 is configured to cooperate with the opening 138 by engaging into this and by resting on the surface 152 of the stop feature 54 at least in the storage state of the autoinjector 10.

The web 148 is arranged at a surface of the trigger arm 36 different from a surface at which the projection 154 of the trigger arm 36 is arranged. The projection 154 is arranged to project radially from the trigger arm 36, whereas the web 148 is arranged to project transversely from the trigger arm 36.

FIG. 8C shows a state in which the engagement surface 146 of the blocking rib 144 of the plunger arm 142 has moved distally in the axial direction A beyond the axial position of the projection 154, the trigger arm 36 has been deflected in the transverse direction T towards the left hand side of the opening 138 and also radially inwardly in the radial direction R and out of engagement with the stop feature 54.

FIG. 8C shows the state in which the needle guard 18 has been moved distally with respect to the previous figures, i.e., the autoinjector 10 is illustrated in the dispensing state just before the drive spring 74 urges the drive chassis 24 proximally in the axial direction A, as the trigger arm 36 has been released from engagement with the stop feature 54.

Figure 9A:
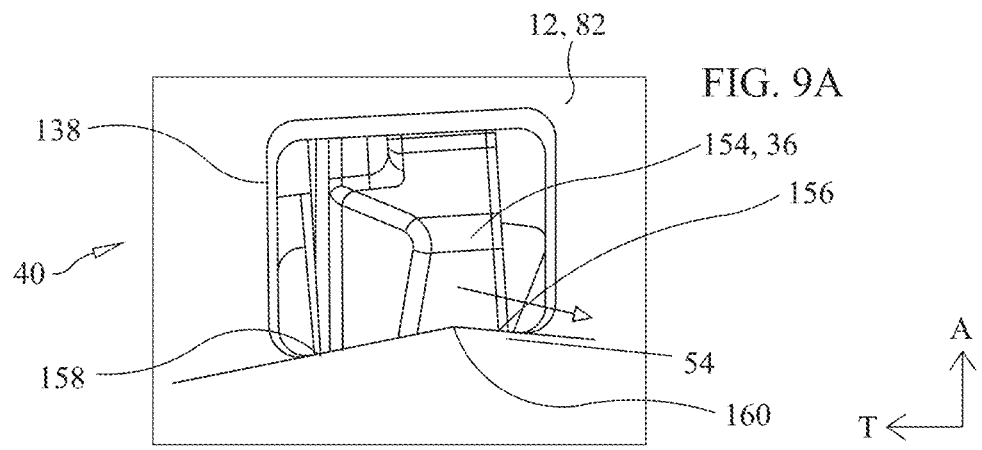
FIG. 9A is a front view of the release mechanism of FIG. 8.

FIG. 9A shows a front view of the opening 138 of FIG. 8B where the projection 154 is arranged at an apex 160 of the surface 152. As discussed in the foregoing, the stop feature 54 comprises the convex surface 152 formed by first and second planar surfaces 156, 158 inclined with respect to one another. The first and second planar surfaces 156, 158 adjoin one another at the apex 160 formed therebetween. In this connection it should be noted that an angle of inclination between the first and second planar surfaces 156, 158 is selected in the range of 110 to 175°, preferably in the range of 120 to 170° and especially in the range of 130 to 165°. In this connection it should further be noted that an angle between the first planar surface 156 and the axial direction A is selected in the range of 0 to 50°, especially in the range of 1 to 30° and most preferably in the range of 2 to 20°. In this connection it should further be noted that an angle between the second planar surface 158 and the axial direction A is selected in the range of −20 to 20°, especially in the range of −10 to 10° and most preferably in the range of −5 to 5°. The apex 160 forms an overhauling angle the trigger arm 36 faces on activation of the autoinjector 10 in order to shift this from the storage state into the dispensing state. In this connection it should be noted that the faces of the trigger arm can preferably be inclined and angled in such a way that the inclination and angle matches the angles and inclinations of the first and second planar surfaces 156, 158. In this way a contact area between the first and second planar surfaces 156, 158 can be maximized providing an improved attachment between the respective surfaces particularly in the storage state.

Figure 9B:
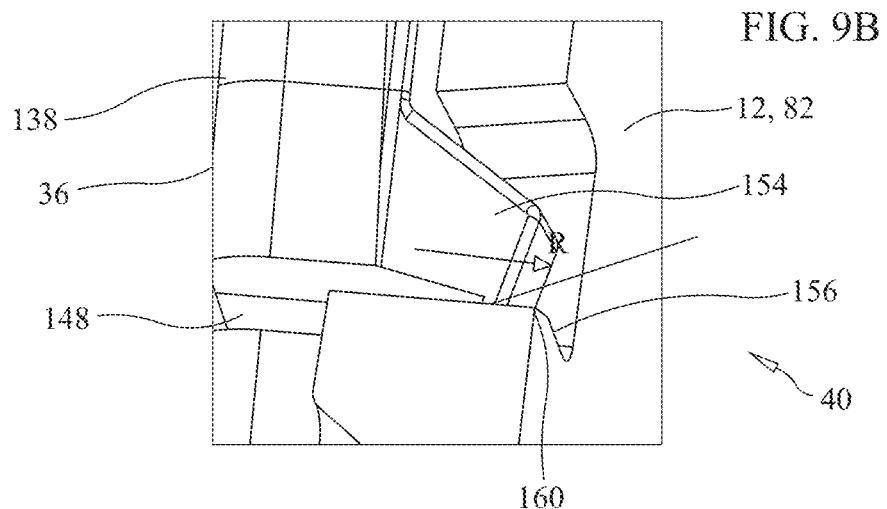
FIG. 9B is a side view of the release mechanism of FIG. 8.
Figure 9C:
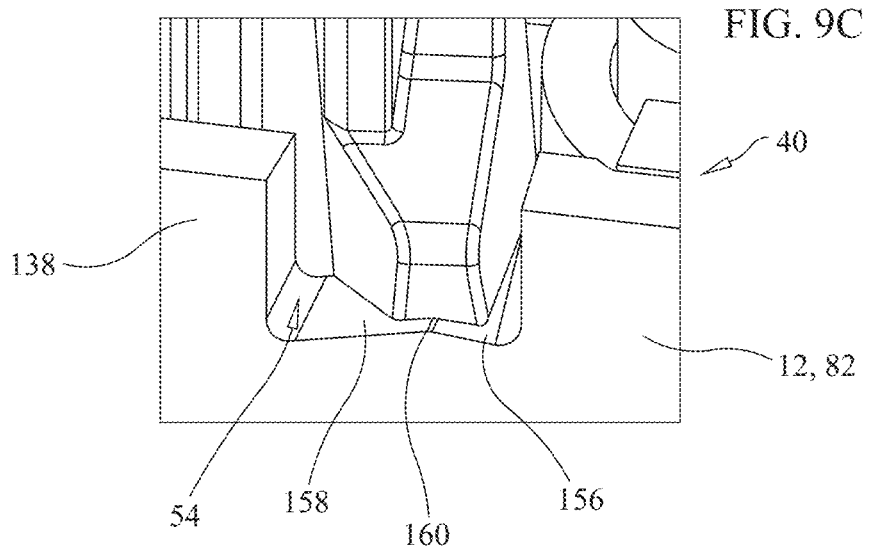
FIG. 9C is a top view of the release mechanism of FIG. 8

FIG. 9A shows a first view of the release mechanism 40 having the trigger arm 36 of FIG. 8 cooperating with the stop feature 54. FIG. 9B shows a second view of the release mechanism 40 and especially the cooperation of the trigger arm 36 with the stop feature 54 in a view perpendicular to that shown in FIG. 9A. In the storage state the blocking rib 144 is configured to block a radial movement of the trigger arm 36, as it forms a wall against which the trigger arm 36 abuts in the event that the trigger arm 36 is urged radially inwardly in a non-permitted manner, e.g., from the outside of the opening 138 when the plunger arm 142 contacts the trigger arm 36.

In this storage state the drive spring 74 urges the drive chassis 24 in the axial direction A and the drive chassis 24 is axially held in position at the opening 138 via the protrusion 154 of the trigger arm 36. More specifically, the protrusion 154 is so to say held in the acute space formed by the first planar surface 156 of the stop feature in the opening, as to move the trigger arm 36, this not only has to be moved in the transverse direction T but also distally in the axial direction A. Once the needle guard 18 is moved towards the drive chassis 24 on moving the autoinjector 10 from the storage state into the dispensing state, the plunger arm 142 via the engagement surface deflects the trigger arm 36, i.e., via the deflection surface 150 of the web 148, both distally in the axial direction A by lifting the web 148 distally in the axial direction A and pushing the web 148 transversely in the transverse direction T. Once the projection 154 of the trigger arm 36 has passed the apex 160, the spring force of the drive spring 74 causes the drive spring 74 to relax and urge the drive chassis 24 proximally in the axial direction A and the trigger arm 36 out of engagement from the opening 138 as indicated e.g., in FIG. 8C or shown in FIG. 4C.

Moreover, once the engagement surface 146 of the plunger arm has deflected the trigger arm 36 in the transverse direction T this can also be deflected radially inwardly in the radial direction R. As is shown in FIG. 4B, this is because the transverse deflection of the trigger arm 36 by the engagement surface 146, moves the trigger arm 36 out of possible engagement from the blocking rib 144 of the plunger arm 142, so that the trigger arm can then also deflect radially inwardly in the radial direction R past the blocking rib 144.

Prior to dispensing, the trigger arm 36 of the drive chassis 24 is biased into engagement with the axial stop feature 54 in the outer body 82 of the housing 12.

Under the action of the axial force from the drive spring 74 on the drive chassis 24, the trigger arm 36 is discouraged from moving either transversely or radially inwards by: the negative inclined contact surface 156 of the outer body 82 of the housing 12, friction acting against them, the angle of the trigger arm 36, and the stiffness of the trigger arm 36. In this connection it should be noted that this geometry may require the drive chassis 24 to be slightly lifted and therefore the drive spring 74 to be slightly compressed in order to disengage the trigger arm 36. However, sufficient robustness (i.e., protection against accidental triggering) can be achieved purely by a combination of the load and frictional coefficient of the surfaces of the stop feature 54 and of the trigger arm 36 in contact. If the frictional coefficient is high enough, even a negatively inclined holding surface (opposite to that shown in the diagram) can be functional.

The blocking rib 144 on the needle guard 18 also prevent the trigger arm 36 from moving radially inwards. It would also be feasible to add further blocking rib features (not shown) to the needle guard to prevent transverse movement of the trigger arm 36. These transverse blocking rib features would be arranged such that, during the initial displacement of the needle guard 18 on actuation, they axially disengage from and release transverse movement of the trigger arm 36.

FIG. 8A shows the storage position of the release mechanism 40 in the storage state. The dispensing process is triggered by pressing the needle guard 18 against the users skin so that it is displaced distally relative to the outer body 82 of the housing 12. The angled engagement surface 146 of the cam 162 of the needle guard 18 contacts the trigger arm 36 and translates its projection 154 transversely over the apex 160 of the stop feature 54 in the outer body 82 of the housing 12. Once the projection 154 of the trigger arm 36 is over the apex 160 of the stop feature 54, it engages with a steeper slope of the second planar surface 158 that, under the action of the drive spring 74, causes the trigger arm 36 to continue to deflect and eventually disengage the stop feature 54 also in the radial direction without further contact from the needle guard 18.

FIG. 8B shows the release mechanism 40 at the point of triggering, in one optional embodiment, after a short transverse movement, the trigger arm 36 contacts the outer body 82 with a further angled face that forces it to move radially inwards until they disengage entirely from the stop feature 54. In an alternative embodiment, the cross-section profile of the trigger arm 36 tends to create a radial movement of the projection 154 (to enable disengagement) when the arm 36 is moved transversely. Once fully disengaged, the drive chassis 24 advances towards the pre-filled syringe 16 to engage the plunger 26 and starts to dispense medicament M under the action of the drive spring 74.

FIG. 8C shows the released position of the release mechanism 40. The overhauling convex surface 152 of the stop feature 54 of the outer body 82 of the housing 12 and the radial lead-in of the trigger arm 36 increases the axial load bearing contact area (which in turn minimizes stress for a given drive spring 74 force) while simultaneously requiring only a short travel to trigger. This short travel to trigger tends to reduce the triggering force input required of the user, with the drive spring 74 actually contributing a large part of the triggering energy.

FIG. 10A shows a view of the position of the needle guard 18 of the autoinjector 10 relative to the inner body 80 of the housing 12 in the storage state of the autoinjector 10. FIG. 10B shows a view of the position of the needle guard 18 of the autoinjector 10 relative to the housing 12 in the lock-out state. The drive chassis 24 is likewise inserted into the inner body 80. The inner body 80 comprises the lug 164 cooperating with the second groove 48' of the drive chassis 24 as the second guiding aid 48 that enables a linear guidance of the drive chassis 24 within the inner body 80 of the housing 12.

The needle guard 18 comprises a protrusion 166 cooperating with an elongate hole 168 present in the inner body 80, to ensure a linear guidance of the needle guard 18 relative to the inner body 80. The needle guard 18 further comprises an anti-pull off feature 170. The anti-pull off feature 170 being configured to prevent a removal of the needle guard from the proximal end of the housing 12. For this purpose, the elongate hole 168 comprises a proximal stop 172 that prevents the protrusion 166 from being moved proximally beyond the stop 172 and hence the stop 172 acts as the anti-pull off feature 170 of the needle guard 18. In this connection it should be noted that the elongate hole 168 is dimensioned such that it is complementary to the shape of the protrusion 166 and such that it defines a linear movement range of the needle guard 16 relative to the inner body 80. This means that a width of the elongate hole 168 perpendicular to the axial direction A can be selected such that it is complementary to a width of the protrusion perpendicular to the axial direction A.

Moreover, a length of the elongate hole 168 between the proximal stop 172 and a distal stop 192 in parallel with the axial direction A can be selected to correspond to a movement range along the axial direction of the needle guard 18. The inner body 80 further comprises a first cut-out 174. The first cut-out 174 being configured to cooperate with a clip arm 184 and a lock-out arm 186 of the needle guard 18. Specifically, as shown in FIG. 10A, the clip arm 184 cooperates with a first portion 180 of the first-cut-out 174 and the lock-out arm 186 is configured to cooperate with a second portion 182 of the first cut-out 174. The first and second portions 180 and 182 of the first cut-out respectively have a rectangular shape, directly adjoin one another and are offset along the axial direction A with respect to one another.

The inner body 80 further comprises a second cut-out 176 that is axially arranged adjacent to the first cut-out 174 and is separated from the first cut-out 174 by a bar 178. The second-cut-out 176 is configured to cooperate with the lock out arm 186. In this connection it should be noted that the second cut-out is configured to only cooperate with the lock-out arm 186, and thus, not with the clip arm 184. This is made possible due to the offset between the first and second portions 180, 182. In this connection it should further be noted that the lock-out arm comprises an engagement portion 220 that is configured to engage a corresponding cut-out 176.

In the embodiment shown, the engagement portion 220 has a ramp 222 via which it can overcome the bar 178 on being moved proximally from the first cut-out 174 to the second cut-out 176 and a planar portion 224 that is configured to drop into the second cut-out 176 and then to act as an abutment that prevents a distal movement of the needle guard 18 out of the lock-out state beyond the bar 178.

As indicated, the first cut-out 174 can be present at the same side of the inner body 80 as the elongate hole 168. The first cut-out 174 can also be present at a side different from the side at which the elongate hole 168 is arranged. It is further possible that two first cut-outs 174 and/or two elongate holes 168 are provided that are then arranged at oppositely disposed sides of the inner body 80 (see e.g., FIG. 14).

As also indicated in FIGS. 10A and 10B, the nose 188 of the connection 72 is present at the inner body 80. The nose 188 cooperates with the window 190 shown e.g., in FIGS. 4A to 4C to form the connection 72.

The function of the needle guard 18 before dispensing is as follows: The needle guard spring, i.e., the lock-out spring 76 (that is biased against the inner body 80) applies a proximal force to the needle guard 18. The needle guard 18 is axially retained within the inner body 80 by its clip arm 184. The needle guard lock-out arm 186 is in clearance to the inner body to avoid long term creep affecting subsequent lock-out robustness.

As the needle guard 18 is pressed during dispensing by the user, the clip arm 184 moves up within the first cut-out 174, more specifically within the first portion 180 of the first cut-out 174, in the inner body 80. Towards the end of the dispensing stroke of the drive chassis 24 (but before an end of dose click (see FIG. 11), to avoid the associated losses occurring at the same time and reducing the minimum output force from the drive chassis 24), the drive chassis 24 contacts a chamfer 226 of the clip arm 184 of the needle guard 18 thereby, deflecting and holding the clip arms 184 radially inwards. The chamfer 226 aids in the deflection of the clip arm 184 in the radial direction R.

Once a user removes the needle 34 and thereby the needle guard 18 from the skin, the needle guard 18 extends linearly proximally under the action of the lock-out spring 76. Because the clip arm 184 is deflected radially inwards by the drive chassis 24, it does not engage with an inner body assembly stop feature 194 during this return travel. Instead, the needle guard 18 continues to extend until its lock-out arm 184 engages with the bar 178 of the inner body 80 in an extended position to lock the needle guard 18 from being able to move in the distal direction.

The bar 178 separates the first cut-out 174 from the second cut-out and the lock out arm 184 is moveable within the first-cut out 174 during use and prior to lock-out of the needle guard 18. Moreover, the protrusion 166 prevents the needle guard 18 from being moved more proximally, in the lock-out state as it engages the proximal end of the elongate hole 168 acting as the anti-pull off feature 170.

FIG. 10B shows the extended position of the needle guard 18 following dispensing and the lock-out clip 186 engages the bar 178. In the fully extended position, the lock-out arm 186 of the needle guard 18 engages with the bar 178 of the inner body 80 to provide a mechanical lockout against depression of the needle guard 18, thus protecting the user from the risk of needle stick.

FIG. 11A shows a view of the autoinjector 10 in the dispensing state at end of dose, and FIG. 11B shows an enlarged view of part of the autoinjector 10 in the dispensing state at the end of dose. The trigger limb 32 further comprises at least a first part 56 of an audible end of dose feedback member 58 in the shape of a click arm 56. The first part 56, i.e., the click arm 56, is formed by a nose 60, optionally having a generally triangular outer shape, formed at an end of a tongue 62, projecting from the trigger limb 32. The tongue 62 projects from the trigger limb 32 in the region of a recess 64 formed in the outer surface 49 of the trigger limb 32. An opening 68 of the recess 64 faces in the radial direction R.

The inner body 80 of the housing 12 further comprises at least a second part 66 of the audible end of dose feedback member 58 (see e.g., FIG. 11B). The second part 66 of the audible end of dose feedback member 58 comprises a distal surface 196 and a proximal surface 198 surrounding an inner body recess 206. In this connection it should be noted that the positioning of the respective first and second parts 56, 66 of the audible feedback member 58 could be reversed, i.e., the recess 206 could be provided at the drive chassis 24, whereas the tongue 62 could be provided at the inner body 80. It should also be noted that each one of the drive chassis 24 and the inner body 80 could comprise a respective first and second part 56, 66 of the audible feedback member 58 which cooperate with a respective other one of the first and second part 56, 66 of the audible feedback member 58 provided at the other component, i.e., the inner body 80 has both a recess and a tongue each cooperating with a respective one of a tongue and a recess at the drive chassis 24.

On use of the autoinjector 10, the trigger limb 32 is moved by the drive spring 74 in the axial direction A during dispensing, the first part 56 of the audible end of dose feedback member 58 is then deflected in the transverse direction T towards the drive spring 74. This is achieved as an inclined surface 200 of the end of dose feedback member 58 is deflected by a distal inner housing end 204 of the inner housing 80. This can be aided as the distal inner housing end 204 can be chamfered towards the distal wall 84 of the housing 12.

The audible end of dose feedback member 58 is configured to emit a sound once the material has been dispensed from the autoinjector, i.e. once a click surface 202 of the nose 60 attached to the latching tongue 62 engages the distal surface 196 of the inner body recess 206 by moving in the transverse direction T outwardly The positions of the first and second parts 56, 66 of the audible feedback member 58 are selected such that the audible click occurs once the plunger 26 reaches or is about to reach its final position in the pre-filled syringe 16. Thereby the audible end of dose feedback member 58 is configured to emit a sound between the drive chassis 24 and the housing 12 once the material has been dispensed from the autoinjector 10. Thus, towards the end of dose, the nose 60 of the drive chassis 24 engages with a ramp of the inner body 80, i.e., the chamfered distal inner housing end 204 which deflects the tongue 62 radially inwards. Near the end of travel, nose 60 drops through the inner housing recess 206 in the inner body 80, rapidly releasing its deformation and creating an audible click (either by virtue of contact with another component surface or purely acceleration in the air).

Figure 12A:
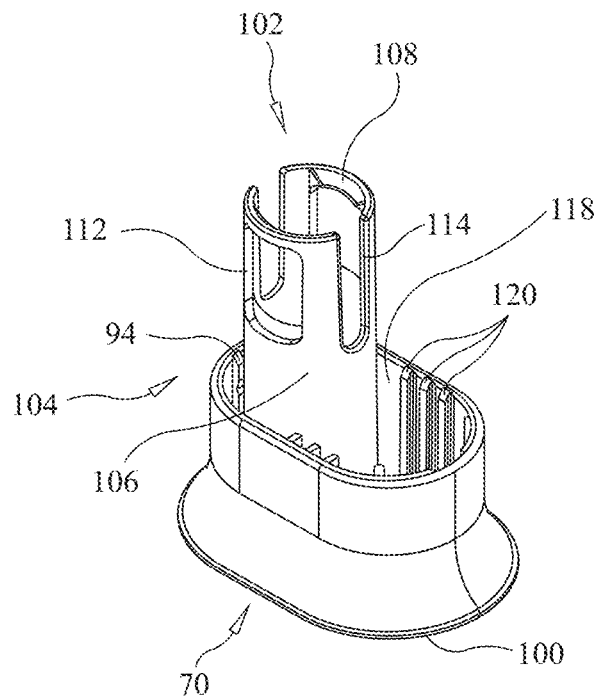
Figure 12B:
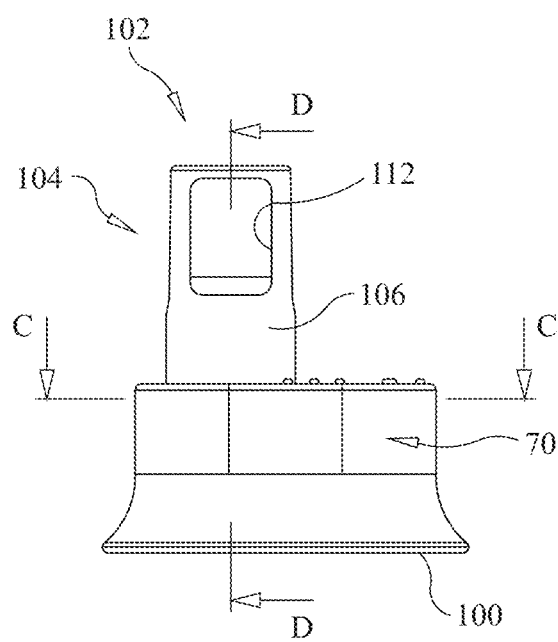
Figure 12C:
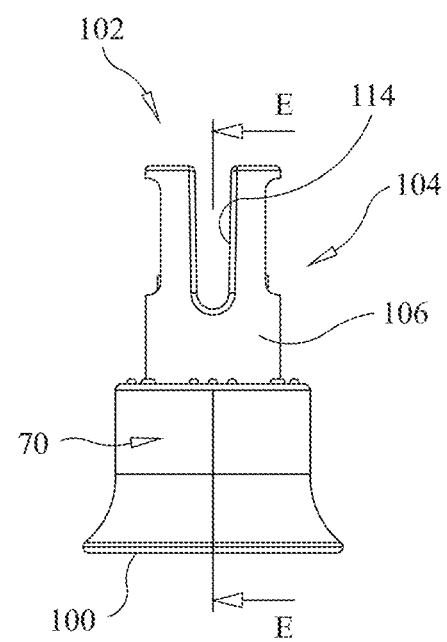

FIGS. 12A to 12F show various views of an example of the cap 70 of the autoinjector 10. FIG. 12A shows a perspective view of the removable cap 70. The cap 70 is of single piece design. The needle guard 18 is configured to cooperate with the cap 70 via one or more snap-fit connections 94. FIGS. 12B and 12C show respective side views of the cap indicating sectional lines C:C, D:D and E:E of the respective sections shown in FIGS. 12D to 12F. The windows 112 shown in FIG. 12B have an at least generally rectangular shape with rounded edges. The recesses 114 shown in the FIG. 12C have the shape of a slot with a rounded end and separate the windows 112. In this connection it should further be noted that the provision of the windows 112 at the needle shield holder 104 also provide a respective tooling lead-in surface that enables ejection of the cap 70 from the injection mold tool. FIG. 12D shows a section through the cap 70 taken along the sectional line C:C of FIG. 12*b*. The ribs 120 are provided at the inner surface 118 of the cap 70 only in a region where the needle shield holder 104 is not present within the cap 70. As indicated in the section shown in FIG. 12E taken along the sectional line D:D of FIG. 12*b*. The space provided within the needle shield holder 104 for receiving and holding the removable needle shield 78 covering the needle of the pre-filled syringe 16 in the storage state of the autoinjector 10 is visible. An inner shape of the needle shield holder 104 is shaped complementary to an outer shape of the removable needle shield 78 to aid an as compact a design as possible of the cap 70 and to permit a reliable removal of the removable needle shield 78 on removing the cap 70 from the autoinjector 10.

Moreover, the opening 124 of the cap 70 is formed between the outer wall 116 of the cap 70 and the needle shield holder 104. The dimensions of the opening are selected in dependence on the dimensions of the part of the needle guard that is to be inserted into the opening in the storage state to the autoinjector 10. The needle shield holder 104 projects distally from the base 100 of the cap 70 and is surrounded by the outer wall 116 of the cap 70. The inner surface 118 of the outer wall 116 of the cap 70 comprises several ribs 120. These ribs are configured to press against the front end 122 of the needle guard 18 when this is arranged within the opening 124.

As indicated in the section shown in FIG. 12F taken along the sectional line E:E of FIG. 12C, the ribs 120 project inwardly into the opening 124 of the cap 70. The ribs 120 are distributed over the inner surface 118 in order to hold the front end 122 of the needle guard 18. The inner wall 106 of the needle shield holder 104 further comprises the two windows 112, with a respective one of the inwardly facing projections 108 being arranged at each of the windows 112. Two recesses 114 are formed in the inner wall 106 of the needle shield holder 104 of the cap 70. The recesses are arranged between respective parts of the needle shield holder 104 having the windows 112. The snap-fit areas 98 of the cap 70 are provided at the inner surface 118 of the cap 70 and a first snap-fit area 208 is formed within some of the ribs 120 of the cap, whereas a second snap in area 210 is formed in a region of the cap 70 free of ribs 120. The cap 70 is of single piece design and an end face in a proximal surface of the cap 70 at the base 100 does not comprise a hole.

FIG. 13A to 13J show various views of an example of the outer body 82 of the autoinjector 10. FIGS. 13A and 13B show respective perspective views from two sides of the outer body 82, whereas FIGS. 13C to 13F show respective side views of the outer body 82, FIG. 13*g* shows a section taken along the sectional line C:C of FIG. 13F, FIG. 13H shows a section taken along the sectional line D:D of FIG. 13E, and FIG. 13I shows a top view of the outer body 82. FIG. 13J shows a section taken along the sectional line E:E of FIG. 13E. The lug 228 configured to engage the second groove 48' forming the second guiding aid 48 is visible a the inner surface 132 of the outer body 82. In contrast to the embodiment shown in connection with the previous figures, the outer body 82 comprises two stop features 54 present at either side of the outer body 82 in the respective windows 40 as indicated in FIGS. 13A, 13C and 13E.

Moreover, the projection 86 projecting from the distal wall 84 of the outer body 82 of the housing 12 is visible in FIG. 13G. It is arranged at the same transverse position as the trigger limb 32 of the drive chassis 24, as it is intended to be inserted into the passage 140 of the drive chassis 24 on assembly of the autoinjector 10.

In this connection it should be noted that the drive chassis 24 is a component that can be configured to move in a straight line within the housing 12 in order to drive the medicament M stored in the pre-filled syringe 16 arranged within the housing 12 out of the pre-filled syringe 16 on activation of the autoinjector 10 by entraining the plunger 26 of the pre-filled syringe 26.

Figure 14A:
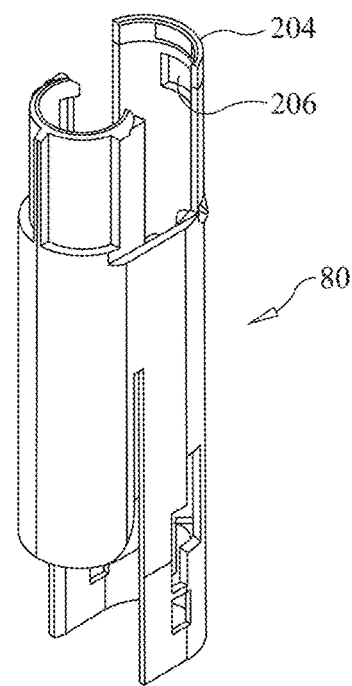
FIGS. 14A to 14J are various views of an example of an inner body of an autoinjector.
Figure 14B:
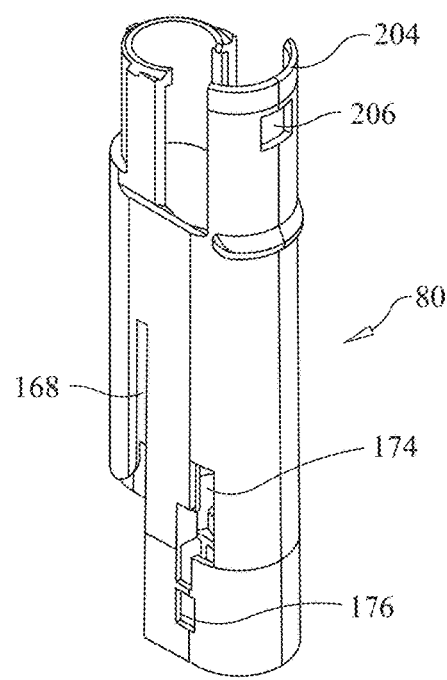
Figure 14C:
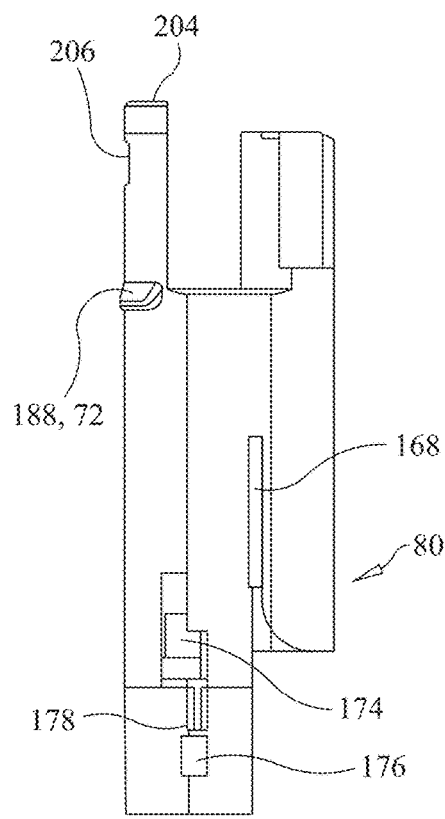
Figure 14D:
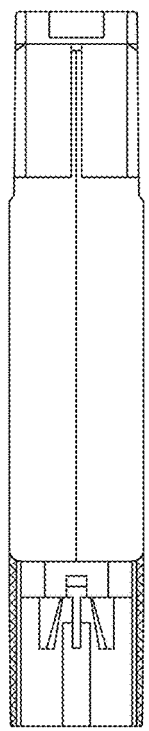
Figure 14E:
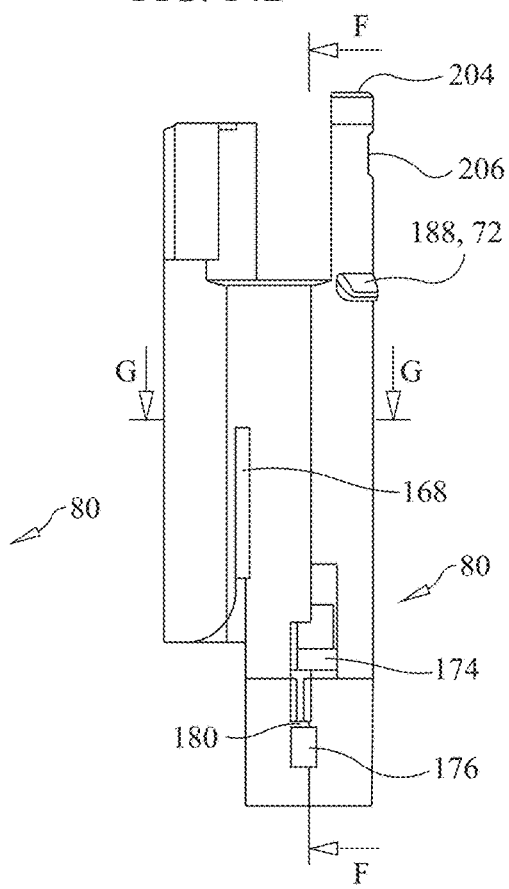
Figure 14F:
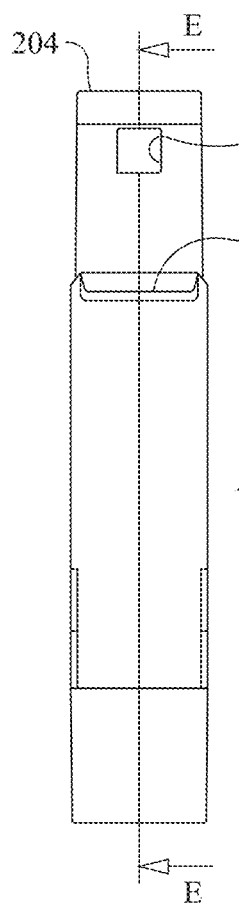
Figure 14G:
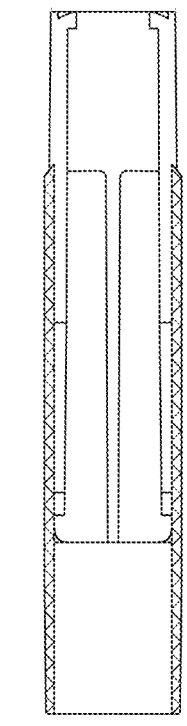
Figure 14H:
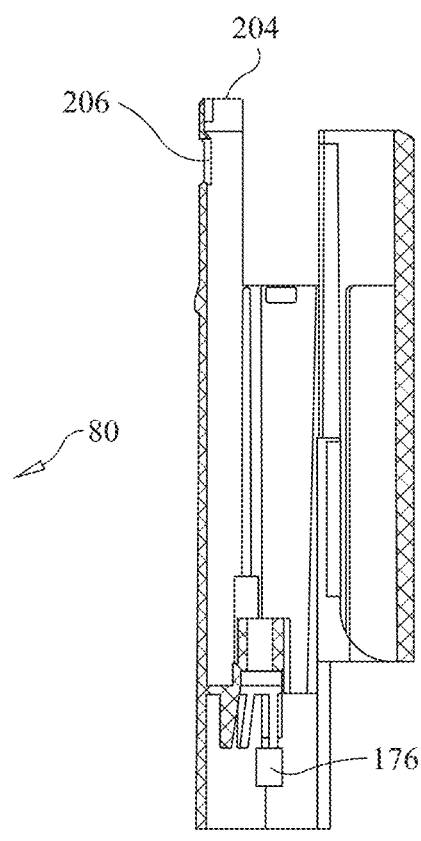
Figure 14I:
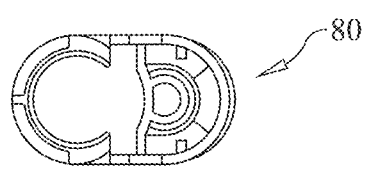
Figure 14J:
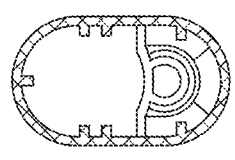

FIG. 14A to 14J show various views of an example of the inner body 80 of the autoinjector 10. FIGS. 14A and 14B show respective perspective views from two sides of the inner body 80. The distal housing end 204 having the recess formed thereat are shown at the top of FIGS. 14 and 14B. FIGS. 14C to 14F show respective side views of the inner body 80. FIG. 14G shows a section taken along the sectional line F:F of FIG. 14E, FIG. 14H shows a section taken along the sectional line E:E of FIG. 14F. FIG. 14I shows a top view of the inner body 80. FIG. 14J shows a section taken along the sectional line G:G of FIG. 14E.

The inner body 80 is configured to cooperate with the outer body 82 of FIG. 13A to 13J and with the needle guard 18 shown in the following in FIGS. 15A to 15J. The inner body 80 has two first cut-outs 174, two second cut-outs 176 and two elongate holes 168 arranged at oppositely disposed sides of the inner body 80 and configured to engage corresponding parts of the needle guard 18.

FIGS. 15A to 15J show various views of an example of the needle guard 18 of the autoinjector 10, it is configured to cooperate with the inner body 80 of FIG. 14, for this purpose it is provided with two protrusions 166 cooperating with a respective one of the elongate holes 168, two lock-out arms 186 cooperating with a respective one of the first and second cut-outs 174, 176 separated by a respective bar 178, and two respective clip-arms 184 engaging the respective first cut-outs 174 and the trigger limb 32 of the drive chassis 24.

Moreover, the needle guard 18 also comprises a single plunger arm 142 having two blocking ribs 144 and two cams shaped in the manner described in the foregoing. The blocking ribs 144 are configured to cooperate with the drive chassis 24 discussed in connection with FIGS. 17A to 17K when inserted into the housing 12 comprising the outer body 82 discussed in connection with FIG. 13 and the inner body 80 discussed in connection with FIGS. 14A to 14J. It should also be noted that the blocking ribs 144 are arranged at opposite sides of the plunger arm 142.

Figure 15A:
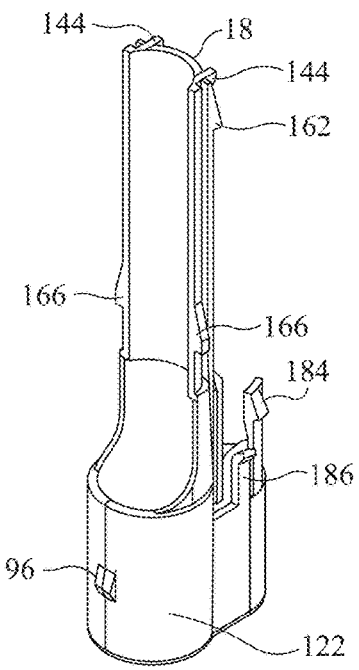
FIGS. 15A to 15J are various views of an example of a needle guard of an autoinjector.
Figure 15B:
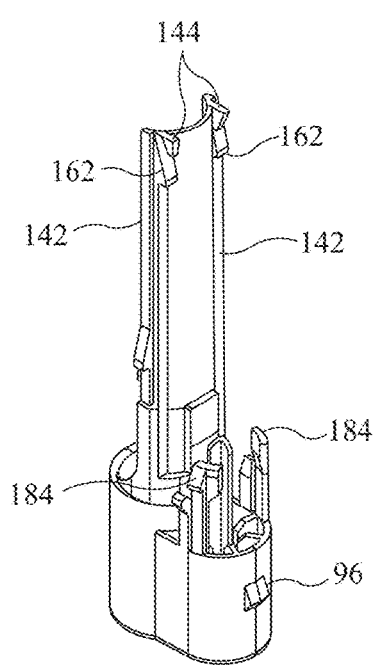
Figure 15C:
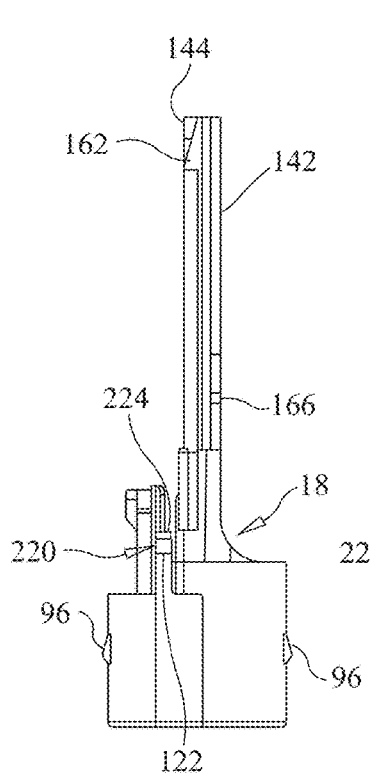
Figure 15D:
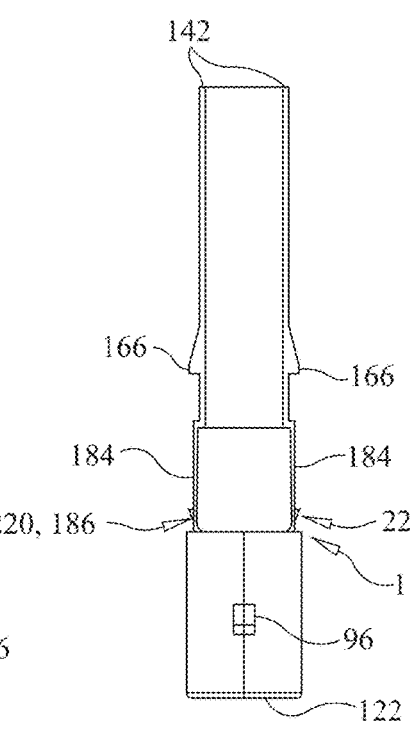
Figure 15E:
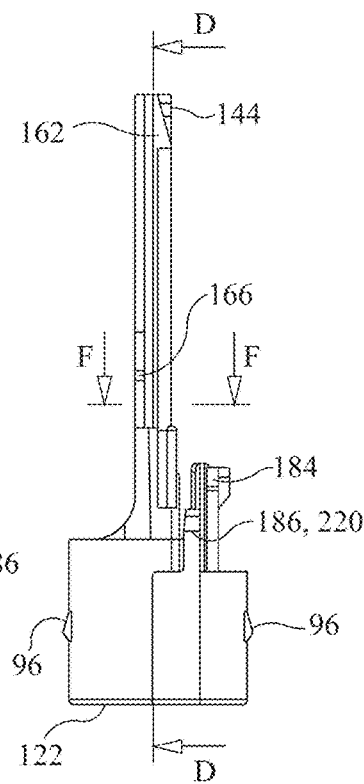
Figure 15F:
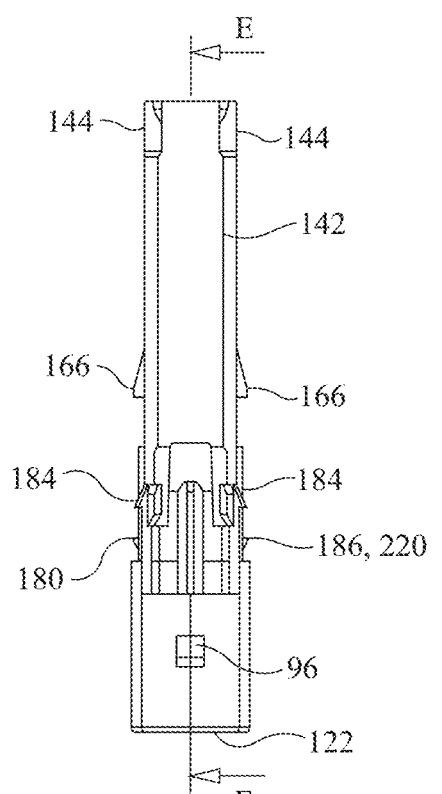
Figure 15G:
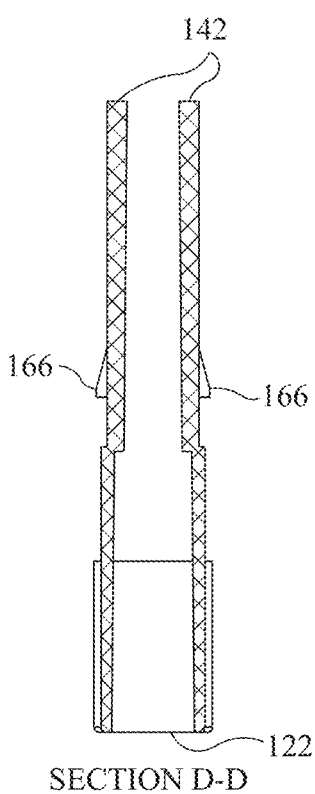
Figure 15H:
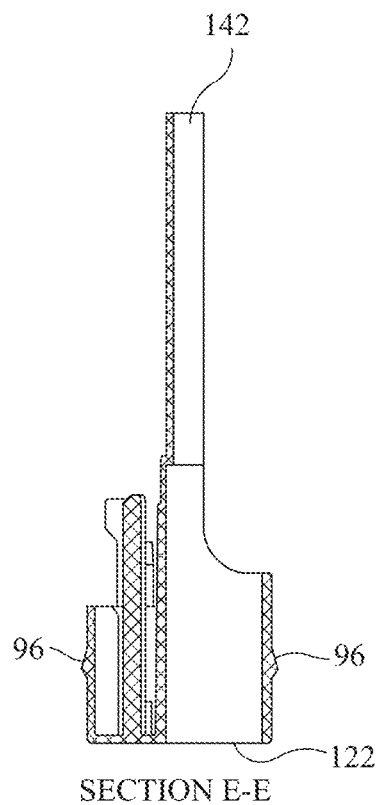
Figure 15I:
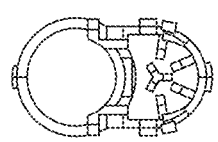
Figure 15J:
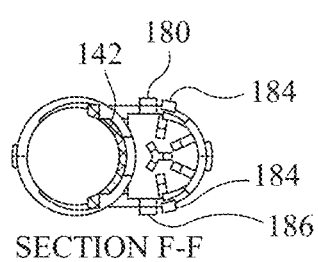

FIGS. 15A and 15B show respective perspective views from two sides of needle guard 18, whereas FIGS. 15C to 15F show respective side views of the needle guard 18. FIG. 15G shows a section taken along the sectional line D:D of FIG. 15E. FIG. 15H shows a section taken along the sectional line E:E of FIG. 15F. FIG. 15I shows a top view of the needle guard 18. FIG. 15J shows a section taken along the sectional line F:F of FIG. 15E.

Figure 16A:
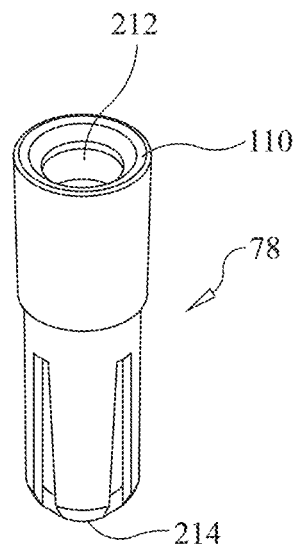
FIGS. 16A to 16K are various views of an example of a needle shield of an autoinjector.
Figure 16B:
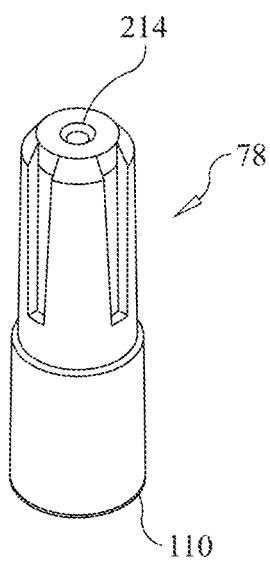
Figure 16C:
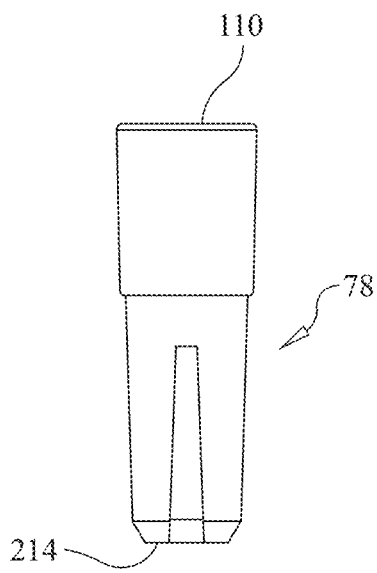
Figure 16D:
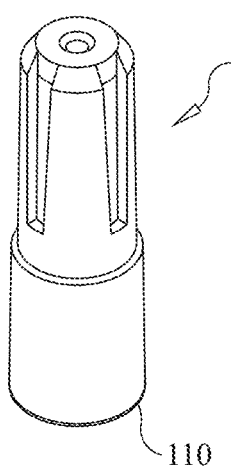
Figure 16E:
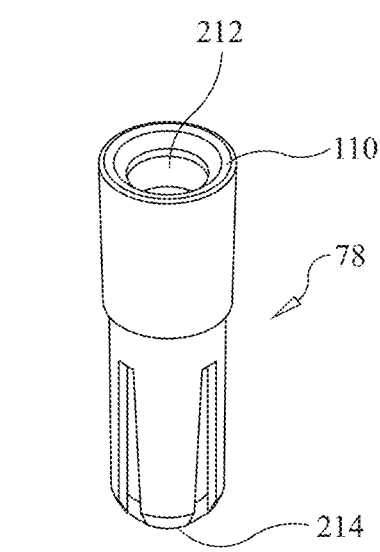
Figure 16F:
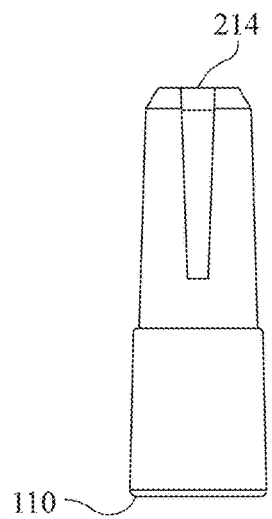
Figure 16G:
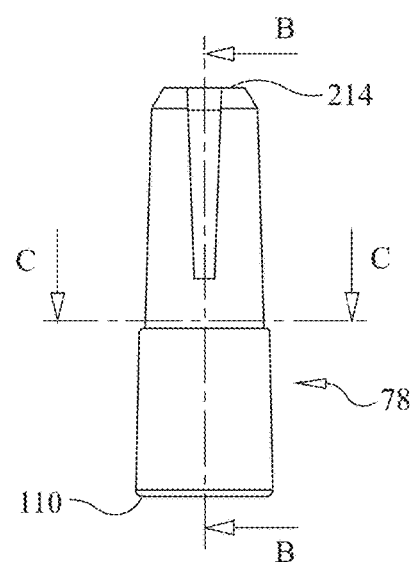
Figure 16H:
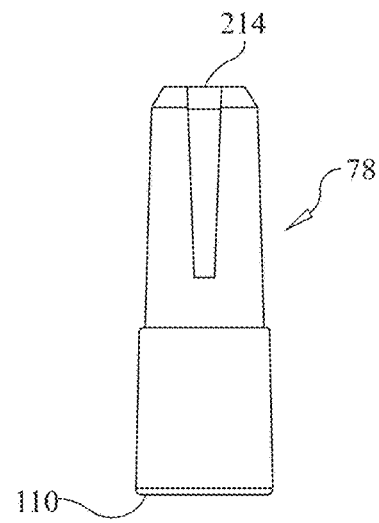
Figure 16I:
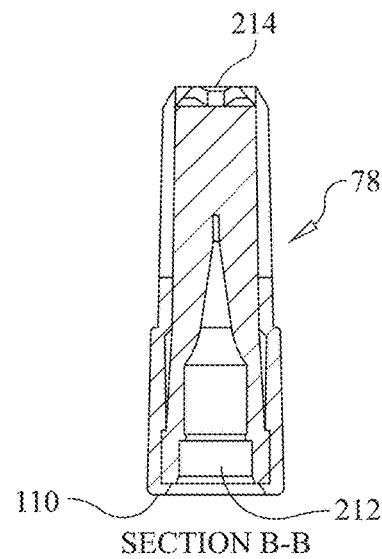
Figure 16J:
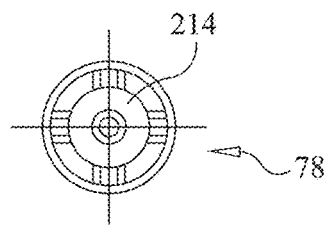
Figure 16K:

FIG. 16A to 16K show various views of an example of the needle shield 78 of the autoinjector 10. The needle shield 78 has a needle receptacle 212 at an end thereof comprising the syringe facing surface 110. The syringe facing surface 110 is arranged opposite to a front end 214 of the needle shield 78. The needle shield 78 has outer dimensions configured to be received in the needle shield holder 104 and inner dimensions adapted to receive the needle 34 of the pre-filled syringe 16. FIGS. 16A, 16B, 16D, 16E show various perspective views from above and below of the needle shield 78, FIG. 16C, 16F, 16G, 16H respective side views of the needle shield 78. FIG. 16I shows a section taken along the sectional line B:B of FIG. 16G, FIG. 16J shows a view from the front end 214. FIG. 16K shows a section taken along the sectional line C:C of FIG. 16G. The section B:B of FIG. 16I indicates that the needle receptacle 212 is shaped complementary to the needle 34 of the pre-filled syringe 16. The function of the needle shield 78 is to protect the needle 34 from external influences.

Figure 17G:
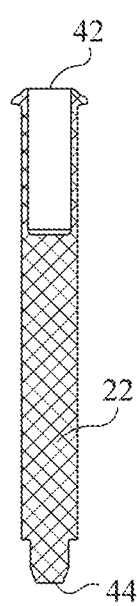
Figure 17H:
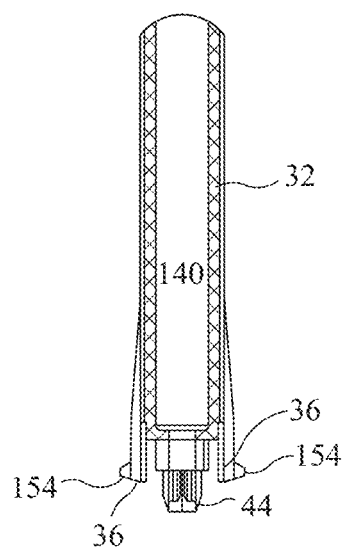
Figure 17I:
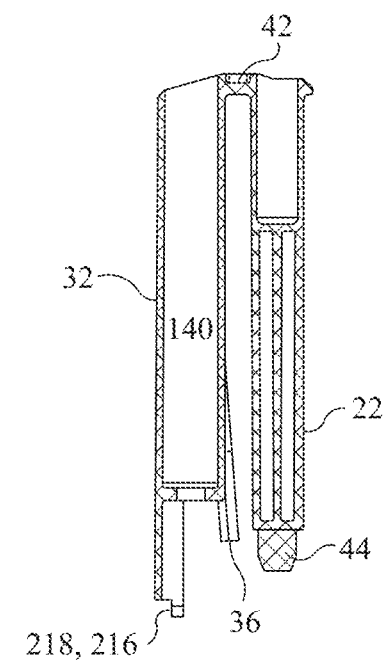
Figure 17J:
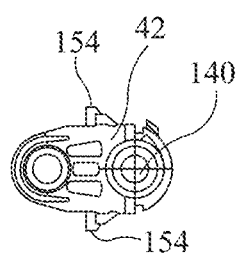
Figure 17K:
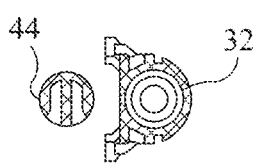
Figure 17L:
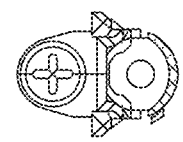

FIG. 17A to 17L show various views of an example of the drive chassis 24 of the autoinjector 10. The drive chassis 24 has two trigger arms 36 each with its respective components as discussed in the foregoing, a single audible feedback member 58 arranged at a side of the drive chassis 24. FIGS. 17A, 17B show perspective views of the drive chassis 24, whereas FIGS. 17C to 17F show different side views of the drive chassis 24. FIG. 17G shows a section taken along the section line E:E of FIG. 17E through the dispensing limb 22 having the plunger support 44. FIG. 17H, shows a section taken along the sectional line F:F of FIG. 17E through the trigger limb 32 indicating the passage 140 formed therein. FIG. 17I shows a section taken along the sectional line G:G of FIG. 17F showing the parallel arrangement of the dispensing limb 22 and the trigger limb 32. FIG. 17J shows a top view of the drive chassis 24 with the projections 154 of the trigger arms 36 projecting radially outwardly from the drive chassis 24. FIG. 17K shows a section taken along the sectional line D:D of FIG. 17E and FIG. 17L shows a section taken along the sectional line C:C of FIG. 17E at a height of the drive chassis 24 where the two projections 154 are positioned relative to the trigger arms 36. FIG. 17D and 17F by way of example show that the trigger limb 32 comprises a lip 216 at an end disposed opposite to the web 42. The lip 216 is configured to engage the clip arms 184 formed at the needle guard 18. The lip 216 comprises two tips 218, with each tip 218 being configured to engage a respective one of the clip arms 184 formed at the needle guard 18. It should also be noted that the first and second guiding aids extend proximally from the web 42, with the second groove 48' extending directly from the web 42 and the first groove 46' begin offset from the web 42.

In the foregoing the mechanism elements of the disposable auto-injector 10 to dispense medicament M from the pre-filled syringe (PFS) 16 are described. The design disclosed permits state of the art features to be incorporated into a small physical package using a very small number of low cost components and a very simple process, compared to the state of the art.

The autoinjector device disclosed comprises an assembly surrounding a pre-filled syringe (PFS) 16 that contains medicament M. Typically, such devices are single-use and intended for administration by a patient (i.e., self-administration) or caregiver.

At point of use, the user removes the protective cap 70 from the proximal end of the autoinjector 10, positions the autoinjector 10 at the injection site (typically the skin of the thigh or belly) and presses the autoinjector 10 axially in a proximal direction, to achieve needle insertion of the needle 34 into the skin and to initiate dispensing. Energy from a helical compression drive spring 74 is released to displace the plunger 26 within the PFS 16 and deliver the medicament M to the patient. An audible click notifies the patient that dispensing has started. In this connection it should be noted that such an audible click can be generated when the trigger arm 36 cooperates with the stop feature 54 on triggering the release mechanism 40 on moving the autoinjector 10 from the storage state to the dispensing state. The progress of dispensing can be monitored by the user as a change in position of the PFS plunger 26 and mechanism plunger within the large wrap-around 'syringe window' 14.

The user is notified when the dose is complete by an audible click emitted from the autoinjector 10 and a change in the color displayed within a unique 'status indicator window' 20. The autoinjector 10 can then be removed from the injection site, allowing the sprung needle guard 18 to extend to a locked position under the action of a separate helical compression spring 76 to cover the needle 34. In this locked position, the needle guard 18 covers the needle 34 and protects the patient or a further person from needle 34 stick injuries.

The mechanism described utilizes a parallel drive arrangement where the axis of the drive spring 74 is offset from the axis of the PFS 16, rather than passing into the bore of the PFS 16 as is common in the prior art. This arrangement has a number of advantages: The length of the autoinjector 10 can be minimized so that it is largely determined by the PFS 16 length and plunger 26 travel. It allows flexibility in the specification of the drive spring 74 (e.g., to increase or reduce the force it applies or make other modifications to improve the efficiency of manufacturing), since its geometry is not constrained by the PFS 16 bore diameter. It allows improved access to components and features, where a tubular arrangement often necessitates a number of concentric (or at least co-axial) components that move relative to each other, which can then be challenging to connect with each other in the optimal way. The improved access further allows simpler interactions between components to create features for triggering, feedback and lock-out which tend to avoid the need for additional parts or complex mechanisms.

The simplicity of the mechanism results in a reduced number of components, which in turn helps to minimize the number of wall thicknesses required and hence device width and depth.

Due to the disposable nature of single-use auto-injectors 10, it is considered advantageous to minimize autoinjector 10 complexity, material usage, package size and assembly complexity in this way, as this all tends to reduce cost and environmental impact by:

reducing the volume of raw materials used,
reducing the cost of manufacturing equipment and the assembly process, and
reducing the volume required in transport and storage, which can be particularly expensive when low temperatures are required.

The disclosed invention achieves this simplicity and small size whilst incorporating state of the art user features and adding innovative new user features.

FIG. 18A to 18E show various views of a further example of the needle guard 18 and the inner body 80 of the housing 12 in different states of use of a further type of autoinjector 10. Like with the previous designs of the autoinjector shown, the needle guard 18 is mounted axially moveable in the housing 12 for movement between a storage state, a dispensing state and a lock-out state in which states the needle guard 18 adopts different axial positions relative to the inner body 80 of the housing 12.

In the following only the differences between the needle guard 18 and the inner body 80 will be discussed. Those parts of the needle guard 18 and the inner body 80 that are shown in the foregoing and not discussed in the following can likewise be provided at the corresponding component.

Figure 18A:
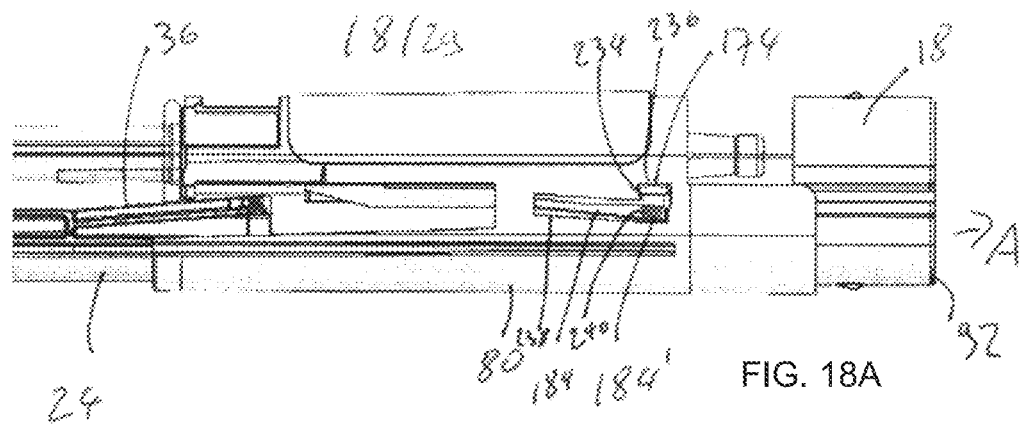
FIGS. 18A to 18E are various views of a further example of the needle guard and the outer body in different states of use.

FIG. 18A shows the needle guard 18 and inner body 80 of the autoinjector 10 prior to use. The one or more clip arms 184 of the needle guard 18 each comprise a block 184' at an end thereof, with the block 184' being configured to engage a lock-out surface 234 of the cut-out 174 in the housing 12 of the autoinjector 10 in the lock-out state. The cut-out 174 is present in the form of a profiled aperture 174' that is at least generally L-shaped respectively is L-shaped, with the lock-out surface being arranged at a short limb 236 of the L-shaped cut-out 174. The lock-out surface 234 is arranged at a short limb 236 at an angle to a long limb 238 of the L-shaped cut-out 174. The short limb 236 and the long limb 238 of the L-shaped cut-out 174 are arranged at an angle to one another, with the angle being selected in the range of 10 to 120°; in particular of 20 to 80°. In the present example the angle between the short limb 236 and the long limb 238 is 65°.

When assembled, the block 184' on the compliant arm (clip arm 184) of the needle guard 18 is located within the profiled aperture 174' of the inner body 80. The radial protrusion of the block 184' from the general form of the compliant arm 184 ensures that the block 184' overlaps the general radial wall thickness of the inner body 80. The block 184' of the clip arm 184 can be positioned such that there is a transverse clearance to the corresponding inner body lock-out surface 234, thus ensuring the lock-out surface 234 and the block 184' cannot engage prior to triggering. The clip arm 184 of the needle guard 18 can be molded to nominally position the block lower than the aperture 174', so that some deformation of the compliant arm 184 is required to achieve this assembled state, and therefore a transverse biasing force exists which holds the block 184' in the position shown.

Figure 18B:
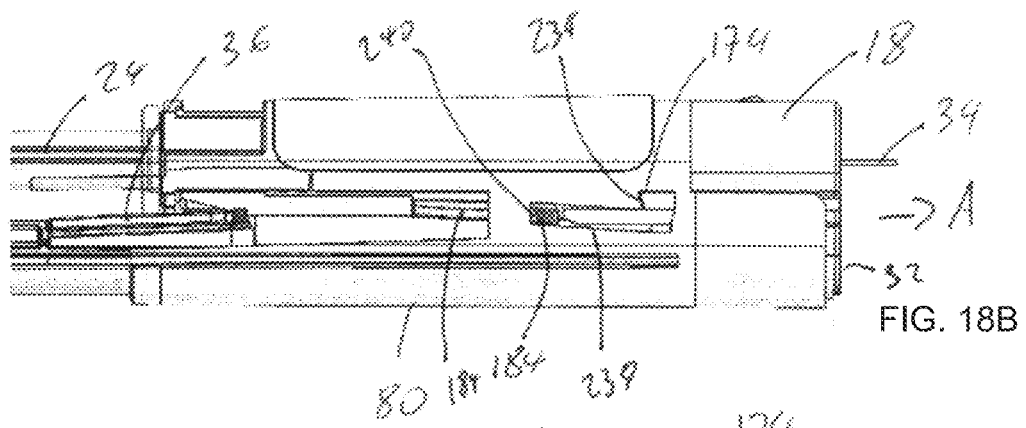

FIG. 18B shows the needle guard 18 and inner body 80 of the autoinjector 10 once the autoinjector 10 is triggered. During use of the autoinjector 10, the needle guard 18 is displaced distally, towards the inner body 18 of the autoinjector 10, as the needle guard 18 contacts the user's skin and the inner body 80 of the autoinjector 10 is moved toward the user's skin. As a dispensing event is initiated, the block 184' moves distally with the general movement of the needle guard 18, so that the block 18 engages with the long limb narrow region of the profiled aperture. This restricts any transverse movement of the block 184' whilst the dispensing event is occurring. The block 184' travels along the long limb 238 of the profiled aperture 174 until full travel of the needle guard 18 is reached, which can be limited by an abutment in another area of the mechanism. Axial movement of the block 184' within the aperture 174 can be unrestricted. Alternatively, it may be preferred to introduce detent features (not shown') within the profiled aperture to provide a specific force feedback profile to the user during axial travel of the needle guard 18.

Figure 18C:
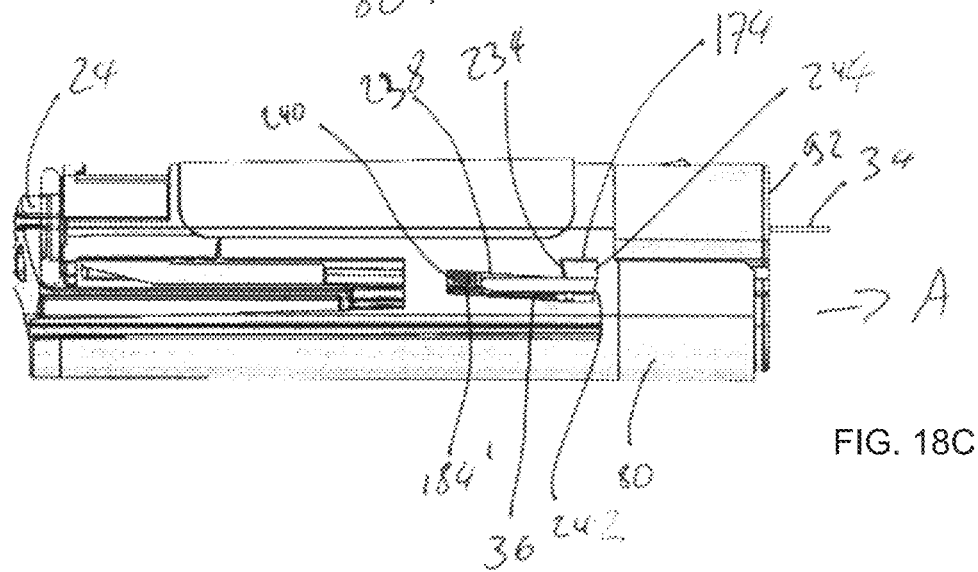

FIG. 18C shows the needle guard 18 and the inner body 80 of the autoinjector 10 once dispensing of the medicament M is complete. As the dispensing event occurs, the drive chassis 24 travels proximally to dispense the medicament M from the PFS 16.

As the drive chassis 24 travels proximally, the trigger arm 36, which is a compliant feature of the drive chassis 24, travels along the inner wall of the outer body 82 and inner body 80, being deflected radially inwards.

As the drive chassis 24 travels in the proximal direction along the axial direction A, contact occurs between the trigger arm 36 and the needle guard 18 in the transverse direction T. Initially this contact may occur with the needle guard 18, which can be considered rigid relative to the stiffness of the compliant trigger arm 36 (i.e., it is the trigger arm 36 that deflects, rather than the needle guard 18).

As the spring chassis 24 travel continues, the trigger arm 36 contacts the compliant arm 184 of the needle guard 18. With the block 18' guided within the long limb 238 of the profiled aperture 174, the block 184' is prevented from being deflected, such that the needle guard compliant arm 184 becomes effectively rigid. The trigger arm 36 therefore continues to be displaced, or is displaced further, in the transverse direction T.

When the drive chassis 24 completes its axial travel, the trigger arm 36 can continue to be transversely deflected due to contact with the needle guard 18. An angled surface is provided on the needle guard, to provide a gradual lead-in as contact with the trigger arm 36 transitions from the block 184' at the end of the compliant arm 184 to the needle guard 18.

The geometry of the needle guard 18 is controlled to provide a smooth and progressive contact surface to the compliant trigger arm 36, so as not to generate force losses which could affect autoinjector 10 function. The compliant arm 184 of the needle guard 18 being built into the needle guard 18 at its distal end disposed opposite of the proximal end 92, and extending in a proximal direction, is advantageous in this respect.

Figure 18D:
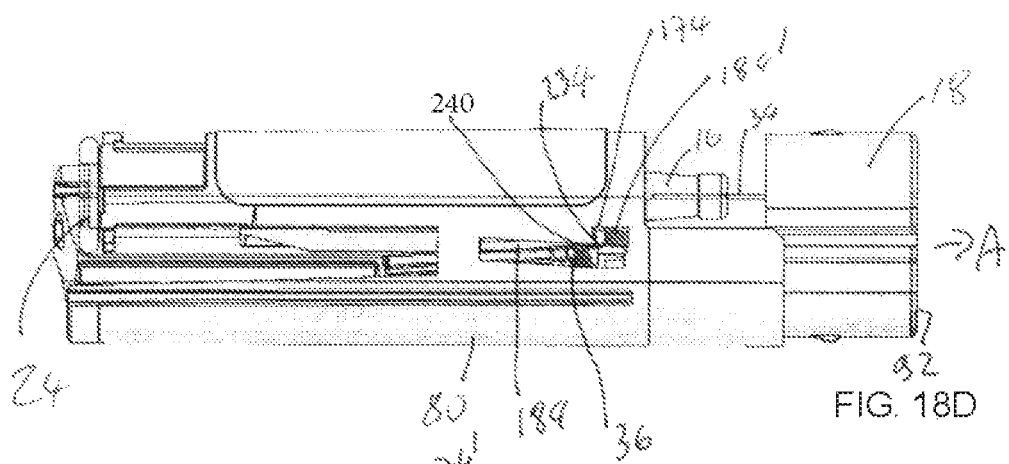

FIG. 18D shows the needle guard 18 and inner body 80 of the autoinjector 10 when the needle guard 18 is locked-out. After the dispensing event, the autoinjector 10 is removed from the user's skin, and the lock out spring 76 of the needle guard 18 applies a force to extend the needle guard 18 in the proximal direction. The block 184' travels proximally along the long limb 238 defined by the profiled aperture 174' in the inner body 80. As the block 184' travels along this path, further transverse deflection of the trigger arm 36 may occur, as the block 184' slides along the surface of the trigger arm 36. The block 184' is biased against an edge of the profiled transverse movement due to the long limb 238 of the aperture 174'.

As the needle guard 18 approaches the end of travel towards its proximal position, the block 184' on the compliant arm 184 of the needle guard 18 passes the lock-out abutment surface 234 of the inner body 80 and becomes axially aligned within the short limb 236 of the profiled aperture 174'. At this point, the biasing force, provided by contact and transverse deflection of the trigger arm 36, is sufficient to deflect the compliant arm 184 and the block 184' of the needle guard 18 into a position located in the short limb 236 of the profiled aperture 174'. The geometry and material of the compliant arms 184 on the needle guard 18 and the drive chassis 24 are specified such that the trigger arm 36 is the stiffer and therefore the majority of the residual deflection occurs within in the compliant arm 184 of the needle guard 18.

Once this state is reached, the raised position of the block 184' creates transverse overlap between a surface 240 of the block 184' and the lock-out abutment surface 234. The needle guard 18 axial position is restricted to minimal movement between the surface 240 of the block 184' and the lock-out abutment surface 234. If the needle guard 18 is biased distally towards the housing 12 of the autoinjector 10, the surface 240 contacts the lock-out abutment surface 234, preventing further distal movement of the needle guard 18.

The surfaces 240, 234 are angled to encourage further engagement of these surfaces 240, 234, via further deflection of the compliant arm 184. In this state, the requirements of needle 34 protection can be met.

The proximal end of the trigger arm 36 may raise to align transversely to the profiled aperture 174' in the inner body 80. If this condition is reached, the end of the trigger arm 36 may move radially outwards, so that the trigger arm 36 becomes transversely restrained by the profiled aperture 174'. This state creates additional robustness, as the trigger arm 36 is locked in this raised state, creating maximum deflection in the compliant arm 184 in the needle guard 18 and maximizing overlap between the surface 240 on the block 184' and the lock-out abutment surface 234 on the inner body 80.

Further protection against high forces resulting from an impact event (autoinjector 10 is dropped) after use are provided by this mechanism. During a drop test the device must be decelerated from its impact velocity. Hence, the kinetic energy of the autoinjector 10 must be absorbed by the structure of the autoinjector 10, predominantly in the form of internal energy (stress & strain). If the distance over which the autoinjector 10 is decelerated can be increased, the forces required to decelerate the autoinjector 10 can be reduced. It is therefore advantageous to increase distance between the impact surface and the surfaces that restrict movement, so that the structural deflections are increased for a given applied load. Thus, A respective one of the one or more trigger arms 36 is configured to engage a respective one of the one or more clip arms 184 on moving the needle guard 18 in the proximal direction between the dispensing state and the lock-out state.

Figure 18E:
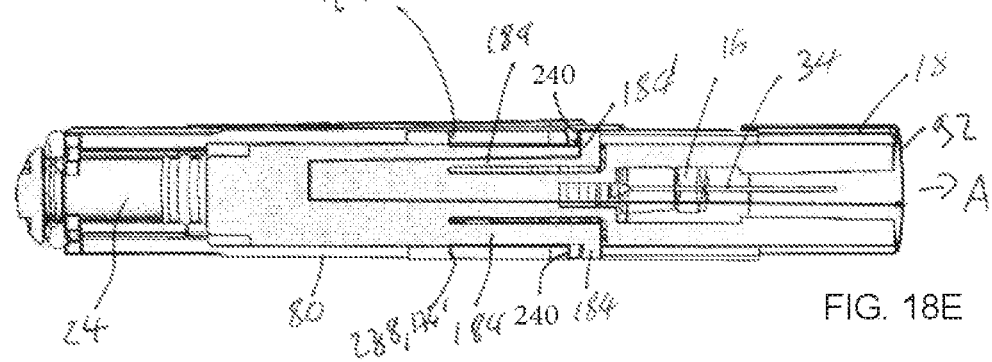
Figure 18F:
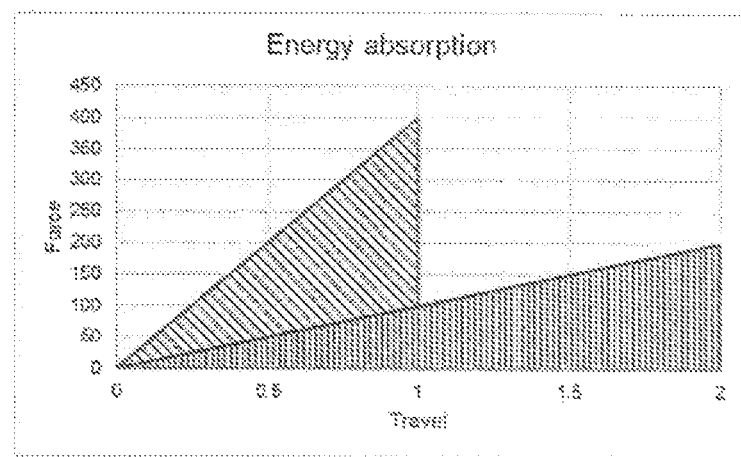
FIG. 18F is a graph showing an area under the curve that represents energy absorbed (both areas and therefore energy absorptions are the same but the peak force is very different)
Figure 20A:
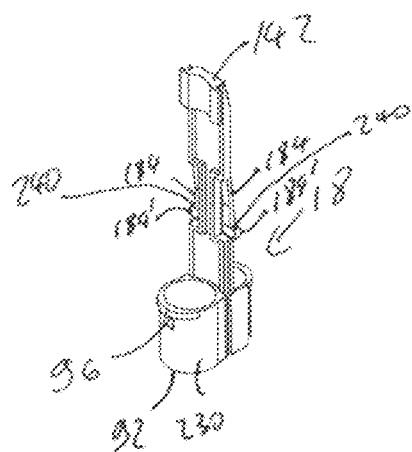
FIGS. 20A to 20J are various views of the needle guard of FIG. 18.
Figure 20B:
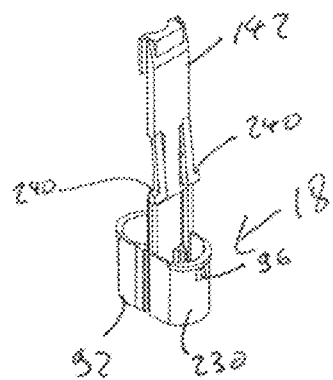
Figure 20C:
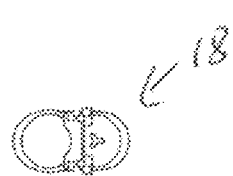
Figure 20D:
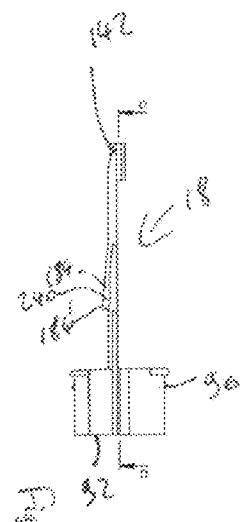
Figure 20E:
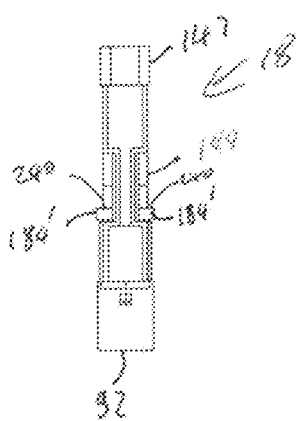
Figure 20F:
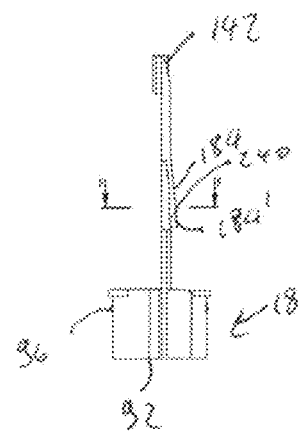
Figure 20G:
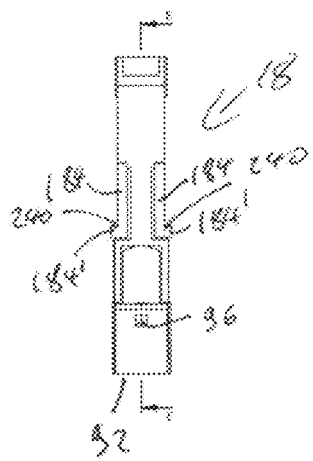
Figure 20H:
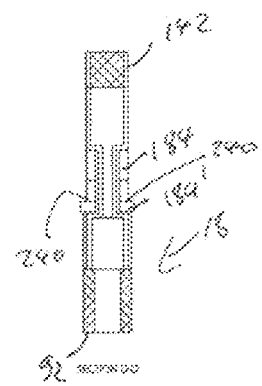
Figure 20I:
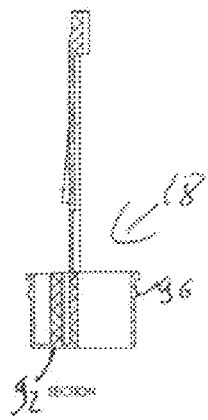
Figure 20J:
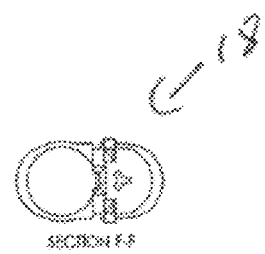

FIG. 18E shows the needle guard 18 and inner body 80 of the autoinjector 10 A load path between impact surface and lock-out abutment is indicated as a length of the long limb 238 of the aperture 174'. FIG. 18F shows an area under a curve that represents energy absorbed (both areas and therefore energy absorptions are the same but the peak force is very different). Hence a higher peak force can be absorbed for shorter distances of travel.

Thus, a means of restricting axial travel of a needle protecting sleeve 230 (see FIGS. 20A to 20J) within an autoinjector 10 are shown, where the needle protecting sleeve 230 returns to a proximal position after the dispensing event and where further distal travel, once this final position is reach, is restricted. The needle guard 18 travel is restricted by axial abutments which occur between the needle guard 18 and the housing 12 of the autoinjector 10. The axial movement of a component that moves during dispensing, is utilized to deflect features on the needle guard 18, to create different abutments after a dispensing event has occurred.

FIG. 19A to 19J show various views of the inner body 80 of FIG. 18. FIGS. 19A and 19B show respective perspective side views of the inner body 80, FIG. 19C shows a top view of the inner body 80, with FIGS. 19D and 19F showing side views of the inner body 80, FIGS. 19E and 19F showing end views of the inner body 80 and FIGS. 19I to 19H showing sectional views of sections indicated in FIGS. 19F and 19G.

The inner body 80 has two profiled apertures 174' as cut-outs 174 incorporated into respective sides of the inner body 80. There can be a single aperture 174', but due to the general symmetry of the device, it may be beneficial to have a similar profiled aperture 174' on both sides of the inner body 80. At the proximal end of the aperture 174', there can be two abutment surfaces 242, 244. There can be an assembly abutment surface 242, which provides the proximal abutment of the needle guard 18 prior to use. There can also be an extended abutment surface 244, which provides the proximal abutment of the needle guard 18 after use. There can be an axial offset between the assembly abutment surface 242 and the extended abutment surface 244. Alternatively, there can be no axial offset between these surfaces 242, 244. These surfaces 242, 244 can be offset in the transverse direction and the transverse width of the aperture 174' at the proximal end may allow unrestricted movement between these abutment surfaces 242, 244 towards the distal end.

The profiled aperture 174' can be narrower in the transverse direction than the transverse width of the aperture 174' towards the proximal end, i.e., along the long limb 238. In particular, the width of the aperture 174' towards the distal end can be matched to the transverse height of the block 184', so that the block 184' follows a defined path as the needle guard 18 travels in the distal direction.

The lock-out abutment surface 234 is arranged at the distal end of the short limb 236 of the aperture 174'. This lock-out abutment surface 234 provides a limit to distal travel of the needle guard 18. The molded geometry described ensures that distal travel of the needle guard 18 is not restricted by this feature prior to use, but is restricted by this feature after a dispensing event has occurred.

FIG. 20A to 20J show various views of the needle guard 18 of FIGS. 18A to 18C. Incorporated along the compliant arm 184 is the block 184', which protrudes radially outwards from the arm 184. This block 184' can be located at the free end of the compliant arm 184, and may provide a limit of travel prior to use in the proximal direction. This block 184' can also provide a limit of travel after use the proximal direction. The features which provides these proximal limits of travel are referred to as the assembly surface 242. After use, a proximal limit of travel is limited by the extended abutment surface 244, whereas the assembly surface 242 limits the proximal travel prior to use. This block 184' can also provide a limit of travel after use in the distal direction, providing a lock-out abutment. The feature which provides the lock-out abutment is referred to as the 'lock-out surface' 234. The one or more clip arms 184 extend in a proximal direction in parallel to the axial direction A from the needle guard 18. The one or more clip arms 184 extend in a proximal direction from the plunger arm 142 of the needle guard 18.

The needle guard 18 comprises a sleeve 230 at the proximal end 92 thereof. The needle guard 18 is of at least generally T-shaped design, with the plunger arm 142 being arranged in parallel to the axial direction A of the autoinjector 10 from the proximal end 92 to a distal end of the sleeve 230. The sleeve 230 comprises one or more elongate slots 232 extending in parallel to 25 the axial direction A of the autoinjector 10 from a proximal end to a distal end of the sleeve 230 .

This further type of needle guard 18 and the inner body 80 describe a mechanism to control the limits of travel of the needle guard 18 of the disposable autoinjector 10 30 used to dispense the medicament from the pre-filled syringe 16. The mechanism disclosed permits full distal travel of the needle guard 18 to occur during initial use of the auto-injector, when a dispensing event is initiated. After the dispensing event has occurred and the autoinjector 10 has been removed from the injection site, the mechanism allows the needle guard 18 to travel to a final proximal position. Once in the final position, the needle guard 18 is locked out to prevent further distal travel. This lock is intended to withstand sufficient axial force to provide the required protection from the needle 34, even in the event of an impact resulting from dropping the autoinjector 10.

The drive chassis 24 described in connection with the foregoing types of autoinjectors 10 can be used with the inner body 80 and the needle guard 18 and utilizes the displacement of the Drive Chassis, which occurs during a dispensing event, to provide the lock-out once the final position is reached. The forces required to axially displace the needle guard 18 into the final position are designed to be low, allowing the force output of the lock-out spring 76 to be minimized. This helps to achieve desirable low triggering forces, as the user must compress this spring 76 to operate the autoinjector 10.

When in the final position following dispensing, the needle guard 18 achieves the lock-out, which must react sufficient force over sufficient travel to absorb the kinetic energy of the autoinjector 10 in an impact event. The mechanism provides an extended load path along the full length of the needle guard 18 and back along its compliant features and provides additional radial support of the compliant features to achieve both a high reaction load and a high displacement whilst loaded. Both of these combine to provide a large energy absorption capability, enabling the autoinjector 10 to better withstand impact events.

The mechanism requires no additional parts to be added to the autoinjector 10 described in FIGS. 1A to 20J. The features described can be incorporated into existing components, whilst maintaining the existing injection mold tool strategies and the existing assembly sequence.

Figure 21:
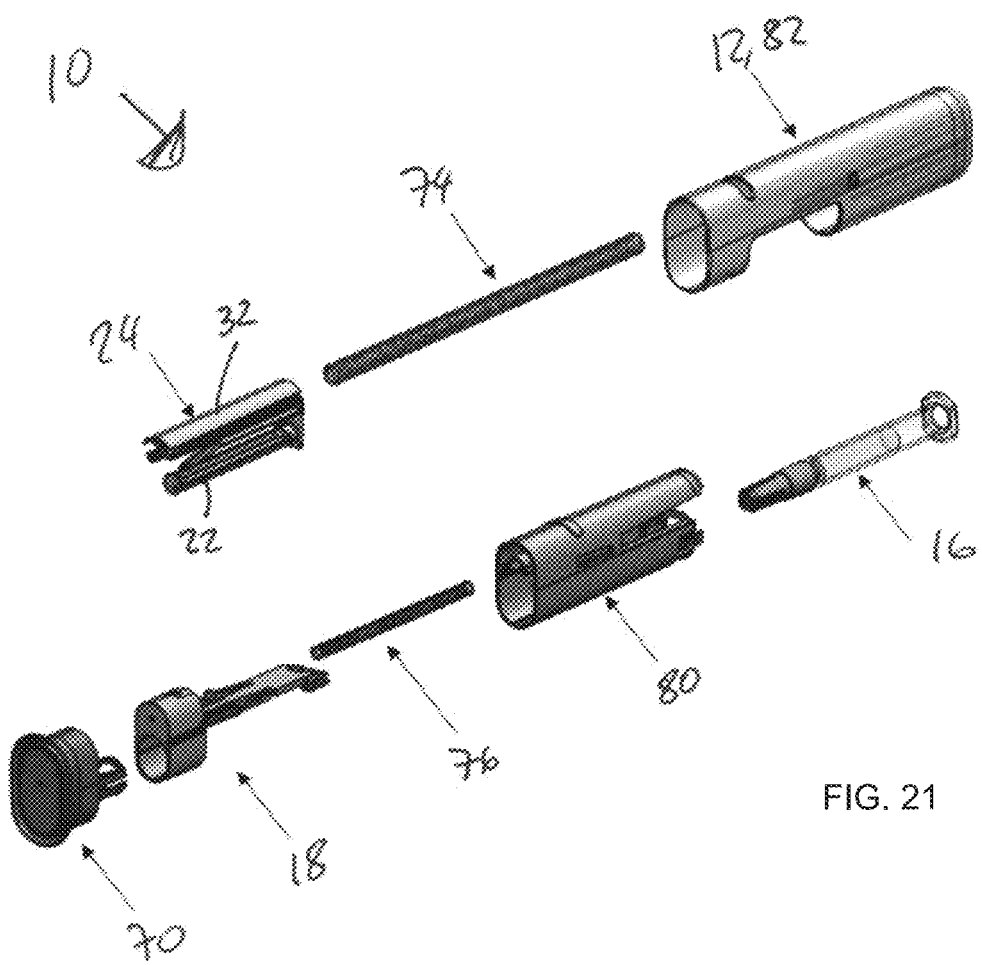
FIG. 21 is an exploded view of components of further kind of autoinjector.

FIG. 21 shows an exploded view of components of further kind of autoinjector 10. The autoinjector 10 comprises the drive chassis 24, the drive spring 74, the inner body 80, the outer body 82, the cap 70, the needle guard 18, the needle guard spring 76 and the pre-filled syringe 16.

Figure 22:
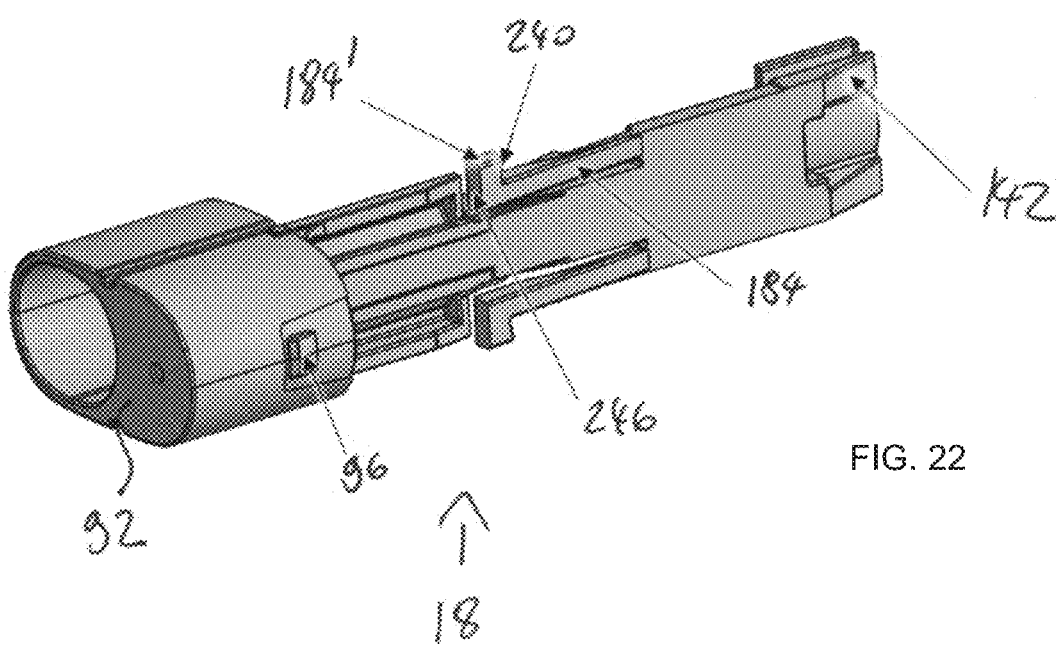
FIG. 22 is a perspective view of a needle guard of the autoinjector of FIG. 21.

FIG. 22 shows a perspective view of the needle guard 18 of the autoinjector 10 of FIG. 21. The needle guard is similar in design to that shown in connection with FIG. 20. The needle guard 18 comprises two clip arms 184 each having a respective block 184' that acts as a lockout block feature at the end of each of the two clip arms 184. The end surface of the respective clip arm 184 and of the block 184' is known as an assembly stop feature 246. On reaching the lock-out state the assembly stop feature 246 abuts the assembly abutment surface 242 of the inner body 80 as is shown e.g., in connection with FIG. 31. The clip arms 184 on the needle guard 18 are biased against the inside end face of the aperture 174' in the inner body 80 to provide a stop limiting the travel of the needle guard 18 relative to the housing 12.

Figure 23:
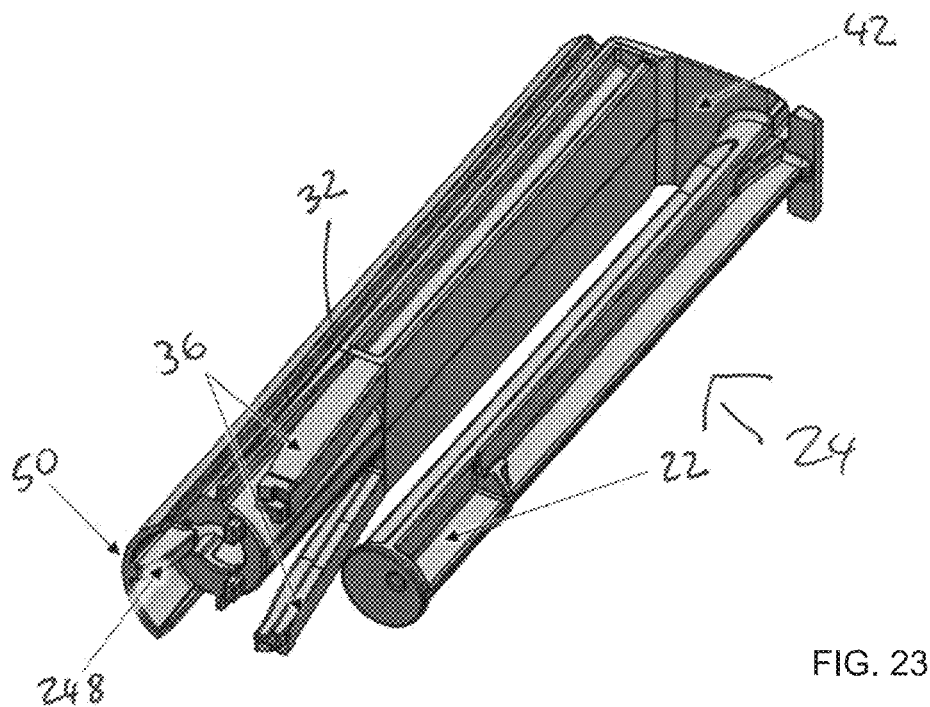
FIG. 23 is a perspective view of a drive chassis of the autoinjector of FIG. 21.

FIG. 23 shows a perspective view of the drive chassis 24 of the autoinjector of FIG. 21. The principal difference is that an end of dose ramp 248 is provided at the trigger limb 32. The end of dose ramp 248 is configured to cooperate with an end of dose click arm 250 present on an inner surface of the inner body 80 as is visible in FIG. 24B. Towards the end of dose (EoD), the EoD click arm 250 of the inner body 80 engages with the EoD ramp 248 on the drive chassis 24 which deflects the EoD arm 250 transversely towards the center of the device. The EoD click arm 250 passes through the proximal end of the drive chassis 24 and drops off the end of the EoD ramp 248, rapidly releasing its stored energy and creating an audible click. In this connection it should be noted that the click will always occur before the device reaches the 'Fully Dispensed-Rigid Stopper' condition, i.e., the position in which the plunger 26 can no longer move within the pre-filled syringe 16. The EoD ramp 248 is arranged at the same or approximately the same axial position as a proximal end of the trigger arm 36 and of the first part outer surface 50 of the trigger limb 32.

It should further be noted that the web 42 also improves a damping function within the autoinjector 10. This is because when the drive chassis 24 impacts the plunger 26 during triggering of a dose, a large amount of energy is transferred to the syringe 16. If the load path is stiff, this can result in very high forces being applied to the flange of the syringe 16, causing it to break. The web 42 connecting the dispensing limb 22 to the trigger limb 32 provides a compliance between these two limbs 22, 32 which essentially reduces the force applied to the syringe flange during triggering of a dose.

Figures 24A, 24B:
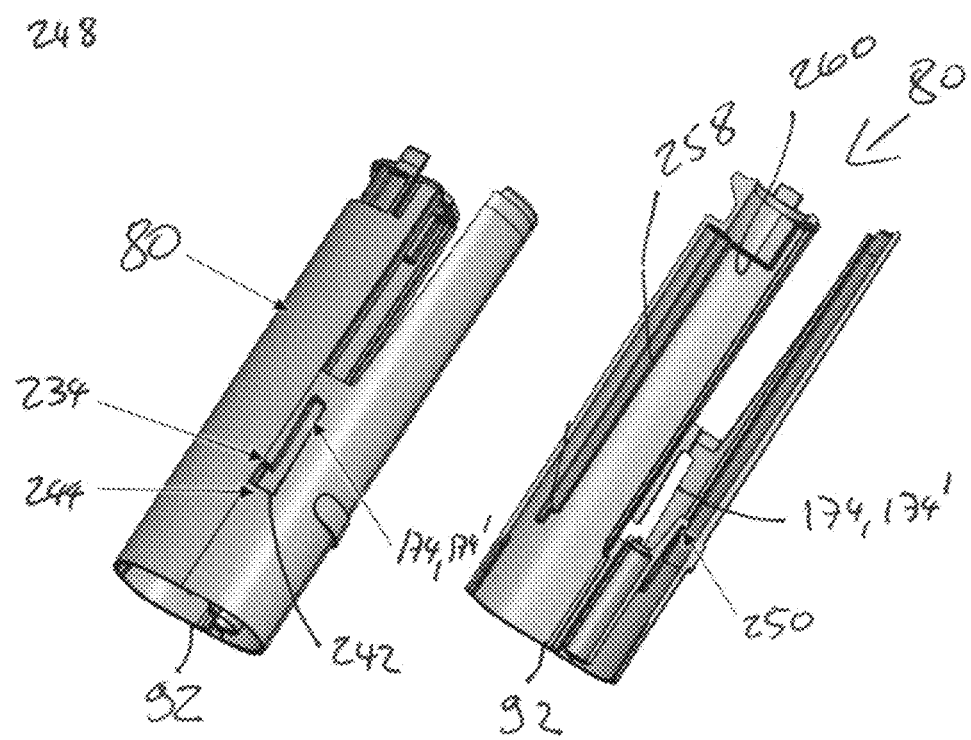
FIGS. 24A and 24B are perspective views of an inner body of the autoinjector of FIG. 21.

FIG. 24A shows a perspective view of the inner body 80 of the autoinjector 10 of FIG. 21, with FIG. 24B showing a perspective part sectional view of the interior of the inner body 80 showing the position of the EoD click arm 250. This is arranged at approximately 30% of a length of the inner body 80 from the proximal end 92. In this connection it should be noted that the EoD click arm 250 can be arranged at an axial height of the inner body 80 within the inner body 80 ranging from 10% to 50%, preferably from 20 to 40%, of a length of the inner body 80 from the proximal end 92. Providing the end of dose click in the manner described above using a click arm 250 cooperating with a ramp 248 results in a louder click in comparison to the design shown e.g., in FIGS. 11A and 11B using a nose. This has the advantage of reducing the free play between the components, increasing the amount of deflection that is possible and moving the features that click away from the outside surface (so that they are less likely to be damped by the users hands).

Figures 25A, 25B, 25C:
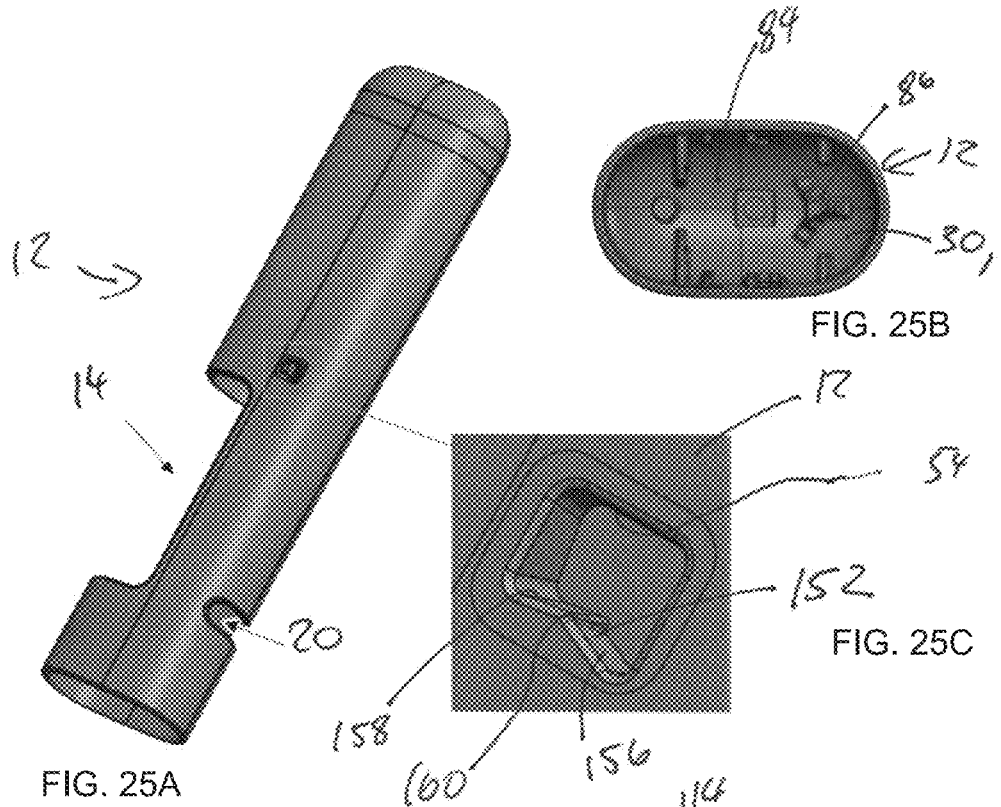
FIGS. 25A to 25C are views of an outer body of the autoinjector of FIG. 21.

FIG. 25A to 25C show views of the outer body 82 of the autoinjector 10 of FIG. 21 that is configured to cooperate with the components of the autoinjector 10 show in FIG. 21. In contrast to the outer body 82 shown e.g., in FIGS. 1A and 1B, a proximal position of the syringe window 14 and of the status indicator window 20 is the same or at least approximately the same for the outer body 82 of FIG. 25A. Moving the status indicator window 20 downwards, i.e., towards the proximal end makes the autoinjector 10 more diversely useable, as the number of components that must change to accommodate different PFS 16 fill volumes can be reduced. This also has the effect that the drive chassis 24 will not appear behind the window in the pre-dispensing condition, i.e., prior to activation of the autoinjector 10 a part is not visible in the status indicator window 20 that is subsequently visible. It is possible in this connection to texture the status indicator window 20 so that the internal mechanism is obscured when the drive chassis 24 is at the distal end of the outer body 82 and hence not visible in the status indicator window 20. When the dispensing is finished, the drive chassis 24 will appear behind the status indicator window 20 and should flood it with color. Only showing the drive chassis 24 in one state (the 'dispensing complete' state) has the advantage that the drive chassis 24 does not have to be printed on its outer surface 49 as it only appears once.

FIG. 25B shows the projection 86 of the distal wall 84 of the outer body 82. The projection 86 has a pointed end formed by three surfaces merging into the pointed end. The projection 86 is formed such that it is journaled by the drive spring 74 on use of the autoinjector 10. In this connection it should be noted that the projection 86 shown in FIG. 26B has a length that is longer than the length of the projection shown in FIG. 25B. It should further be noted that a length of the projection can be selected in the range of 5% to 50% of a length of the outer body 82, preferably in the range of 10% to 40% of a length of the outer body 82.

Figure 26:
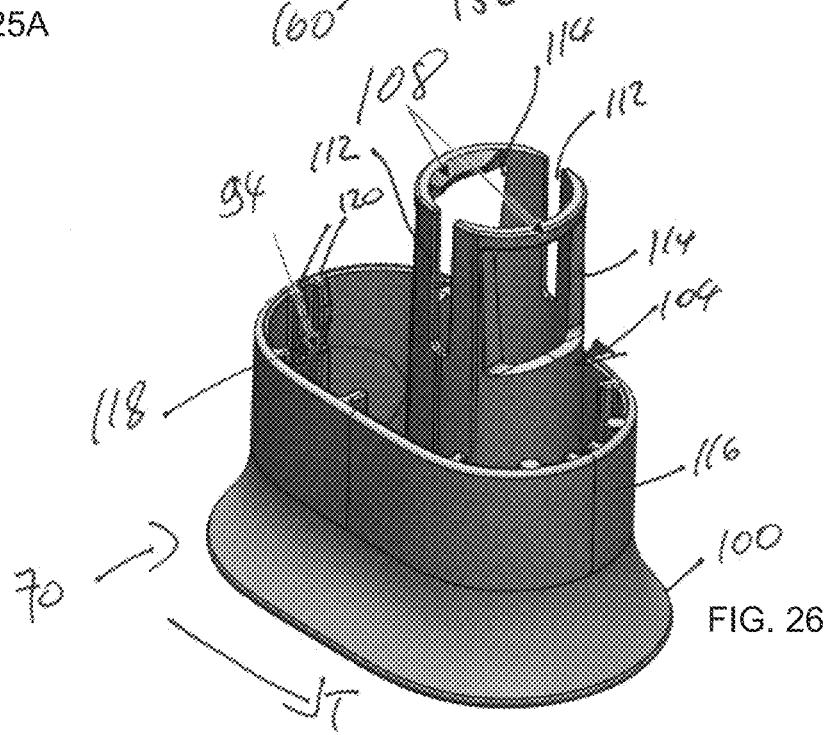
FIG. 26 is a perspective view of a cap of the autoinjector of FIG. 21.
Figure 27A:
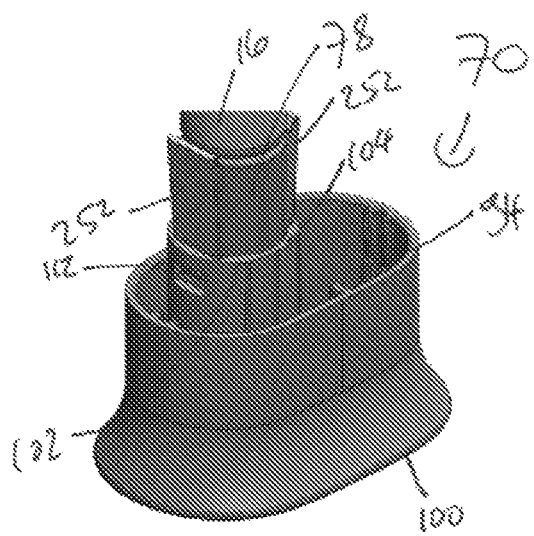
FIGS. 27A to 27D are various views of a further kind of cap.
Figure 27B:
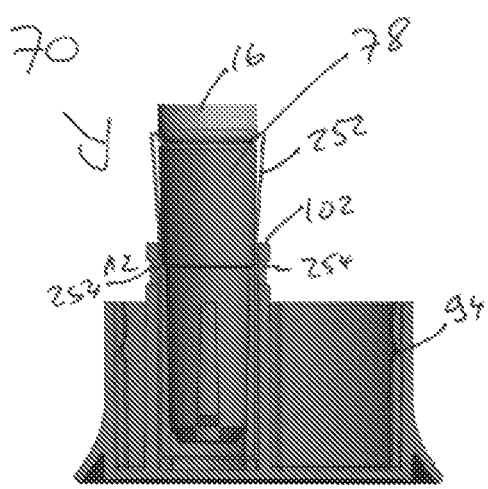
Figure 27C:
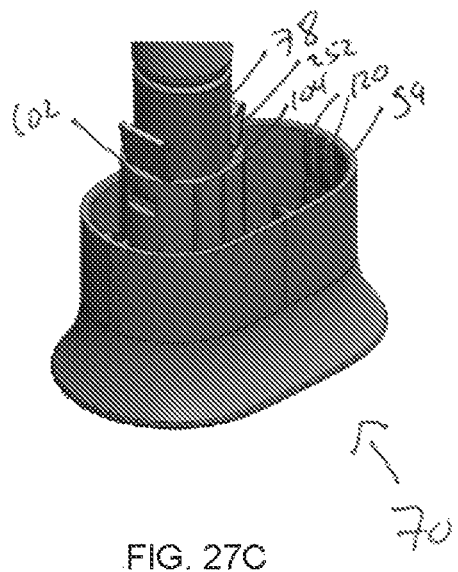
Figure 27D:
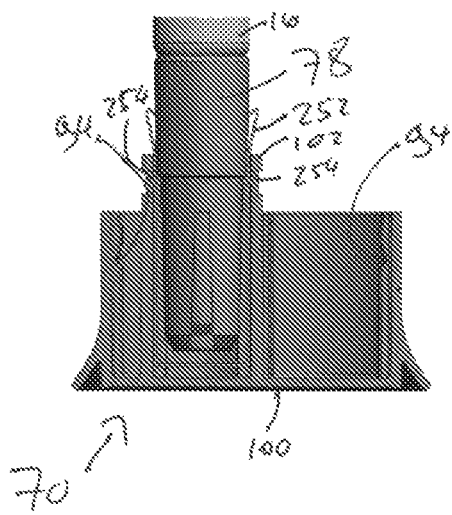

Also visible is the convex surface 152 of the stop feature 54 in FIG. 25C. The convex surface 152 is formed by the two planar surfaces 156, 158 that merge at the apex 160. FIG. 26 shows a perspective view of the cap 70 of the autoinjector of FIG. 21. The cap is configured similar to the cap 70 shown e.g., in FIG. 25A. The difference lying in the position of the recesses 114 that are arranged between the two windows 112. In FIG. 25A the recesses 114 are arranged in parallel to the transverse direction T whereas in FIG. 26 they are arranged perpendicular to the transverse direction T. It should further be noted that the inner surface 118 of the outer wall 116 of the cap 70 comprises two ribs 120 at each longitudinal side, whereas the cap 70 shown in FIG. 5A comprises three such ribs 120 at each side.

FIGS. 27A to 27D show various views of further kinds of cap 70. A clip 252 is provided for the kind of cap 70 shown in FIG. 27A and 27B that engages a distal end of the removable needle shield 78. On the other hand, in the cap 70 shown in FIGS. 27C and 27D, the clip 252 is configured to engage side walls of the removable needle shield 78. In each case, the needle shield holder 104 has two windows 112 of reduced size in comparison to the cap 70 shown e.g., in connection with FIG. 4A and has no recesses 114 between the windows 112. The windows 112 and the needle shield holder 104 are respectively configured to hold the clip 252 in place, with the clip 252 in turn being configured to remove the removable needle shield 78 on removal of the cap 70 from the autoinjector 10. For this purpose, the clip 252 comprises barbs 254 that engage the respective windows 112.

As also indicated the free end of the clip 252 facing the removable needle shield 78 is configured to exert a pressure on the removable needle shield 78 such that on removal of the cap 70 the removable needle shield 78 is automatically also removed.

Figure 28A:
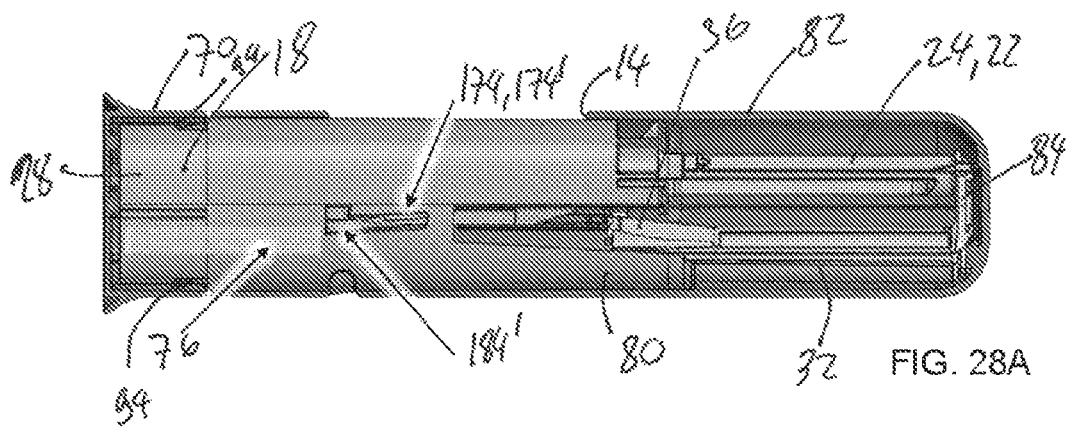
FIGS. 28A to 28C are various views of the autoinjector of FIG. 21 in a storage state.
Figure 28B:
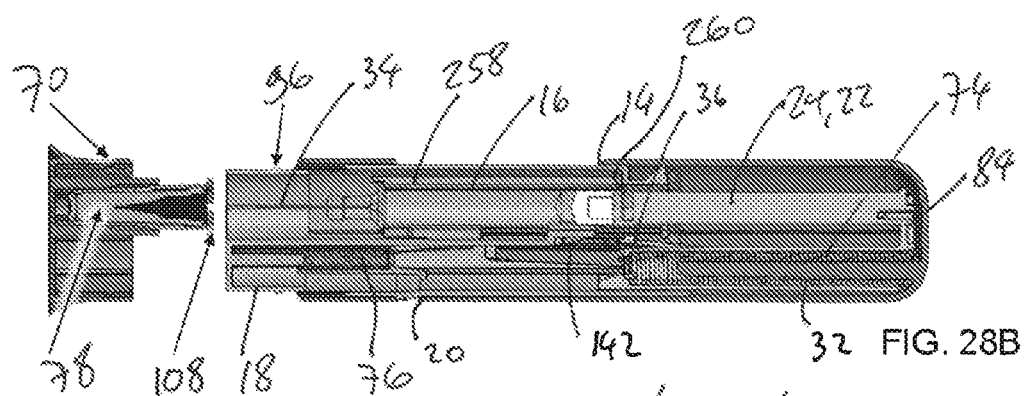
Figure 28C:
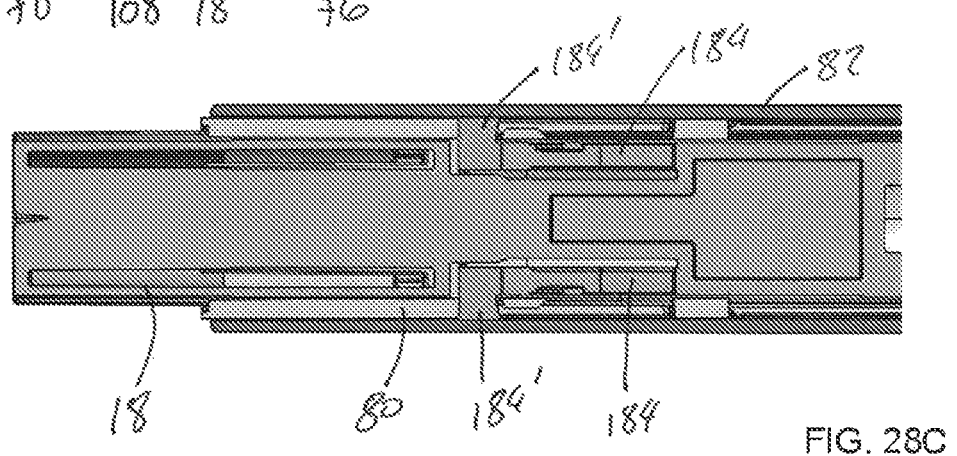

FIGS. 28A to 28C show various views of the autoinjector 10 of FIG. 21 in a storage state in part schematic sectional views. FIG. 28A shows how the cap 70 is arranged at the proximal end 28 of the needle guard 18. This engagement is achieved via the snap fit connection 94 present between the snap fit area 98 of the cap 70 and the snap fit projection 96 of the needle guard 18.

As shown in FIG. 28B, in the storage condition, the drive spring 74 is compressed and applies an axial load between the outer Body 82 and the drive chassis 24. The drive chassis 24 is prevented from moving by the engagement of the two trigger arms 36 that engage the stop feature 54 of the outer body 82.

Each trigger arm 36 and the stop feature 54 comprises angled surface that are angled so that under the action of the axial force from the drive spring 74 on the drive chassis 24, the trigger arms 36 are biased into engagement and discouraged from moving either transversely or radially inwards relative to the stop feature 54.

The drive spring 74 is supported within the drive chassis 24 in a spring bore also known as the passage 140 and on the projection 86 of the outer body 82 also known as a spring support pin. The inner body 80 and the outer body 82 are clipped together at the status indicator window clip joint formed by a protrusion 256 formed on the inner body, which fits inside the status indicator window 20 in the outer body 82. The projections 108 of the needle shield holder 104 present at the cap 70 engage behind the distal end of the rigid needle shield 78. The distal end of the cap 70 is pressed against the inner body 80. The lock-out spring 76 applies an axial force between the inner body 80 and the needle guard 18. The syringe 16 is radially supported by a syringe rib 258 in the inner body 80 and axially by a syringe flange ring 260 near the distal end of the inner body 80 (see FIG. 24B also). Some radial interference is provided by the syringe flange ring 260 to minimize rattle and free axial movement of the syringe 16. The syringe 16 is prevented from moving distally by ribs in the outer body 82 (and also by the RNS 78 engagement with the cap 70). If a cut flange syringe is fitted, it may be prevented from rotating by providing further ribs (not shown) in the inner body 80. In this connection it should be noted that the inner body 80 can comprise support elements (not shown) that support the trigger arms 36 of the drive chassis 24 during the storage state of the autoinjector 10.

Such support elements would be arranged at the distal end of the inner body 80 such that they engage the trigger arms 36 between 30% and 70% of their length to increase the stiffness of the trigger arms 36 and to act as a support that discourages unwanted disengagement of the trigger arms 36 from the stop feature 54.

At point of use, the user removes the cap 70, overcoming the snap fit connection 94, i.e., the projections 96 and removing the RNS 78 from the syringe 16 via the cap 70 having the projections 108 (or equivalent metal pressing as shown in FIG. 27A to d). As indicated in FIG. 28B, the removable needle shield 78 is captured within the cap 70 after removal.

Figure 29A:
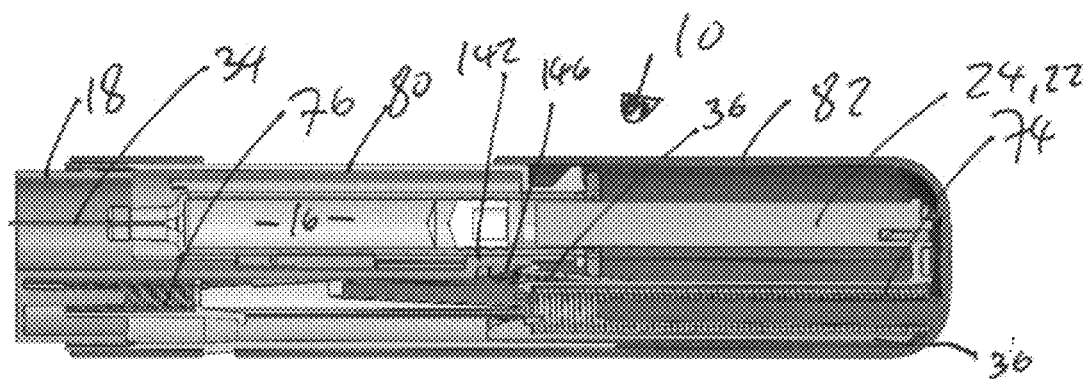
FIGS. 29A and 29B are views of the autoinjector of FIG. 21 on activation of the autoinjector.
Figure 29B:
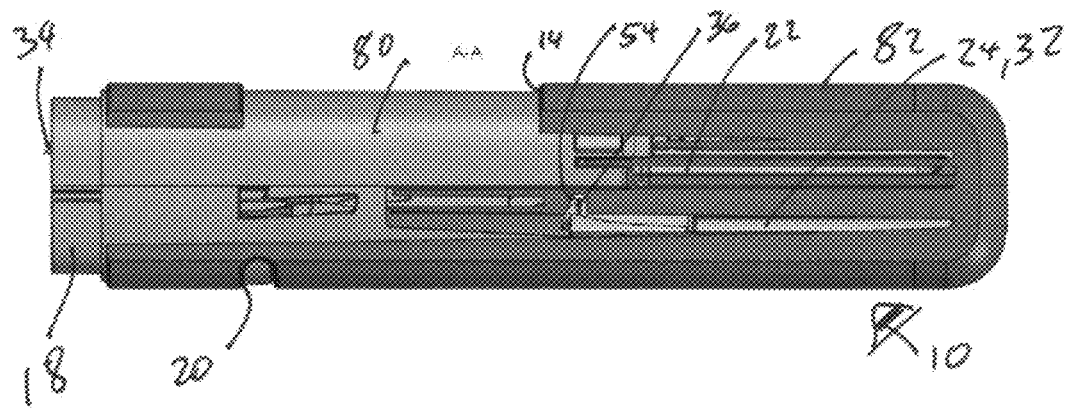

FIGS. 29A and 29B are views of the autoinjector of FIG. 21 on triggering, i.e., activation, of the autoinjector 10. For this, the user holds the outer body 82 and presses the needle guard 18 against the skin, so that the needle guard 18 is moved in the distal direction and inside the outer body 82, against the force of the lock-out spring 76 (which is compressed). During this movement, the plunger arm 142 at the distal end of the needle guard 18 contacts the drive chassis trigger arms 36 via the engagement surfaces 146 and pushes them transversely. As the trigger arms 36 move transversely, they ride up the slope of the first planar surface 156, causing the drive chassis 24 to move slightly distally, which in turn causes the drive spring 74 to be slightly further compressed. When the needle guard 18 has pushed the trigger arms 36 transversely over the apex 160 of the convex surface 152 acting as a trigger stop of the stop feature 54 of the outer body 82, the force from the drive spring 74 on the spring chassis 24 causes the trigger arms 36 to slide down the second planar surface 258, i.e., the steeper slope of the trigger stop.

When the trigger arms 36 release from the trigger stops, i.e., the stop feature under the action of the high force from the drive spring 74, an 'audible click' will be emitted (due to the sudden release of energy).

FIGS. 29A and 29B show the autoinjector 10 in a state where the needle guard 18 has been moved in the distal direction but has not yet engaged the stop feature.

Figures 30E, 30F, 30G, 30H, 30I:
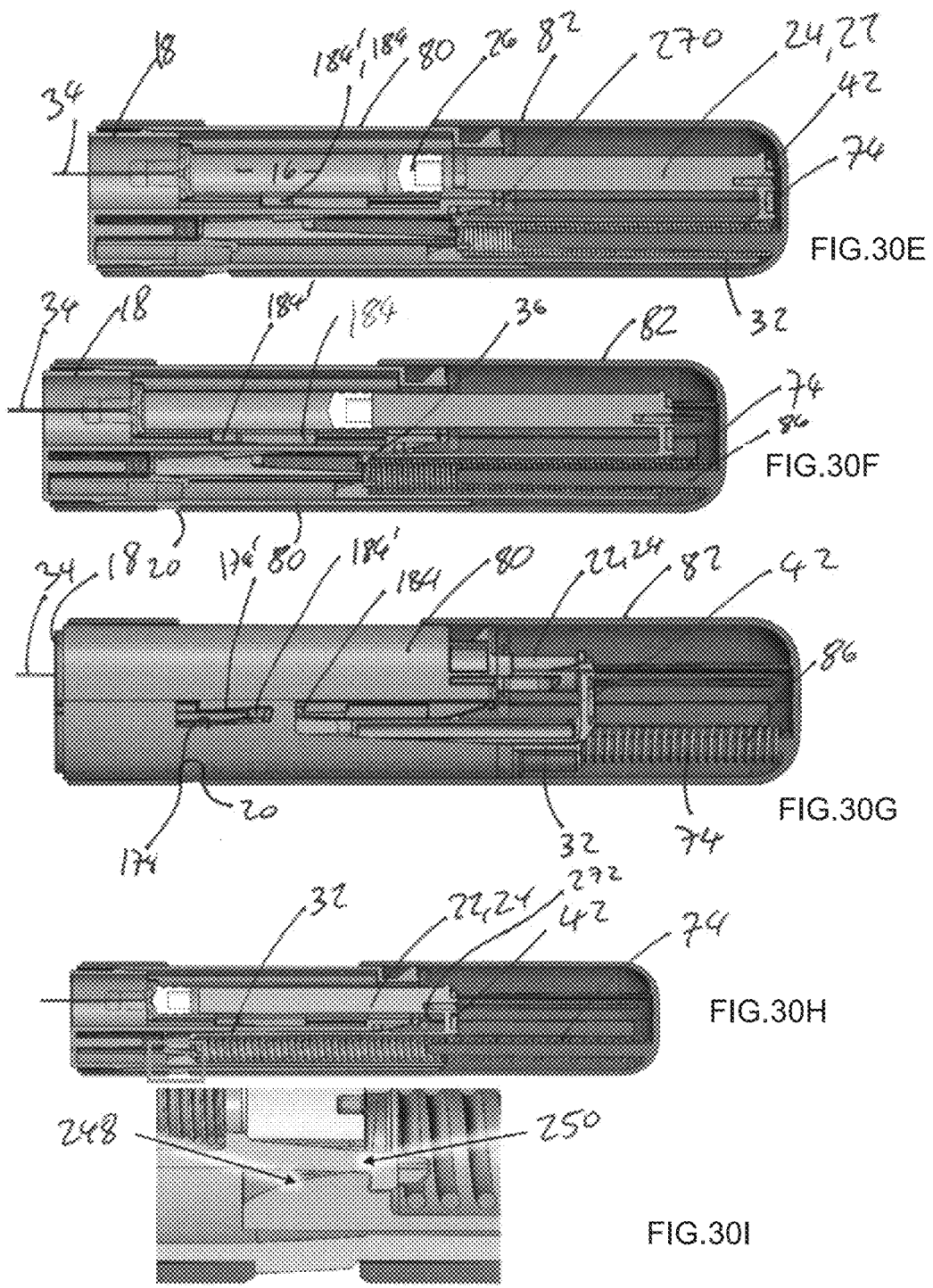

FIGS. 30A 30I show the movement of the needle guard 18, of the trigger arms 36 and of the drive chassis 24 following activation of the autoinjector 10. FIGS. 30A to d show the movement of the stop feature 54 relative to the trigger arms 36 once the needle guard 18 engages the trigger arms 36. FIG. 30A shows the release mechanism in the non-activated state, i.e., a convex surface 262 of the trigger arm 36 sits on the convex surface 152 of the stop feature 54. In this connection it should be noted that the concave surface 262 is formed complementary to the convex surface to minimize a clearance between the two components. For this purpose, the concave surface 262 has a first planar portion 264 and a second planar portion 266 that connected to one another via a depression 268.

FIG. 30B shows the slight distal movement of the trigger arm 36 relative to the stop feature 54 while the needle guard 18 further compresses the biased drive spring 74 and the trigger arm 36 is moved in the transverse direction T.

The needle guard 18 will continue to be displaced distally until it stops on rib features 270 on the inner body 80 as indicated in FIGS. 30E and 30F. At this point, the needle guard 18 will be fully engaged with the trigger arms 36, moving them transversely as far as they need to travel to overcome the apex 160 of the stop feature 54 of the outer body 82 as shown in FIG. 30D.

As the drive chassis 24 advances in the proximal direction as indicated in FIG. 30F, the trigger arms 36 slide along the clip arms 184 of the needle guard 18. This tends to bias the clip arms 184 transversely (upwards in FIG. 30G) against a surface of the long limb 238 of the aperture 174' in the inner body 80. Once the trigger arms 36 are released from the stop feature 54 of the release mechanism 40, the drive chassis 24 is moved in the proximal direction under the action of the drive spring 74.

The dispensing limb 22 of the drive chassis 24 will contact and then begin to move the plunger 26 (there may initially be a gap), forcing the medicament through the needle 34. Once the plunger 26 has reached the "fully dispensed state", the first part outer surface 50 of the drive chassis 24 begins to fill the status indicator window 20 so that the molded (optionally bright) color of the drive chassis 24 is visible through the window 20, providing a clear binary indication to the user that dispensing is complete. Before dispensing, the drive chassis 24 is not visible directly behind the window 20 so it will look dark with some shadows of the device internals.

The drive spring 74 will continue to advance the drive chassis 24 until one of the following occurs (depending on the stopper compliance and tolerance condition of the components): The projection 86 on the outer body 82 remains axially overlapped with the drive chassis 24 so that the drive spring 74 is fully supported (and prevented from buckling) all the way through dispensing.

In an ideal situation the trigger arms 36 would require a low force to deform transversely i.e., be transversely flexible (to reduce the user force required to trigger the autoinjector 10) but be very stiff and strong axially (to avoid buckling under long term loads from the drive spring 74). To try to achieve this, the trigger arms 36 of the drive chassis 34 can be formed thicker in the middle section (to increase buckling strength) and thinner at the root (to reduce transverse stiffness).

As indicated at the end of dispensing in FIGS. 30H and 30I, the EoD click arm 248 of the inner body 80 has engaged the EoD ramp 248 of the drive chassis 24 bringing about an audible click. As can also be seen in FIG. 30H, the web 42 of the drive chassis 24 abuts a drive chassis support 242 that is configured to absorb any residual force remaining in the system on releasing the spring bias of the drive spring 74.

Figure 31:
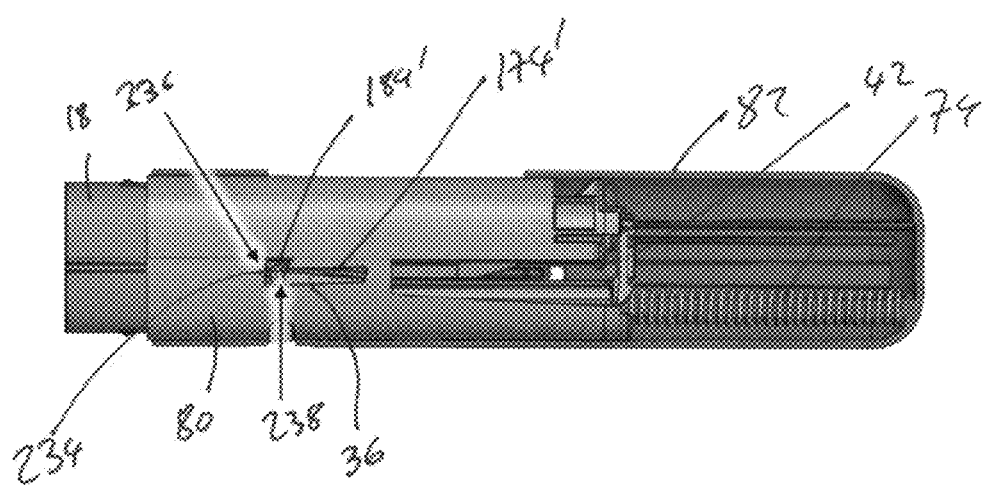
FIG. 31 is a side view of the autoinjector of FIG. 21 in the lock-out state in which portion of the outer body of the housing is broken away.
Figure 34:
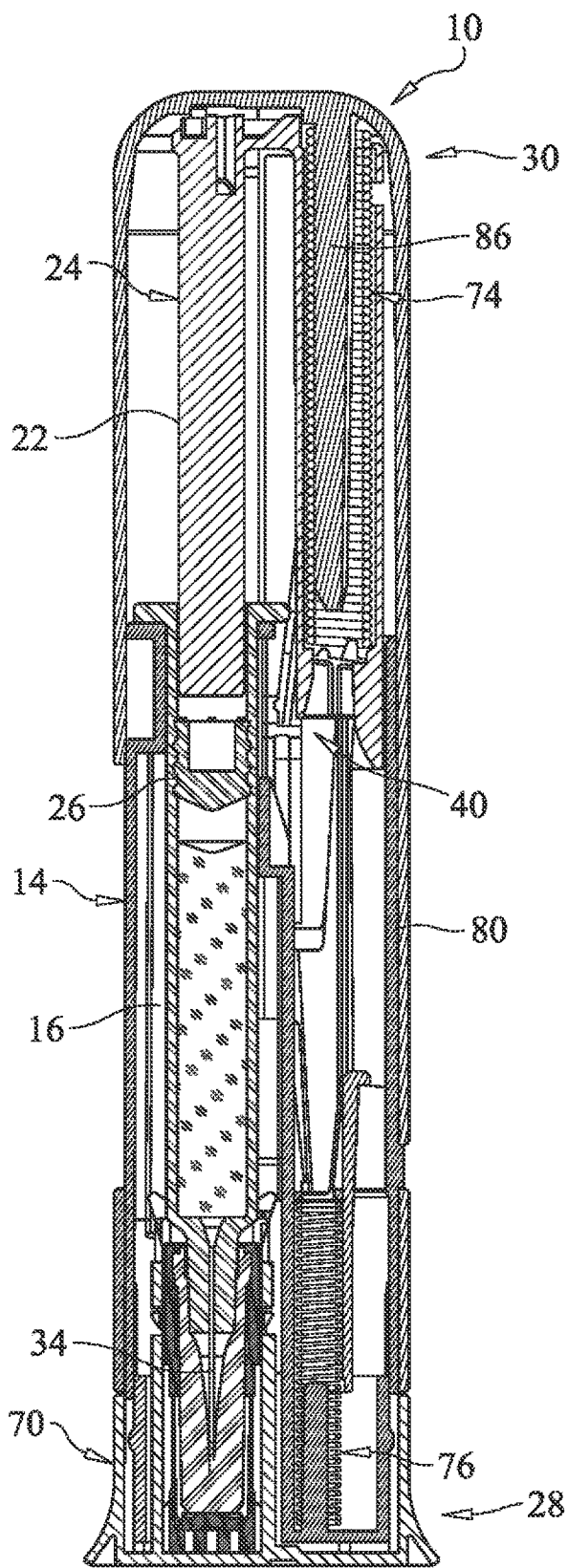
FIG. 34 is a sectional view of the autoinjector of FIG. 32 in the storage state in which the section is taken along an axial center plane of the autoinjector.

FIG. 31 shows a view of the autoinjector 10 of FIG. 21 in the lock-out state. As the autoinjector 10 is removed from the skin, the needle guard 18 extends out of the inner body 80 in a proximal direction under the action of the lock-out spring 76. The blocks 184' at the end of the clip arms 184 are biased transversely (upwards in the image above) within the short limb 236 of the aperture 174' of the inner body 80 by the trigger arms 36 of the drive chassis 24. As the needle guard 18 moves proximally, the blocks 184' are configured to move proximally along the long limb 238 and on reaching the short limb 236 the blocks 184' are configured to be deflected by the trigger arms 36 and locked into the short limb 236. The lock-out spring 76 biases the block 184' in a proximal direction against the lock-out surface 234 of the aperture 174', preventing the needle guard 18 from moving further in the proximal direction.

If the user removes the autoinjector from their skin before dispensing is finished, the needle guard 18 will be extended by the lock-out spring 76. The drive spring 74 will nevertheless continue to advance the drive chassis 24 within the syringe 16 and liquid will still be dispensed from the needle 34. During the remainder of the dispensing, the trigger arms will move the needle guard 18 clip arms 184 into the locked position within the aperture 174' as per a 'normal' dispensing.

FIGS. 32 to 43 show various views of a further example of the autoinjector 10. In the following description of the autoinjector 10 shown in FIGS. 32 to 43, only the differences between the needle guard 18, the drive chassis 24, the inner body 80, and the outer body 82 will be discussed. The other parts are identical to one of the prior embodiments. Thus, the descriptions of the parts of the autoinjector 10 shown in FIGS. 32 to 39 that are identical to the parts of the prior embodiment have not been repeated for the sake of brevity. Those parts of the needle guard 18, the drive chassis 24 and the inner body 80, the outer body 82 that are shown in the foregoing and not discussed in the following can likewise be understood from the prior description provided at the corresponding component.

Like with the previous designs of the autoinjector 10 shown in FIGS. 32 to 43, the needle guard 18 is mounted axially moveable in the housing 12 for movement between a storage state, a dispensing state and a lock-out state in which states the needle guard 18 adopts different axial positions relative to the inner body 80 of the housing 12. Here, in the autoinjector 10 shown in FIGS. 32 to 43, the needle guard 18 selectively engages the housing 12 to establish a frontmost position of the needle guard 18 in the storage state, and an offset position of the needle guard 18 in the lock-out state. The offset position is axially offset from the frontmost position.

As seen in FIGS. 35, 37, 39 and 41, in this embodiment, each of the L-shaped cut-outs 174 of the inner body 80 has been modified to provide a first stop surface 242a and a second stop surface 244a. The first stop surface 242a of the housing 12 is formed by the long limb 238 of the L-shaped cut-out 174. The second stop surface 244a of the housing 12 is formed by the short limb 236 of the L-shaped cut-out 174. The first stop surface 242a of the housing 12 and the second stop surface 244a of the housing 12 form a step 245 between the long limb 238 and the short limb 236. The first stop surface 242a is axially offset from the second stop surface 244a with respect to the housing 12. In particular, the first stop surface 242a is located closer to the proximal end of the housing 12 than the second stop surface 244a.

Figure 35:
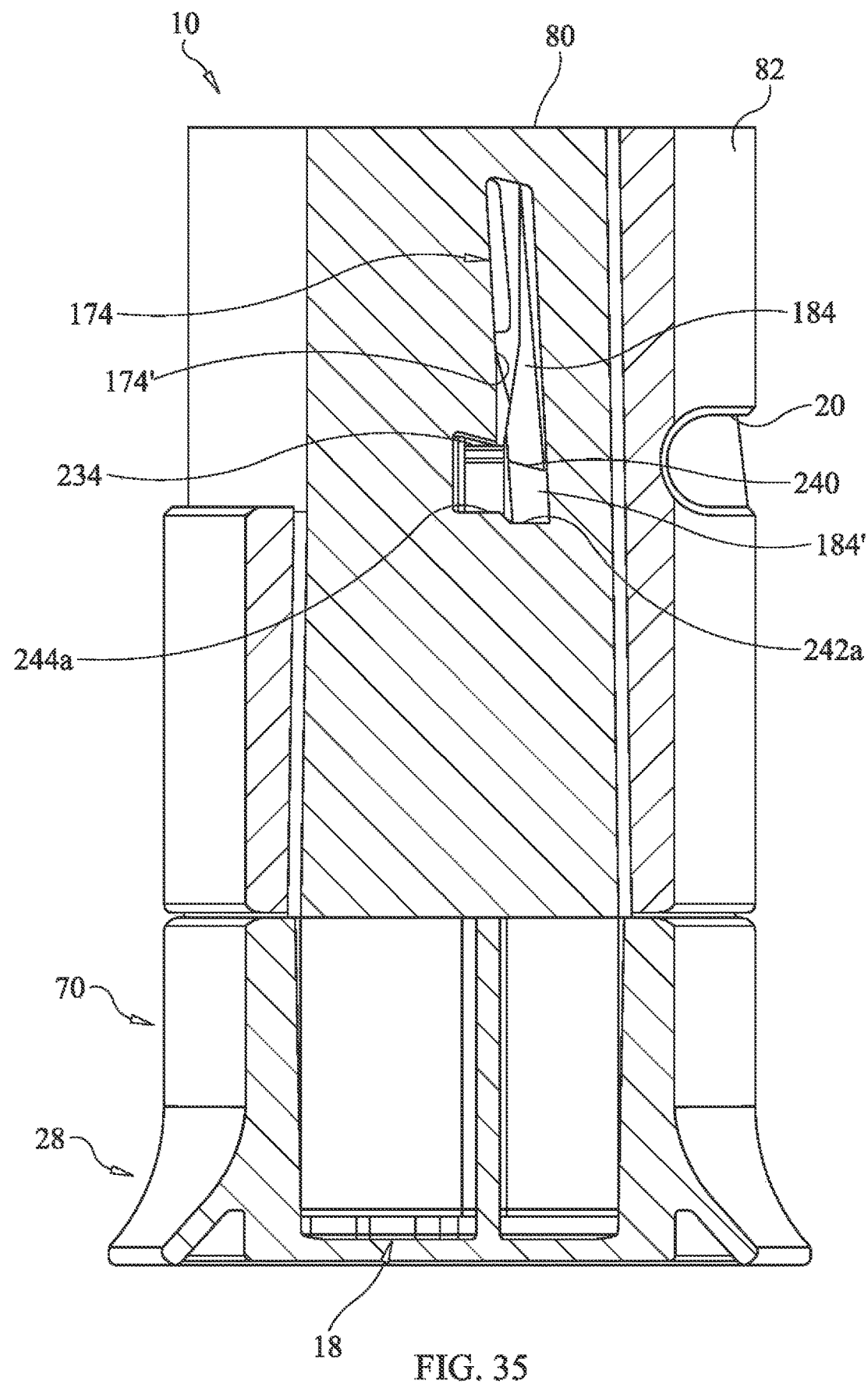
FIG. 35 is a part sectional view of the autoinjector of FIGS. 32 to 34 in the storage state.
Figure 36:
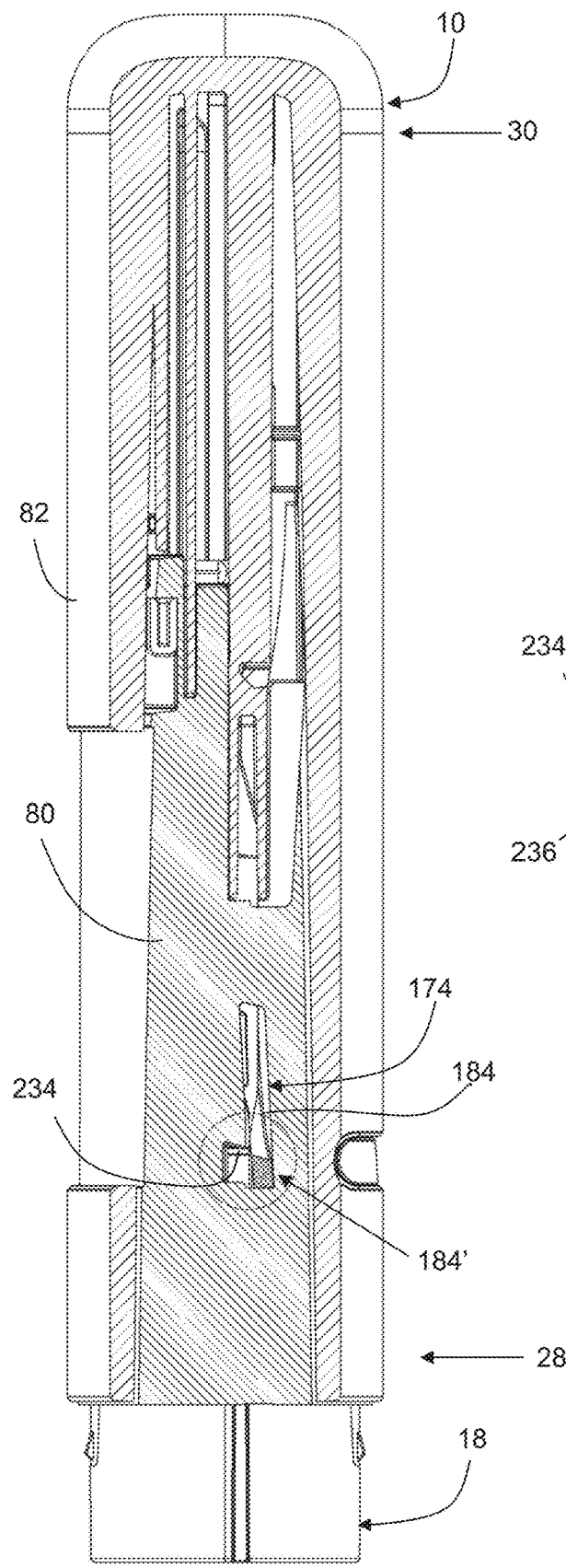
FIG. 36 is a part sectional view of the autoinjector of FIGS. 32 to 35 in the storage state.
Figure 37:
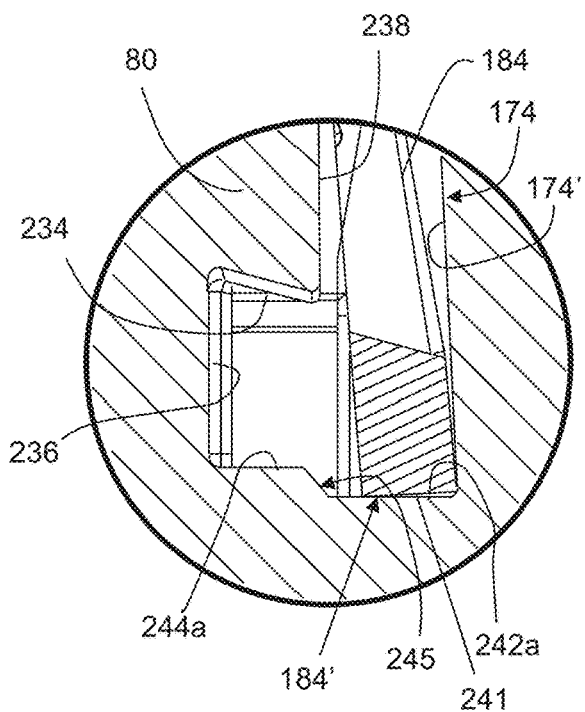
FIG. 37 is an enlargement of the circled portion of the autoinjector of FIG. 36 in the storage state.
Figures 38, 39:
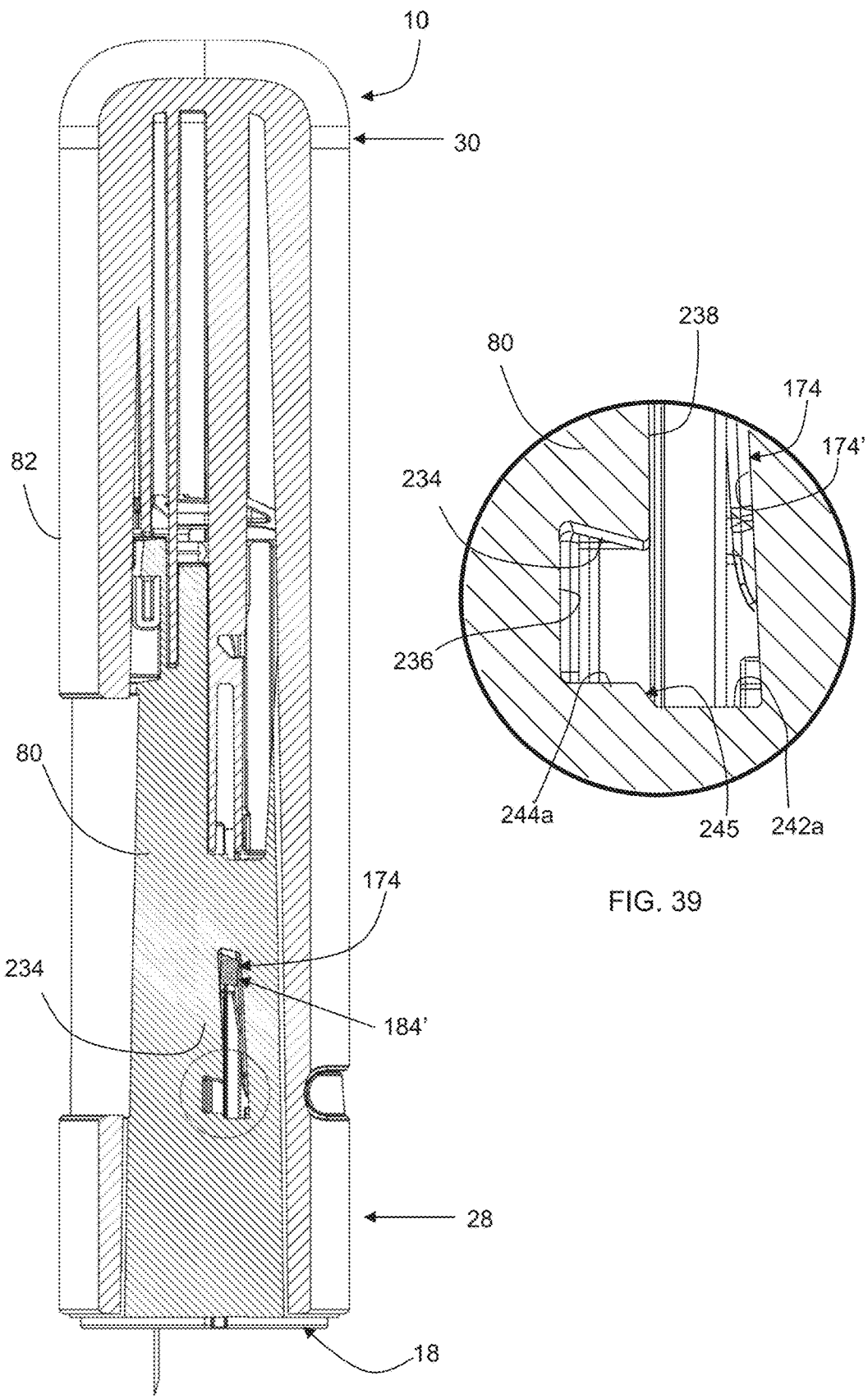
FIG. 38 is a part sectional view of the autoinjector of FIGS. 32 to 37 in the dispensing state.
FIG. 39 is an enlargement of the circled portion of the autoinjector of FIG. 38 in the dispensing state.
Figures 40, 41:
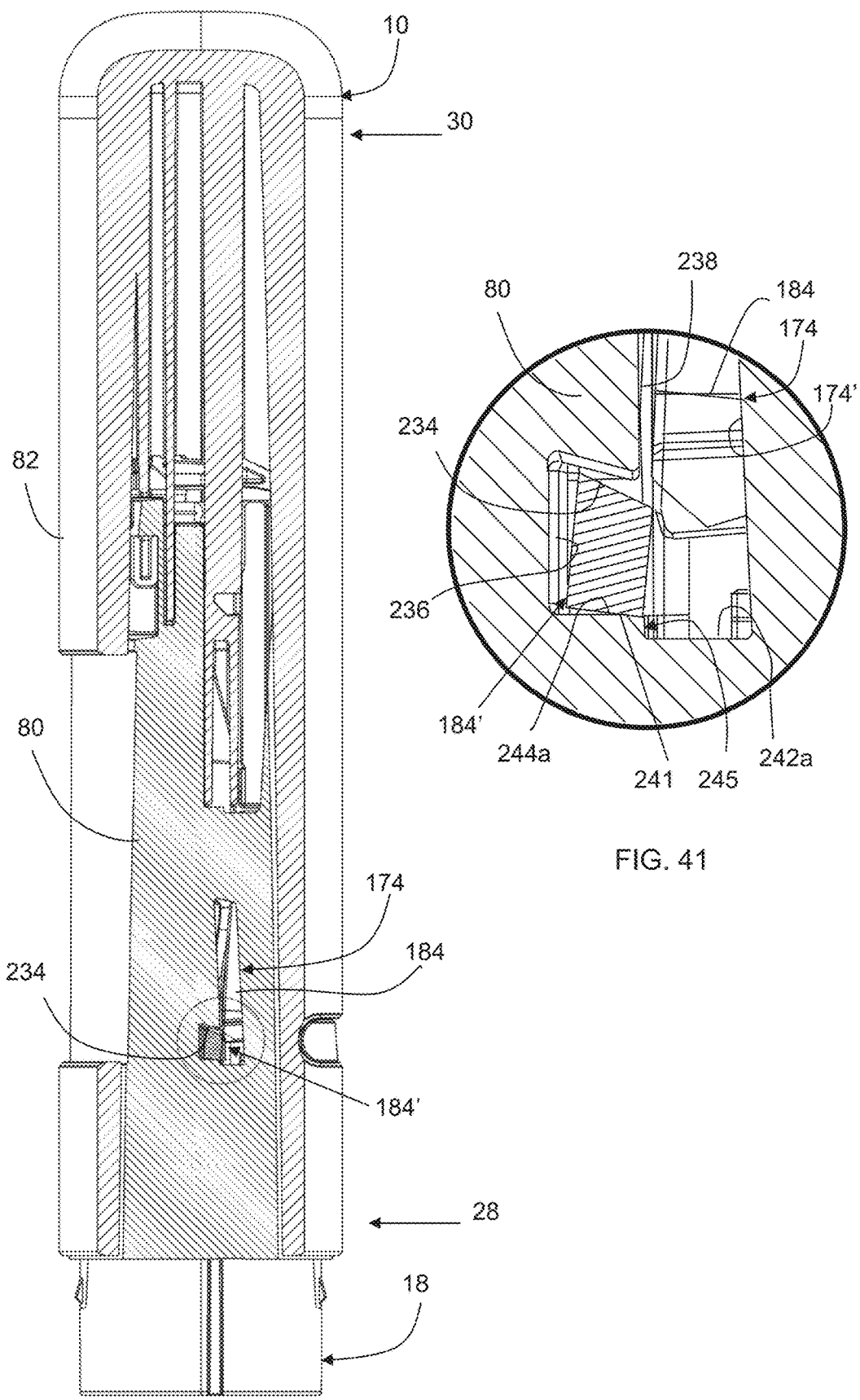
FIG. 40 is a part sectional view of the autoinjector of FIGS. 32 to 39 in the lock-out state.
FIG. 41 is an enlargement of the circled portion of the autoinjector of FIG. 40 in the lock-out state.

With this configuration, the blocks 184' on the clip arms 184 engage the first stop surfaces 242a to establish a frontmost position of the needle guard 18 with respect to the housing 12 in the storage state as seen in FIGS. 35 to 37. In particular, each of the blocks 184' on the clip arms 184 has an abutment surface 241 that selectively contacts a respective one of the first stop surface 242a and the second stop surface 244a. In other words, the abutment surface 241 is configured to engage the first stop surface 242a of the housing 12 to establish a frontmost position of the needle guard 18 with respect to the housing 12 in the storage state. Moreover, the abutment surface 241 is configured to engage the second stop surface 244a of the housing 12 to establish an offset position of the needle guard 18 with respect to the housing 12 in the lock-out state. The offset position is axially offset with respect to the housing 12 from the frontmost position of the needle guard 18.

Also, with this configuration, the blocks 184' on the clip arms 184 engage the first stop surfaces 242a to establish an frontmost position of the needle guard 18 with respect to the housing 12 in the storage state as seen in FIGS. 36 and 37. Thus, as mentioned above, the frontmost position of the needle guard 18 is axially offset with respect to the housing 12 from the offset position of the needle guard 18. In this way, the blocks 184' on the clip arms 184 are prevented from inadvertently being moved into the short limbs 236 of the L-shaped cut-outs 174. In other words, this configuration eliminates the risk that the blocks 184' will be engaged with the lock-out surfaces 234 before use. Moreover, this configuration prevents reattachment of the cap 70 to the needle guard 18. In particular, as seen in FIGS. 42 and 43, the foremost edge 18a of the needle guard 18 in the lock-out state (FIG. 43) is offset from the foremost edge 18a of the needle guard 18 in the storage state (FIG. 42) by an offset amount G. Thus, since the needle guard 18 cannot extend to the frontmost position as seen in FIG. 43 after dispensing, the cap 70 cannot engage the snap fit projection 96 of the needle guard 18 to reattach the cap 70.

While this embodiment uses two of the clip arms 174 and two of the L-shaped cut-outs 174, the autoinjector 10 can be constructed with one or more of the clip arms 174 and with one or more of the L-shaped cut-outs 174, as needed and/or desired.

Figure 45:
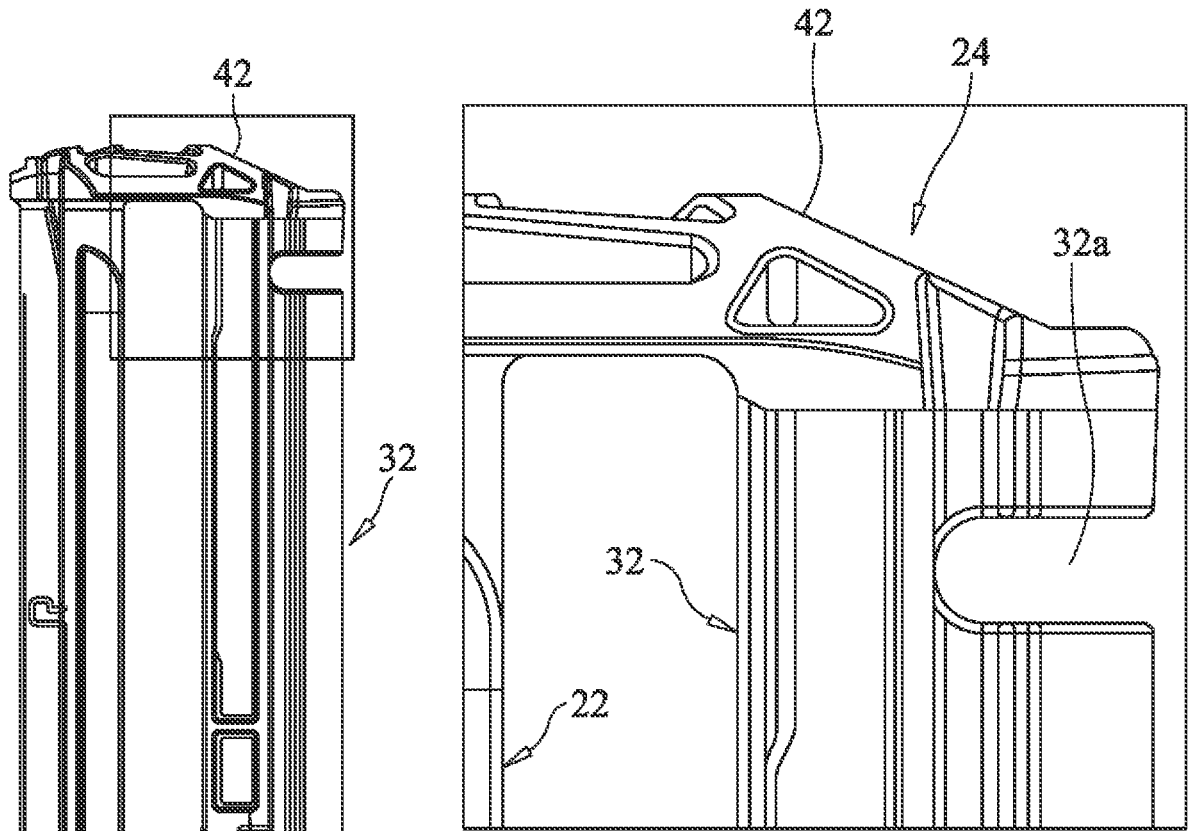
FIG. 45 is an enlargement of the boxed portion of the drive chassis of FIG. 44.
Figure 44:
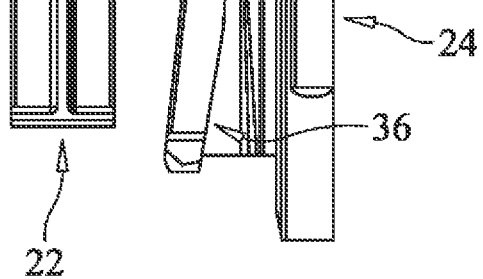
FIG. 44 is a side elevational view of the drive chassis of the autoinjector of FIGS. 32 to 43.

As seen in FIGS. 44 and 45, the drive chassis 24 of this embodiment, the axial thickness of the web 42 has been increased and stiffening ribs have been added to improve the strength and resistance to fracture under the impact loading experienced after the drive chassis 24 is released during dispensing. The trigger limb 32 has been provided with a relief cut-out 32a to a desired flexibility between the dispensing limb 22 and the trigger limb 32. In a triggering impact event, a 'hinge' is created in the trigger limb 32 by the relief cut-out 32a.

Figure 46:
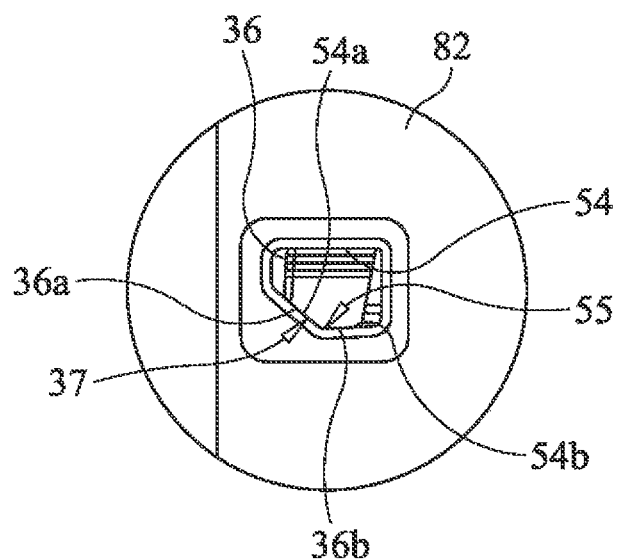
FIG. 46 is an enlargement of the circled portion of the autoinjector of FIG. 32.
Figure 47:
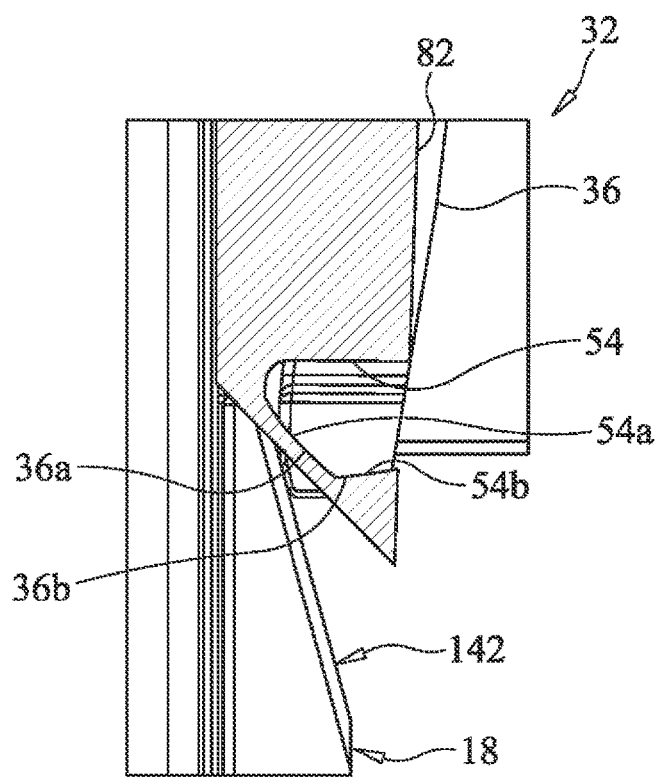
FIGS. 47 to 50 are a series of partial perspective views showing an activation of the release mechanism during a dispensing operation of the autoinjector of FIGS. 32 to 46.
Figure 48:
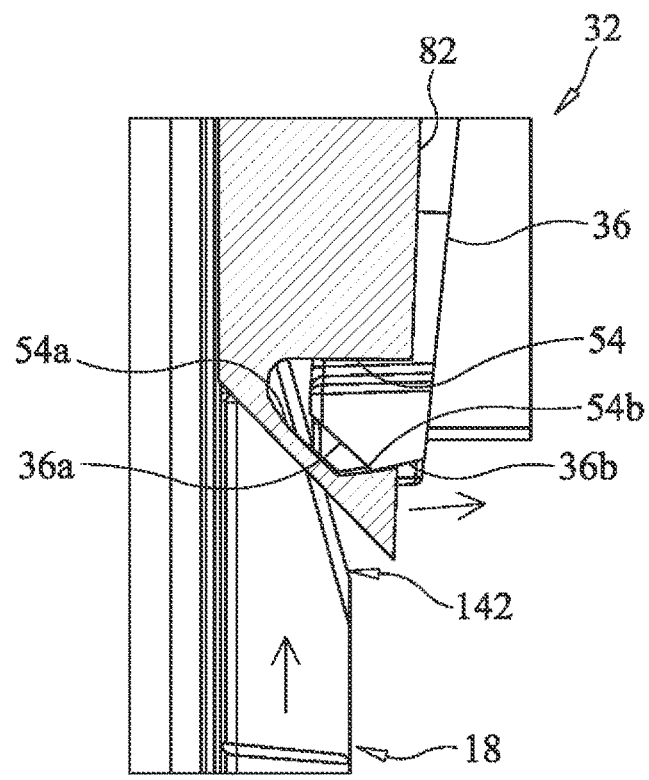
Figure 49:
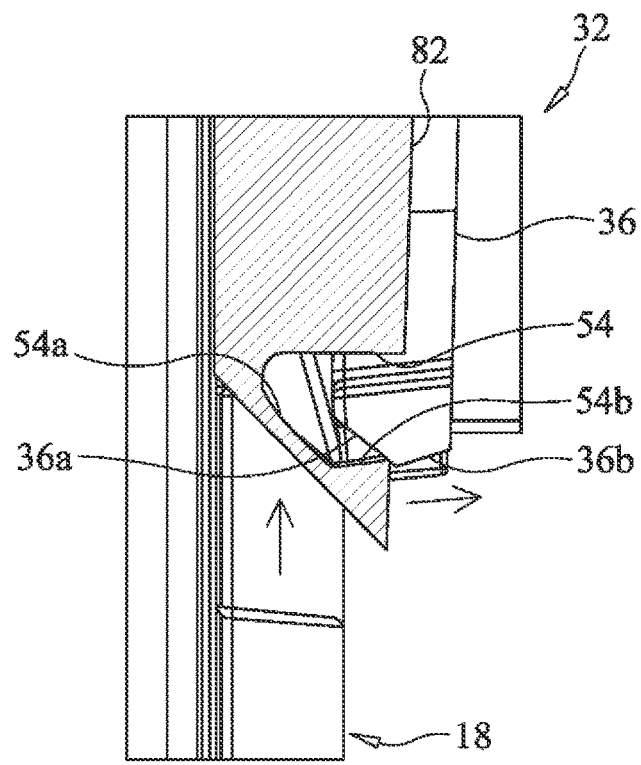
Figure 50:
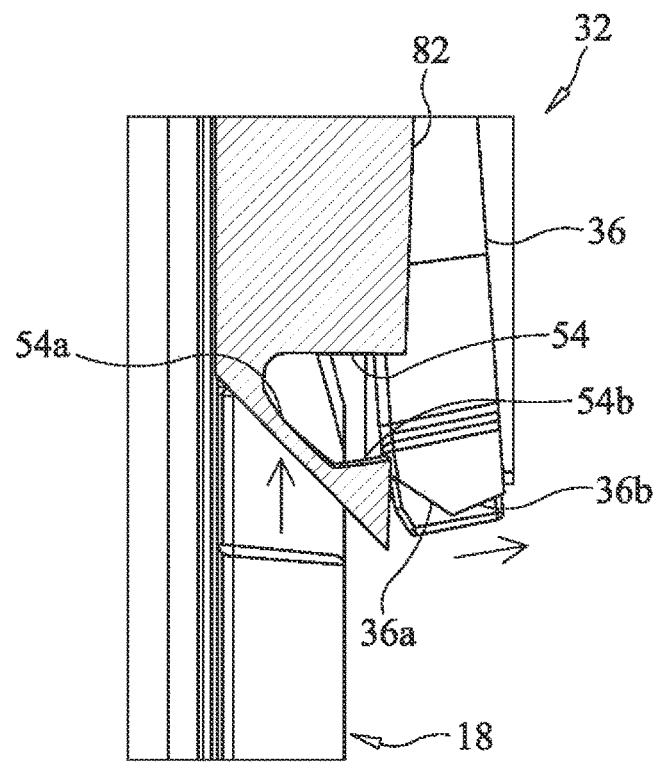

As seen in FIGS. 46 to 49, each of the trigger arms 36 is engaged with one the stop features 54 of the outer body 82 in the storage state of the needle guard 18. As seen in FIG. 50, each of the trigger arms 36 is disengaged from the stop features 54 of the outer body 82 when the needle guard 18 is moved axially into the housing 12. As seen in FIG. 46, each of the trigger arms 36 has a convex contact surface 37 formed by a first contact surface 36a and a second contact surface 36b. The convex contact surfaces 37 are configured to engage the stop features 54 of the outer body 82 in the storage state of the needle guard 18. The first contact surface 36a and the second contact surface 36a form an arrowhead shape. Here, the first contact surface 36a is inclined at a steeper angle than the second contact surface 36a with respect to a transverse plane that is perpendicular to the axial direction of the autoinjector 10.

As seen in FIG. 46, each of the stop features 54 is an opening having a concaved surface 55 formed by a first stop surface 54a and a second stop surface 54b. Here, the first stop surface 54a and the second stop surface 54b are planar surfaces that angled. The first stop surface 54a and the second stop surface 54b form a trigger stop. The first stop surface 54a and the second stop surface 54b form a V-shaped notch. Here, the first stop surface 54a is inclined at a steeper angle than the second stop surface 54b with respect to a transverse plane that is perpendicular to the axial direction of the autoinjector 10. This minimizes the size of the openings of the stop features 54. The inclinations of the first stop surface 54a and the second stop surface 54b mate with the inclinations of the first contact surface 36a and the second contact surface 36a, respectively. This configuration improves triggering robustness and allows for the drive spring 76 to have a lower biasing force.

Figure 51:
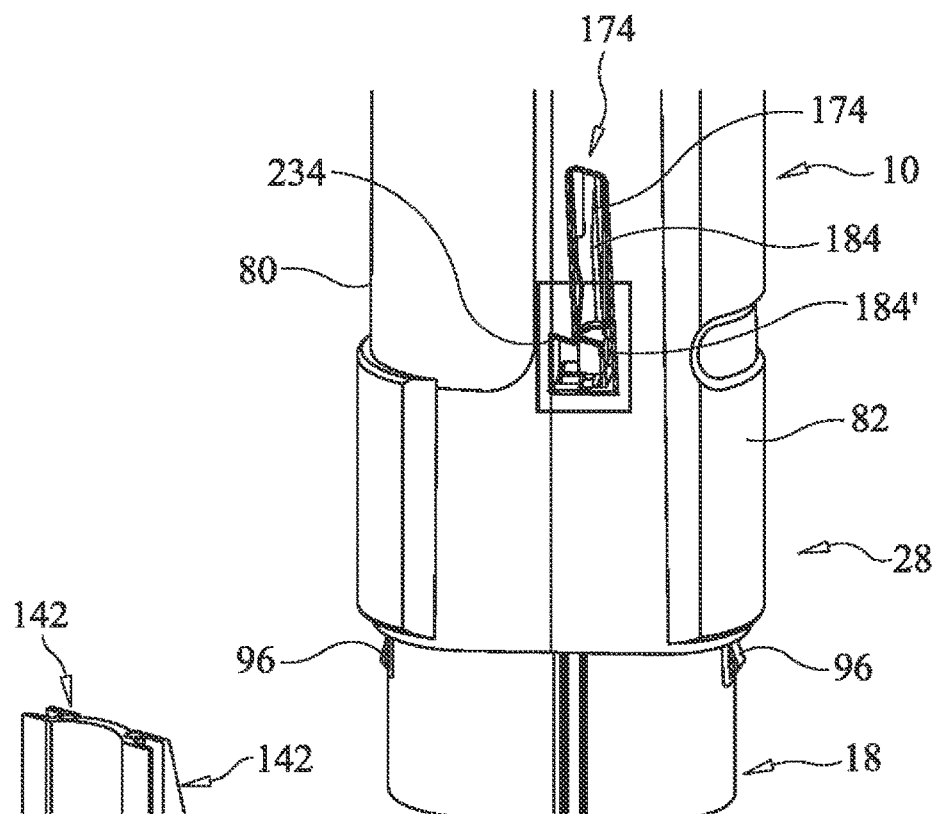
FIG. 51 is a part perspective view of a dispensing end portion of another embodiment of an autoinjector, with a part of the housing removed, such that one can see components for locking out the needle guard of an autoinjector.
Figure 52:
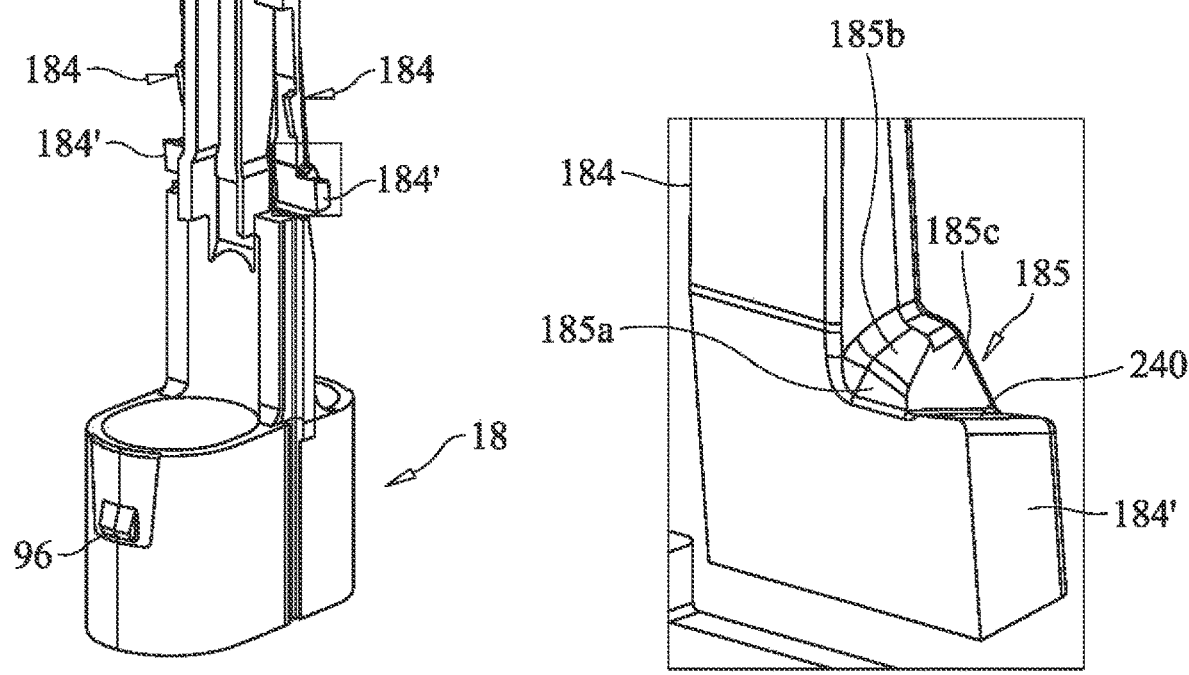
FIG. 52 is a perspective view of the needle guard of the autoinjector of FIG. 51.
Figure 53:
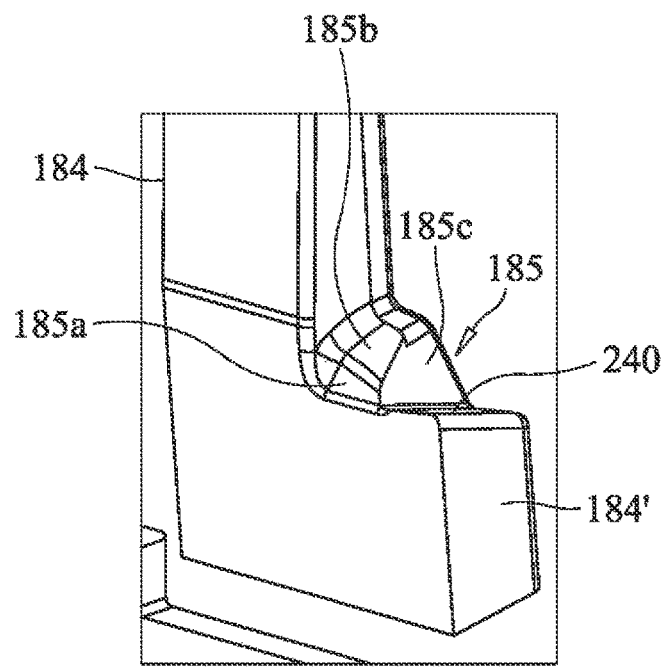
FIG. 53 is an enlargement of the boxed portion of the needle guard of FIG. 52.

FIGS. 51 to 53 show various views of a further example of the needle guard 18 for the autoinjector 10. Here, each of the blocks 184' of the needle guard 18 has been modified to include a transition surface 185 that decelerates the locking out of the needle guard 18 with the inner body 80. In particular, for example, the transition surface 185 includes a transverse lead surface 185a, a transverse ramp surface 185b and a radial ramp surface 185c.

Figure 54:
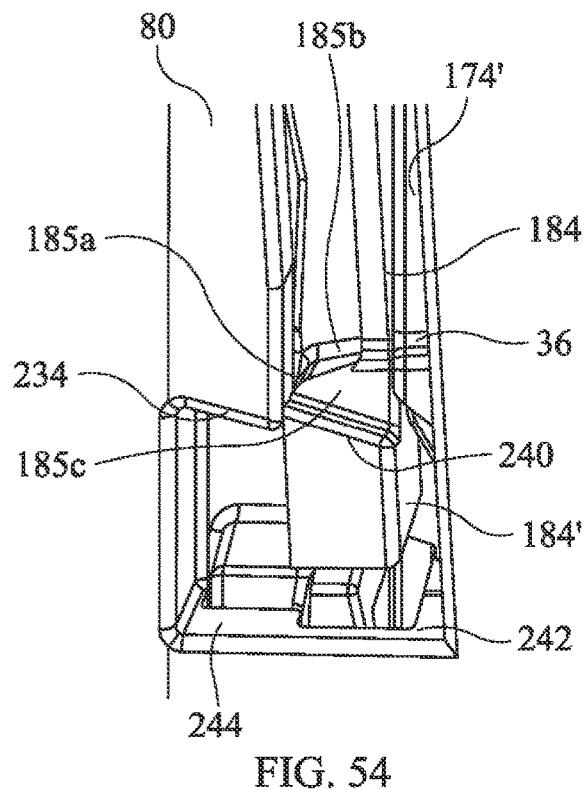
FIGS. 54 to 59 are a series of partial perspective views showing the needle guard of FIGS. 51 to 53 moving to a lock-out position.
Figure 55:
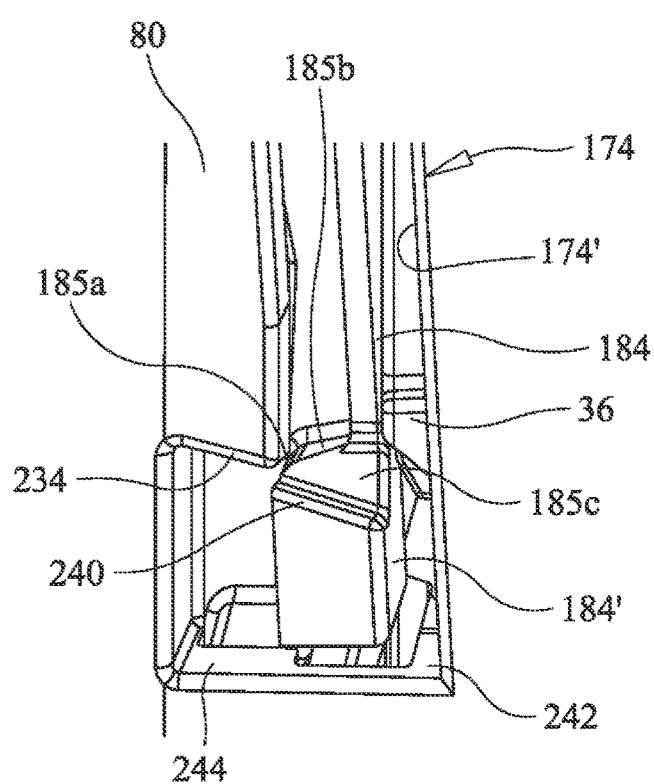

As the needle guard 18 extends proximally after dispensing, under the biasing force from the lock-out spring 76, the blocks 184' slide down the profiled apertures 174'. As seen in FIG. 54, the blocks 184' are biased into transverse contact by a transverse force applied by the trigger arms 36. As seen in FIG. 55, further proximal displacement of the needle guard 18 causes the transverse lead surfaces 185a of the blocks 184' to contact the edges of the lock-out abutment surfaces 234. As the needle guard 18 continues to move proximally, as seen in FIG. 55, the transverse lead surfaces 185a allows the blocks 184' to gradually move transversely under the force from the trigger arms 36. The steeper initial lead angles of the transverse lead surfaces 185a as compared to the transverse ramp surfaces 185b allow the needle guard 18 to be axially bias relative to the inner body 80 without significant transverse movement of the blocks 184'.

Figure 56:
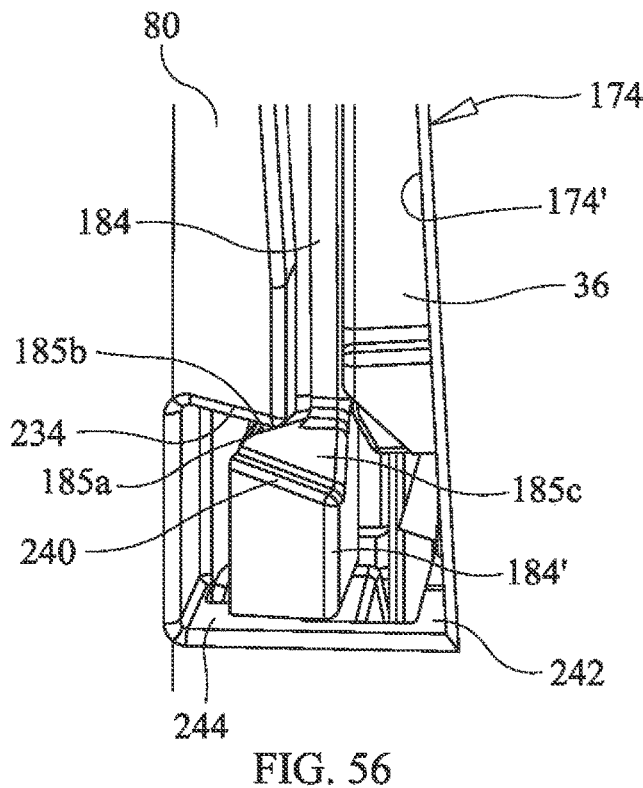
Figure 57:
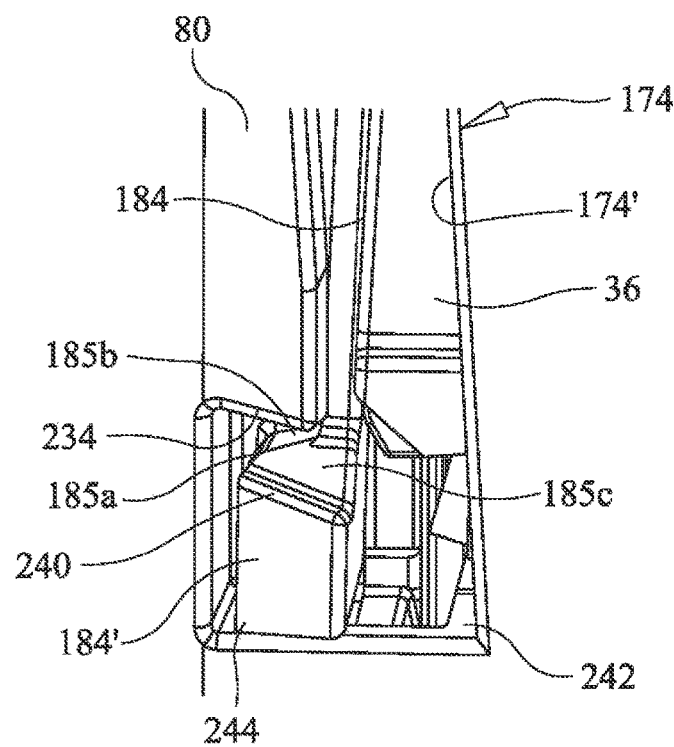

After engagement of the transverse lead surfaces 185a, as seen in FIGS. 56 and 57, the transverse ramp surfaces 185b contact the edges of the lock-out abutment surfaces 234. The engagement between the transverse ramp surfaces 185b controls the transverse movement of the blocks 184' under the biasing force provided by the trigger arms 36 as the needle guard 18 continues to extend in the proximal direction.

The transverse ramp surfaces 185b continues to control the transverse movement of the blocks 184' until the blocks 184' cease to move transversely. This occurs when the biasing force provided by the trigger arms 36 is equal and opposite to the reaction force provided by the deflected arm 184. Proximal extension of the needle guard 18 stops when the proximal surface of the blocks 184' contact the extended abutment surface 244.

Figure 58:
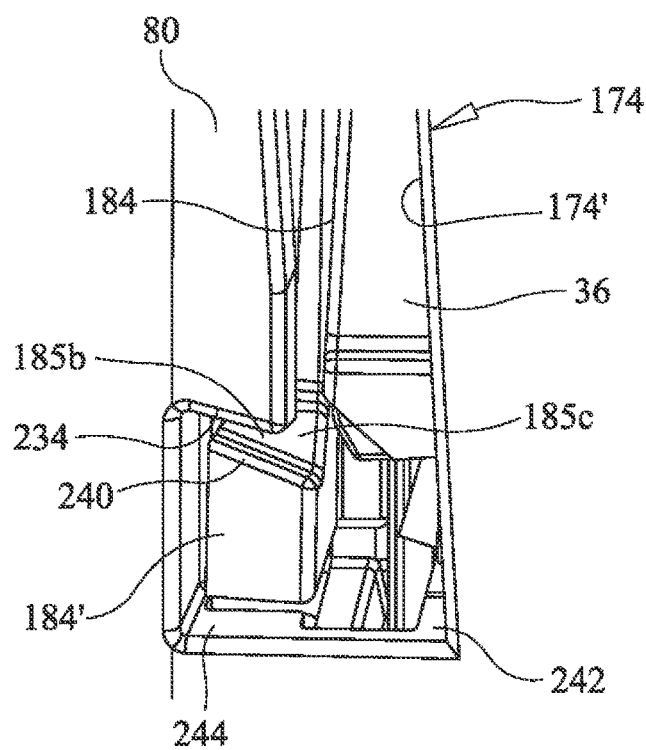
Figure 59:
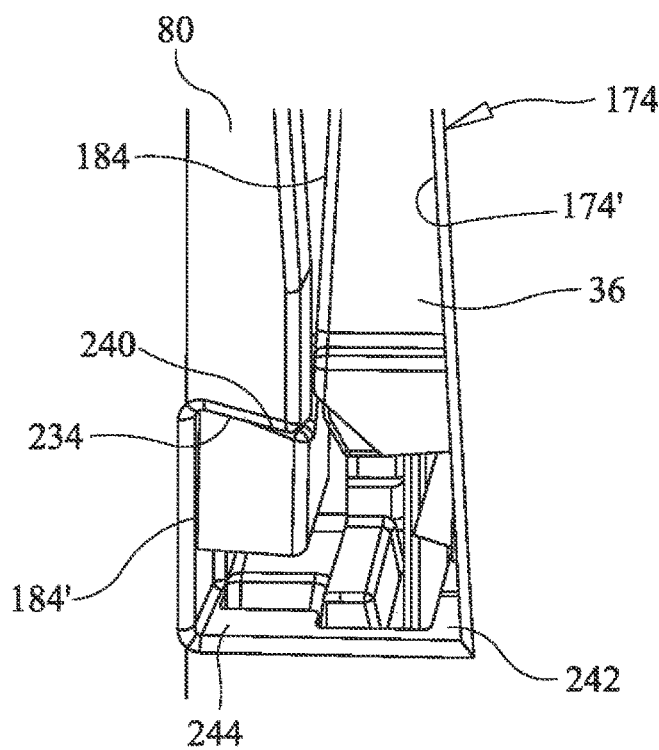
Figure 60:
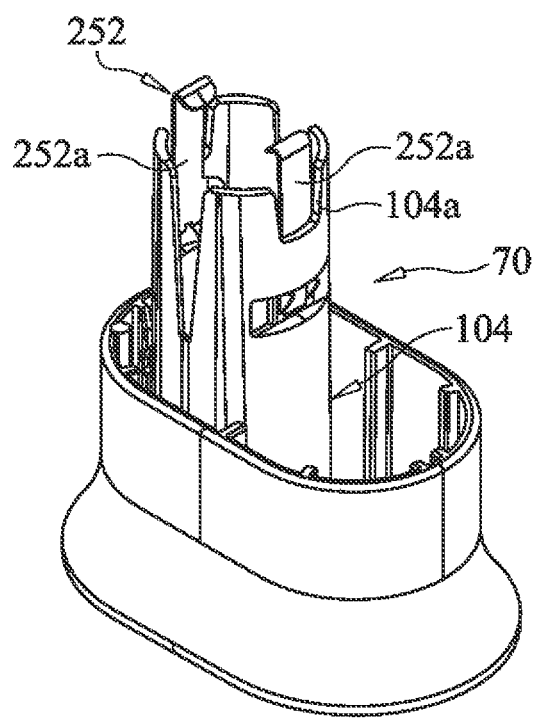
FIGS. 60 to 64 are various views of a further kind of cap that can be used with any of the disclosed in embodiments.
Figure 61:
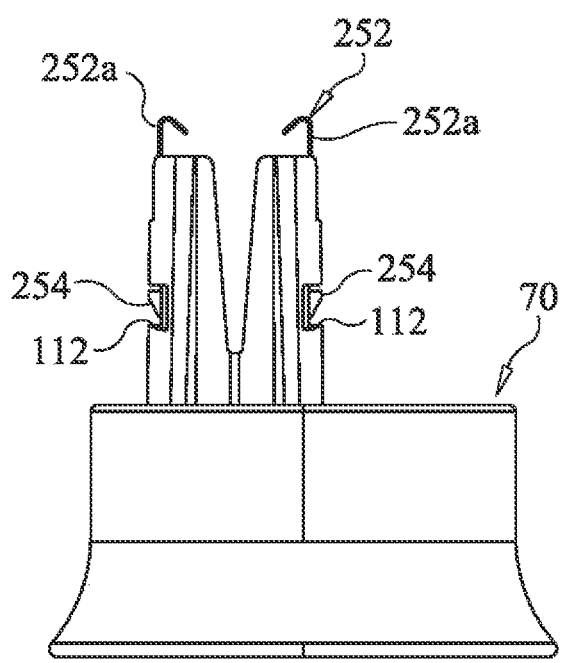
Figure 62:
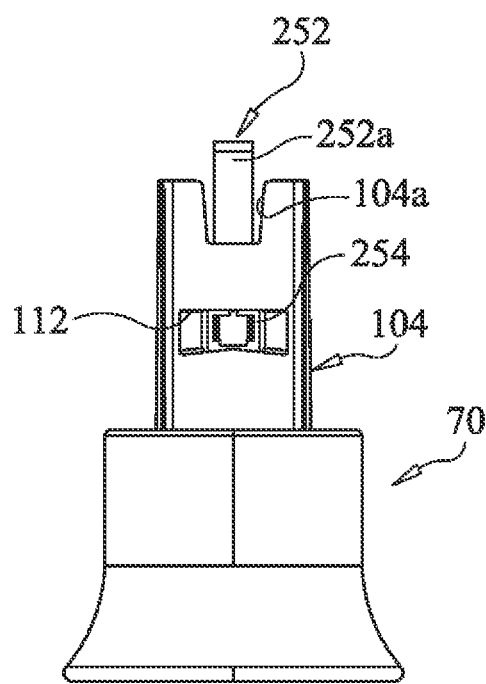
Figure 63:
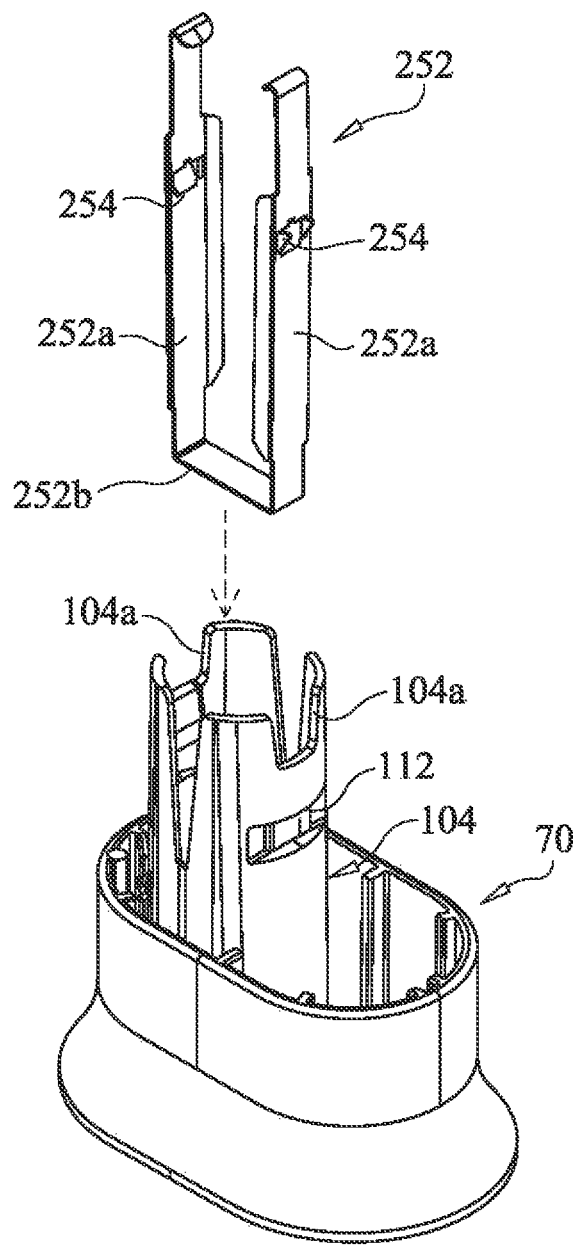
Figure 64:
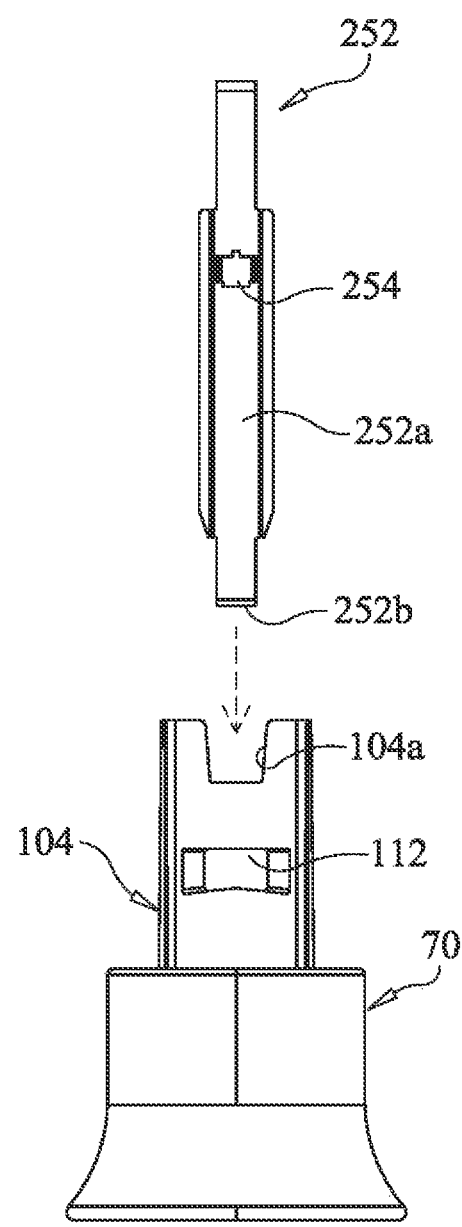

Once the blocks 184' are in the locked position as seen in FIGS. 57, if the needle guard 18 is moved in the distal direction as seen in FIG. 58, the radial ramp surfaces 185c contact the lock-out abutment surfaces 234 and forces the blocks 184' radially inwards. Further distal displacement, as seen in FIG. 59, under increasing force, creates surface contact between the surfaces 240 of the blocks 184' and the lock-out abutment surface 234.

FIGS. 60 to 64 show various views of further kind of cap 70. The cap 70 of this embodiment can be used with any of the disclosed embodiments. The cap 70 of this embodiment is made of a hard rigid material, and is substantially the same as the prior embodiments of the cap 70. The cap 70 has a metal clip 252 that engages a distal end of the removable needle shield 78. The clip 252 is generally U-shaped, and has a pair of legs 252a and a connecting part 252b. Each of the legs 252a has a hook at its free end for engaging the removable needle shield 78. In the cap 70, the clip 252 is configured to engage side walls and the distal end of the removable needle shield 78. In each case, the needle shield holder 104 has two windows 112. The windows 112 and the needle shield holder 104 are respectively configured to hold the clip 252 in place, with the clip 252 in turn being configured to remove the removable needle shield 78 on removal of the cap 70 from the autoinjector 10. For this purpose, the clip 252 comprises two barbs 254 that engage the respective windows 112. As also indicated the free end of the clip 252 facing the removable needle shield 78 is configured to exert a pressure on the removable needle shield 78 such that on removal of the cap 70 the removable needle shield 78 is also automatically removed. The needle shield holder 104 has cut-outs 104a to allow the legs 252a to flex outwardly when engaged with the removable needle shield 78.

ENUMERATED EMBODIMENTS

1. An autoinjector 10 comprising: a housing 12; a pre-filled syringe 16 mounted in the housing 12 and fixed relative to the housing 12; and a needle guard 18 mounted axially moveable in the housing 12 for movement between a storage state, a dispensing state and a lock-out state in which states the needle guard 18 adopts different axial positions relative to the housing 12, wherein the needle guard 18 is configured to be axially moved in a distal direction between the storage state and the dispensing state and wherein the needle guard 18 is configured to be axially moved in a proximal direction between the dispensing state and the lock-out state.
2. The autoinjector according to claim 1, wherein the needle guard 18 surrounds a needle 34 of the pre-filled syringe 16 in the storage state and in the lock-out state.
3. The autoinjector 10 according to embodiment 1 or embodiment 2, wherein the needle guard 18 does not surround a needle 34 of the pre-filled syringe 16 in the dispensing state.
4. The autoinjector 10 according to one of embodiments 1 to 3, further comprising a lock-out spring 76 arranged between the needle guard 18 and the housing 12.
5. The autoinjector 10 according to embodiment 4, wherein the needle guard 18 is configured to compress the lock-out spring 76 on moving between the storage state and the dispensing state.
6. The autoinjector 10 according to embodiment 4 or embodiment 5, wherein the needle guard 18 is configured to be moved by a relaxation of the lock-out spring 76 between the dispensing state and the lock-out state.
7. The autoinjector 10 according to one of embodiments 1 to 6, wherein the needle guard 18 comprises one or more lock-out arms 186.
8. The autoinjector 10 according to embodiment 7, wherein the one or more lock-out arms 186 comprise an engagement portion 220 that is configured to engage a corresponding cut-out 176 in the housing 12 of the autoinjector 10 in the lock-out state.
9. The autoinjector 10 according to one of embodiments 4 to 8 and embodiment 7, wherein two or more lock-out arms 186 are provided, with the lock-out spring 76 being arranged between the two or more lock-out arms 186.
10. The autoinjector 10 according to one of embodiments 1 to 9, wherein the needle guard 18 comprises an anti-pull off feature 170 cooperating with the housing 12.
11. The autoinjector 10 according to one of embodiments 1 to 10, wherein the needle guard 18 comprises a plunger arm 142 for activation of a release mechanism 40 of the autoinjector 10.
12. The autoinjector 10 according to embodiment 10 and embodiment 11, wherein the anti-pull off feature 170 is arranged at the plunger arm 142.
13. The autoinjector 10 according to one of embodiments 10 to 12, wherein the anti-pull of feature 170 comprises a protrusion 166 that engages a hole 168 present in the housing 12.
14. The autoinjector 10 according to one of embodiments 1 to 13, further comprising a drive chassis 24, the drive chassis 24 being mounted in the housing 12, the drive chassis 24 being biased with respect to the housing 12, the drive chassis 24 further being fixed with respect to the housing 12 and a movement relative to the housing 12 in a storage state of the autoinjector 10.
15. The autoinjector 10 according to embodiment 14 and of embodiments 7 to 13, wherein the drive chassis 24 is configured to engage the one or more clip arms 184 to deflect these radially inwardly away from the housing 12 in the dispensing state.
16. The autoinjector 10 according to embodiment 14 or embodiment 15 and one of embodiments 11 to 13, wherein the plunger arm 142 is configured to cooperate with a trigger arm 36 of the drive chassis 24 for activation of a release mechanism 40 of the autoinjector 10.
17. The autoinjector 10 according to one of embodiments 14 to 16, wherein an axial movement of the needle guard 18 towards the drive chassis 24 releases the fixing of the drive chassis 24 with respect to the housing 12 on activation of the autoinjector 10.
18. The autoinjector 10 according to embodiment 16 or embodiment 17, wherein the axial movement of the needle guard 18 is configured to deflect the trigger arm 36 in a direction transverse to the axial movement.
19. The autoinjector 10 according to one of embodiments 16 to 18 and one of embodiments 11 to 15, wherein the plunger arm 142 is configured to deflect the trigger arm 36 in a direction transverse to the axial movement of the needle guard 18.
20. The autoinjector 10 according to one of embodiments 1 to 19, wherein the needle guard 18 comprises a blocking rib 144.
21. The autoinjector 10 according to embodiment 20 and one of embodiments 16 to 19, wherein the blocking rib 144 is configured to block a radial movement of the trigger arm 36.
22. The autoinjector 10 according to one of embodiments 1 to 21, wherein the needle guard 18 further comprises cam 162 having an engagement surface 146.
23. The autoinjector 10 according to one of embodiments 16 to 21 and embodiment 22, wherein the engagement surface 146 is configured to engage the trigger arm 36.
24. The autoinjector 10 according to embodiment 23, wherein the trigger arm 36 comprises a web 148 and the engagement surface 146 engages the web 148 of the trigger arm 36.
25. The autoinjector 10 according to one of embodiments 21 to 24 and embodiment 20, wherein the engagement surface 146 projects from the blocking rib 144.
26. The autoinjector 10 according to embodiment 24 or embodiment 25, wherein the web 148 comprises a deflection surface 150 inclined with respect to a movement direction of the drive chassis 24.
27. The autoinjector 10 according to one of embodiments 22 to 26, wherein the engagement surface 146 is inclined with respect to a movement direction of the drive chassis 24.
28. The autoinjector 10 according to embodiment 26 and embodiment 27, wherein the engagement surface 146 and the deflection surface 150 are inclined with respect to a movement direction of the drive chassis 24 in a cooperating manner.

29. The autoinjector 10 according to embodiment 28, wherein the engagement surface 146 is inclined to deflect the trigger arm 36 in the direction transverse to the axial direction of movement of the needle guard 18.

30. The autoinjector 10 according to one of embodiments 14 to 29, further comprising a drive spring 74, with the drive spring 74 being configured to drive the drive chassis 24 towards the needle guard 18 after activation of the autoinjector 10.

31. The autoinjector 10 according to one of embodiments 1 to 30, wherein the needle guard 18 is configured to cooperate with a cap 70 via one or more snap-fit connections 94.

32. The autoinjector 10 according to embodiment 31, wherein each snap fit connection comprises a snap-fit projection 96 cooperating with a corresponding snap-fit area 98.

33. The autoinjector 10 according to embodiment 32, wherein the needle guard 18 comprises one or more snap-fit projections 96.

34. The autoinjector 10 according to embodiment 32 or embodiment 33, wherein one or more snap-fit projections 96 are provided at an outer surface 126 of the needle guard 18.

35. The autoinjector 10 according to one of embodiments 32 to 34, wherein an inner surface 128, 132 of the housing 12 comprises one or more grooves 130, 134 in which one or more of the snap-fit projections 96 can axially move relative to the housing 12 on an axial movement of the needle guard 18.

36. The autoinjector 10 according to one of embodiments 31 to 35, wherein a front end 122 of the needle guard 18 is arranged within an opening 124 of the cap 70.

37. The autoinjector 10 according to one of embodiments 31 to 36, wherein an outer wall 116 of the cap 70 contacts an outer wall 136 of the housing 12 in the storage state of the autoinjector 10.

38. The autoinjector 10 according to embodiment 37, wherein the outer wall 116 of the cap 70 and the outer 136 wall of the housing 12 do not overlap in an axial direction of the autoinjector 10.

39. The autoinjector 10 according to embodiment 37 or embodiment 38, wherein the outer wall 116 of the cap 70 and the outer wall 136 of the housing 12 radially overlap in the storage state of the autoinjector 10.

40. The autoinjector 10 according to one of embodiments 1 to 39, wherein the housing 12 is a two-part housing 12 comprising an inner body 80 and an outer body 82.

41. The autoinjector 10 according to one of embodiments 1 to 40, further comprising a drive chassis 24 mounted in the housing 12, the drive chassis 24 being biased with respect to the housing 12, the drive chassis 24 further being fixed with respect to the housing 12 and for a movement relative to the housing 12 in a storage state of the autoinjector 10, the drive chassis 24 moving relative to the housing 12 on dispensing a material from the pre-filled syringe 16.

42. The autoinjector 10 according to embodiment 41, wherein the autoinjector 10 is configured to generate an audible end of dose feedback between the drive chassis 24 and the housing 12 once the material has been dispensed from the autoinjector 10.

43. The autoinjector 10 according to one of embodiments 1 to 42, further comprising a drive chassis 24 mounted in the housing 12, the drive chassis 24 being biased with respect to the housing 12 by a drive spring 74, the drive chassis 24 further being fixed with respect to the housing 12 and a movement relative to the housing 12 in a storage state of the autoinjector 10.

44. The autoinjector 10 according to embodiment 43, wherein the drive chassis 24 comprises a trigger arm 36 engaging a stop feature 54 present in the housing 12 in the storage state of the autoinjector 10 for fixing the drive chassis 24 with respect to the housing 12.

45. The autoinjector 10 according to embodiment 44, wherein the trigger arm 36 is configured to be disengaged from the stop feature 54 on activation of the autoinjector 10.

46. The autoinjector 10 according to one of embodiments 1 to 45, further comprising a needle shield 78 covering a needle 34 of the pre-filled syringe 16 in a storage state of the autoinjector 10, the axially moveable needle guard 18 arranged to cover the needle 34 of the pre-filled syringe 16 at least after use of the autoinjector 10 and to move relative to the pre-filled syringe 16 during use of the autoinjector 10, as well as a removable cap 70 in which the needle guard 18 is stored in the storage state of the autoinjector 10.

47. The autoinjector 10 according to embodiment 46, wherein the cap 70 is removably connected to the needle guard 18 in the storage state of the autoinjector 10, and wherein, on removal of the cap 70, the needle shield 78 is also removed from the autoinjector 10.

48. The autoinjector 10 according to one of embodiments 1 to 47, further comprising a drive chassis 24 mounted in the housing 12, the drive chassis 24 being biased with respect to the housing 12 and being fixed with respect to the housing 12 in a storage state of the autoinjector 10.

49. The autoinjector 10 according to embodiment 48, further comprising a status indicator window 20 arranged at the housing 12 via which the drive chassis 24 is visible from the outside, with the status indicator window 20 showing a first part 50 of the drive chassis 24 in the storage state of the autoinjector 10 and a second part 52 of the drive chassis 24 after use of the autoinjector 10, with the first and second parts 50, 52 of the drive chassis 24 being distinguishable from one another.

50. The autoinjector 10 according to one of embodiments 1 to 49, further comprising a drive chassis 24, the drive chassis 24 comprising a dispensing limb 22 and a trigger limb 32, wherein a plunger 26 is arrangeable at a proximal end of the dispensing limb 22 and a trigger arm 36 is arranged extending proximally from the trigger limb 32.

51. The autoinjector 10 according to embodiment 50, wherein the trigger limb 32 and the dispensing limb 22 are arranged in parallel to one another respectively at least essentially in parallel to one another and are connected to one another at a respective distal end side of the dispensing limb 22 and the trigger limb 32 via a web 42.

52. An autoinjector 10, optionally in accordance with one of embodiments 1 to 51, the autoinjector 10 comprising: a housing 12, a pre-filled syringe 16 mounted in the housing 12, a drive chassis 24 mounted in the housing 12, the drive chassis 24 being biased with respect to the housing 12, the drive chassis 24 further being fixed with respect to the housing 12 and for a movement relative to the housing 12 in a storage state of the autoinjector 10, the drive chassis 24 moving relative to the housing 12 on dispensing a material from the pre-filled syringe 16, and wherein the autoinjector 10 comprises an audible feedback member 58 is configured to generate an audible end of dose feedback between the drive chassis 24 and the housing 12 once the material has been dispensed from the autoinjector 10.

53. The autoinjector 10 according to one or more of the preceding embodiments, wherein drive chassis 24 comprises a first part 56 of the audible feedback member 58 that engages a second part 66 of the audible feedback member 58 arranged at the housing 12 to generate the audible end of dose feedback.

54. The autoinjector 10 according to one or more of the preceding embodiments, wherein the housing 12 comprises a recess 208 and the drive chassis 24 engages the recess 208 to generate the audible end of dose feedback.

55. The autoinjector 10 according to embodiment 53 and embodiment 54, wherein the first part 56 of the audible feedback member 58 of the drive chassis 24 engages the recess 208 to generate the audible end of dose feedback.

56. The autoinjector 10 according to one or more of the preceding embodiments, wherein the housing 12 comprises a chamfered distal inner housing end 204 on an inner surface 132 thereof.

57. The autoinjector 10 according to embodiment 56, wherein the chamfered distal inner housing end 204 deflects a part of the drive chassis 24 radially inwardly as this moves from the storage state to an end of dose state.

58. The autoinjector 10 according to embodiment 57 and one of embodiments 53 to 56, wherein the chamfered distal inner housing end 204 deflects the first part 56 of the audible feedback member 58 radially inwardly as the drive chassis 24 moves from the storage state to an end of dose state.

59. The autoinjector 10 according to embodiment 58, wherein the chamfered distal inner housing end 204 is configured to deflect the first part 56 of the audible feedback member 58 radially inwardly before the first part 56 of the audible feedback member 58 engages the recess 208.

60. The autoinjector 10 according to one or more of the preceding embodiments, wherein the audible end of dose feedback comprises an audible click.

61. The autoinjector 10 according to embodiment 60, wherein the audible click is brought about by at least one of a contact between two components 56, 66 and an acceleration of a component 56.

62. The autoinjector 10 according to embodiment 60 or embodiment 61 and one of embodiments 57 to 59, wherein the audible click is generated by a radially outwardly directed relaxation of the radially inwardly deflected part 56 of the drive chassis 24.

63. The autoinjector 10 according to one or more of the preceding embodiments, wherein the drive chassis 24 further comprises a plunger support 44 for engaging a plunger 26 of the pre-filled syringe 16.

64. The autoinjector 10 according to embodiment 63 and one of embodiments 55 to 62, wherein the first part 56 of the audible feedback member 58 extends from the drive chassis at a part of the drive chassis 24 different from the plunger support 44.

65. The autoinjector 10 according to one or more of the preceding embodiments further comprising a drive spring 74 mounted between the drive chassis 24 and the housing 12.

66. The autoinjector 10 according to embodiment 65 and one of embodiments 63 and 64, wherein a relaxation of the drive spring 74 drives the plunger support 44 towards the plunger 26 of the pre-filled syringe 16 after activation of the autoinjector 10.

67. The autoinjector 10 according to embodiment 66, wherein the drive spring 74 is arranged within a part of the drive chassis 24 comprising the first part 56 of the audible feedback member 58, in particular in a passage 140.

68. The autoinjector 10 according to one or more of the preceding embodiments, wherein the housing 12 is a two-part housing comprising an inner body 80 and an outer body 82.

69. The autoinjector 10 according to embodiment 68, wherein the inner body 80 and the outer body 82 are fixed in position relative to one another.

70. The autoinjector 10 according to embodiment 68 or embodiment 69, wherein the inner body 80 and the outer body 82 are connected to one another via a connection 72.

71. The autoinjector 10 according to embodiment 70, wherein the connection 72 is formed by a nose 188 engaging a window 190.

72. The autoinjector 10 according to embodiment 71, wherein the nose 188 is formed at the inner body 80 and engages the window 190 formed at the outer body 82.

73. The autoinjector 10 according to embodiment 68 and one of embodiments 54 to 72, wherein the inner body 80 comprises the recess 208.

74. The autoinjector 10 according to one or more of the preceding embodiments, wherein the inner body 80 comprises one or more cut-outs 174, 176 and/or holes 168 that are configured to cooperate with one or more corresponding parts 184, 186, 166 of the needle guard 18.

75. The autoinjector 10 according to one or more of the embodiments 68 to 74 and one or more of the embodiments 54 to 66, wherein the drive spring 74 is arranged between the outer body 82 and the drive chassis 24.

76. The autoinjector 10 according to one or more of the preceding embodiments, wherein the drive chassis 24 is of generally U-shaped design and comprises a dispensing limb 22 as well as a trigger limb 32.

77. The autoinjector 10 according to one or more of the preceding embodiments, wherein the drive chassis 24, the first part 56 of the audible feedback member 58 and the plunger support 44 are formed in one piece from the same material.

78. An autoinjector 10, optionally in accordance with one or more of the preceding embodiments, the autoinjector 10 comprising: a housing 12 in which a pre-filled syringe 16 is arranged, a drive chassis 24 mounted in the housing 12, the drive chassis 24 being biased with respect to the housing 12 by a drive spring 74, the drive chassis 24 further being fixed with respect to the housing 12 and a movement relative to the housing 12 in a storage state of the autoinjector, the drive chassis 24 comprising a trigger arm 36 engaging a stop feature 54 present in the housing 12 in the storage state of the autoinjector 10 for fixing the drive chassis 24 with respect to the housing 12, and wherein the trigger arm 36 is configured to be disengaged from the stop feature 54 on activation of the autoinjector 10.

79. The autoinjector 10 according to one or more of the preceding embodiments, wherein the stop feature 54 comprises an opening 138.

80. The autoinjector 10 according to one or more of the preceding embodiments, wherein the stop feature 54 comprises a convex surface 152.

81. The autoinjector 10 according to embodiment 80, wherein the trigger arm 36 is configured to cooperate with the convex surface 152 of the stop feature 54.

82. The autoinjector 10 according to one or more of the preceding embodiments, wherein the trigger arm 36 comprises a projection 154 engaging the stop feature 54.

83. The autoinjector 10 according to embodiment 82, wherein the projection 154 is configured to cooperate with the opening 138.

84. The autoinjector 10 according to one of embodiments 82 or embodiment 83, wherein the projection 156 is configured to cooperate with the convex surface 152.

85. The autoinjector 10 according to one or more of the preceding embodiments, wherein the trigger arm 36 comprises a web 148 projecting therefrom.

86. The autoinjector 10 according to embodiment 85 and embodiment 84 or embodiment 83, wherein the web 148 is arranged at a surface different from a surface at which the projection 154 is arranged.

87. The autoinjector 10 according to one or more of the preceding embodiments, further comprising a needle guard 18, wherein an axial movement of the needle guard 18 towards the drive chassis 24 releases the fixing of the drive chassis 24 with respect to the housing 12.

88. The autoinjector 10 according to embodiment 87, wherein the needle guard 18 comprises a blocking rib 144.

89. The autoinjector 10 according to embodiment 87 or embodiment 88, wherein the needle guard 18 engages the trigger arm 36 on axially moving toward the drive chassis 24.

90. The autoinjector 10 according to one of embodiments 87 to 89 and embodiment 85, wherein the needle guard 18 comprises an engagement surface 146 configured to engage the web 148 of the trigger arm 36.

91. The autoinjector 10 according to embodiment 88 or embodiment 89 and embodiment 90, wherein the engagement surface 146 projects from the rib.

92. The autoinjector 10 according to one of embodiments 80 to 86, wherein the web 148 comprises a deflection surface 150 inclined with respect to a movement direction of the drive chassis 24.

93. The autoinjector 10 according to one of embodiments 85 to 87, wherein the engagement surface 146 is inclined with respect to a movement direction of the drive chassis 24.

94. The autoinjector 10 according to embodiment 92 and embodiment 93, wherein the engagement surface 146 and the deflection surface 150 are inclined with respect to a movement direction of the drive chassis 24 in a cooperating manner.

95. The autoinjector 10 according to one of embodiments 78 to 94, wherein the drive spring 74 is configured to drive the drive chassis 24 towards the needle guard 18 after activation of the autoinjector 10.

96. The autoinjector 10 according to one or more of the preceding embodiments, wherein the drive chassis 24 further comprises a plunger support 44 for engaging a piston of the pre-filled syringe 16.

97. The autoinjector according to embodiment 96, wherein a relaxation of the drive spring 74 drives the plunger support 44 towards the plunger 26 of the pre-filled syringe 16.

98. The autoinjector according to one of the preceding embodiments, wherein the drive chassis 24 is of generally U-shaped design.

99. The autoinjector according to one or more of the preceding embodiments, wherein the trigger arm 36, the drive chassis 24 and the plunger support 44 are formed in one piece from the same material.

100. An autoinjector 10, optionally in accordance with one or more of the preceding embodiments, the autoinjector 10 comprising a pre-filled syringe 16 arranged within a housing 12 of the autoinjector 10, a needle shield 78 covering a needle 34 of the pre-filled syringe 16 in a storage state of the autoinjector 10, an axially moveable needle guard 18 arranged to cover the needle 34 of the pre-filled syringe 16 at least after use of the autoinjector 10 and to move relative to the pre-filled syringe 16 during use of the autoinjector 10, as well as a removable cap 70 in which the needle guard 18 is stored in the storage state of the autoinjector 10, wherein the cap 70 is removably connected to the needle guard 18 in the storage state of the autoinjector 10, and wherein, on removal of the cap 70, the needle shield 78 is also removed from the autoinjector 10.

101. The autoinjector according to one or more of the preceding embodiments, wherein the needle guard 18 is connected to the cap 70 via one or more snap fit connections 94.

102. The autoinjector according to embodiment 101, wherein each snap fit connection 94 comprises a snap-fit projection 96 cooperating with a corresponding snap-fit area 98.

103. The autoinjector according to embodiment 102, wherein one or more snap-fit projections 96 are provided at an outer surface 126 of the needle guard 18.

104. The autoinjector according to embodiment 101 or embodiment 102, wherein one or more snap-fit areas 98 are provided at an inner surface of the cap 70.

105. The autoinjector according to one or more of the preceding embodiments, wherein an outer wall 116 of the cap 70 contacts an outer wall 136 of the housing 12 in a storage state of the autoinjector 10.

106. The autoinjector according to embodiment 105, wherein the outer wall 116 of the cap 70 and the outer wall 136 of the housing 12 do not overlap in an axial direction of the 107. The autoinjector according to embodiment 105 or embodiment 106, wherein the outer wall 116 of the cap 70 and the outer wall 136 of the housing 12 radially overlap in the storage state of the autoinjector 10.

108. The autoinjector according to one or more of the preceding embodiments, wherein the cap 70 prevents axial movement of the needle guard 18 when attached to the needle guard 18 in the storage state.

109. The autoinjector according to one or more of the preceding embodiments, wherein the needle shield 78 is arranged within an inner wall of the cap 70 in the storage state of the autoinjector 10.

110. The autoinjector according to one or more of the preceding embodiments, wherein a front end of the needle guard 18 is arranged within an opening 124 of the cap 70.

111. The autoinjector according to one or more of the preceding embodiments, wherein a front end 122 of the needle guard 18 is arranged within an opening 124 of the cap 70 and wherein the opening 124 is formed between the outer wall 116 of the cap 70 and the inner wall of the cap 70.

112. The autoinjector according to one or more of the preceding embodiments, wherein a front end 122 of the needle guard 18 is arranged within an opening 124 of the cap 70 and wherein the front end 122 of the needle guard 18 comprises the one or more snap-fit projections 96.

113. The autoinjector according to one or more of the preceding embodiments, wherein an inner surface 128, 132 of the housing 12 comprises one or more grooves 130, 134 in which one or more of the snap-fit projections 96 can axially move relative to the housing 12 on a movement of the needle guard 18.

114. The autoinjector according to one or more of the preceding embodiments, wherein the axially moveable needle guard 18 is arranged to move relative to the housing 12 during use of the autoinjector 10.

115. The autoinjector according to one or more of the preceding embodiments, wherein the cap 70 is of single piece design.

116. The autoinjector according to one or more of the preceding embodiments, wherein the cap 70 comprises inwardly facing projections 108 at a needle guard facing end 102 that engage a syringe facing surface 110 of the needle shield 78.

117. The autoinjector according to one or more of the preceding embodiments, wherein the inner wall 106 of the cap 70 comprises two windows 112.

118. The autoinjector 10 according to embodiment 116 and embodiment 117, wherein each projection 108 is arranged at a window 112.

119. The autoinjector 10 according to one or more of the preceding embodiments, wherein recesses 114 are formed in the inner wall of the cap 70.

120. The autoinjector 10 according to one or more of the preceding embodiments, wherein an inner surface 118 of the outer wall 116 of the cap 70 comprises one or more ribs 120.

121. The autoinjector 10 according to one or more of the preceding embodiments, wherein the cap 70 comprises a stand of the autoinjector 10.

122. The autoinjector 10 according to one or more of the preceding embodiments, wherein an axial movement of the needle guard 18 in the direction of the pre-filled syringe 16 brings about an engagement of the release mechanism 40 of a plunger 26 of the pre-filled syringe 16 for dispensing a material stored in the pre-filled syringe 16.

123. An autoinjector 10, optionally according to one or more of the preceding embodiments, the autoinjector 10 comprising: a housing 12 in which a pre-filled syringe 16 is arranged, a drive chassis 24 mounted in the housing 12, the drive chassis 24 being biased with respect to the housing 12 and being fixed with respect to the housing 12 in a storage state of the autoinjector 10, a status indicator window 20 arranged at the housing 12 via which the drive chassis 24 is visible from the outside, with the status indicator window 20 showing a first part 50 of the drive chassis 24 in the storage state of the autoinjector 10 and a second part 52 of the drive chassis 24 after use of the autoinjector 10, with the first and second parts 50, 52 of the drive chassis 24 being distinguishable from one another.

124. The autoinjector 10 according to embodiment 123, wherein the status indicator window 20 is formed by an elongate slot extending radially around a part of the housing 12.

125. The autoinjector 10 according to embodiment 123 or embodiment 124, wherein the first and second parts 50, 52 of the drive chassis 24 are distinguishable from one another due to a difference in color, a printed label applied at a surface of the drive chassis 24, a text applied on the surface 49 of the drive chassis 24 and/or an icon displayed in the surface of the drive chassis 24.

126. The autoinjector 10 according to according to one or more of the preceding embodiments, further comprising a syringe window 14 via which the pre-filled syringe 16 is visible from the outside.

127. The autoinjector 10 according to embodiment 126, wherein the syringe window 14 shows a content filled in the pre-filled syringe 16 in the storage state of the autoinjector 10.

128. The autoinjector 10 according to embodiment 126 or embodiment 127, wherein the syringe window 14 shows at least one of a plunger 26 arranged within the pre-filled syringe 16 and a part of the dispensing limb 22 in the pre-filled syringe 16 after use of the autoinjector 10.

129. The autoinjector 10 according to one of embodiments 126 to 128, wherein the syringe window 14 is arranged in the housing 12.

130. The autoinjector 10 according to one of embodiments 126 to 129, wherein the syringe window 14 is of elongate shape and a length of the elongate shape extends in an axial direction of the autoinjector 10.

131. The autoinjector 10 according to one of embodiments 126 to 130, wherein the syringe window is arranged transverse to the status indicator window 20.

132. The autoinjector 10 according to one of embodiments 126 to 131, wherein the syringe window shows a different part of the drive chassis 24 in comparison with the status indicator window 20.

133. The autoinjector 10 according to one or more of the preceding embodiments, wherein the drive chassis 24 comprises a trigger arm 36 engaging an opening 138 in the housing 12 in the storage state of the autoinjector 10.

134. The autoinjector 10 according to one or more of the preceding embodiments, further comprising a needle guard 18, wherein an axial movement of the needle guard 18 towards the drive chassis 24 releases the fixing of the drive chassis 24 with respect to the housing 12.

135. The autoinjector 10 according to embodiment 134, wherein the needle guard 18 comprises a plunger arm 142.

136. The autoinjector 10 according to embodiment 134 or embodiment 135, wherein the needle guard 18 engages the trigger arm 36 on axially moving toward the drive chassis 24.

137. The autoinjector 10 according to embodiment 135 or embodiment 136, wherein the plunger arm 142 of the needle guard 18 engages the trigger arm 36 on axially moving toward the drive chassis 24.

138. The autoinjector 10 according to one or more of the preceding embodiments, further comprising a drive spring 74 mounted between an end of the housing 12 and the drive chassis 24.

139. The autoinjector 10 according to embodiment 140, wherein the spring is configured to drive the drive chassis 24 towards the needle guard 18 after activation of the autoinjector 10.

140. The autoinjector 10 according to one or more of the preceding embodiments, wherein the drive chassis 24 further comprises a plunger support 44 for engaging a piston of the pre-filled syringe 16.

141. The autoinjector 10 according to embodiment 138 or embodiment 139 and embodiment 140, wherein the relaxation of the drive spring 74 drives the plunger support 44 towards the piston of the pre-filled syringe 16.

142. The autoinjector 10 according to one or more of the preceding embodiments, wherein the drive chassis 24 is of generally U-shaped design.

143. The autoinjector 10 according to one or more of the preceding embodiments, wherein the trigger arm 36, the drive chassis 24 and the plunger support 44 are formed in one piece from the same material.

144. An autoinjector 10, optionally according to one or more of the preceding embodiments, comprising a drive chassis 24, the drive chassis 24 comprising a dispensing limb 22 and a trigger limb 32, wherein a plunger 26 is arranged at a proximal end of the dispensing limb 22 and a trigger arm 36 is arranged extending proximally from the trigger limb 32, wherein the trigger limb 32 and the dispensing limb 22 are arranged in parallel to one another respectively at least essentially in parallel to one another and are connected to one another at a respective distal side of the dispensing limb 22 and the trigger limb 32.

145. An autoinjector 10 according to embodiment 144, wherein the trigger limb 32, the dispensing limb 22, the plunger support 44 and the trigger arm 36 are integrally formed in one piece.

146. An autoinjector 10 according to embodiment 144 or embodiment 145, wherein the trigger arm 36 is biased with respect to a housing 12 of the autoinjector 10 in a storage state of the autoinjector 10.

147. The autoinjector 10 according to one or more of the preceding embodiments, wherein the trigger arm 36 is deflected on moving the autoinjector 10 from a storage state into an activated state of the autoinjector 10.

148. The autoinjector 10 according to one or more of the preceding embodiments, wherein the trigger arm 36 is actuated on by a needle guard 18 of the autoinjector 10 on moving the autoinjector 10 from a storage state into an activated state of the autoinjector 10.

149. The autoinjector 10 according to one or more of the preceding embodiments, wherein the plunger support 44 is configured to act on a pre-filled syringe 16 of the autoinjector 10.

150. The autoinjector 10 according to one or more of the preceding embodiments, further comprising a drive spring 74.

151. The autoinjector 10 according to embodiment 150, wherein the drive spring 74 is arranged within a housing 12 of the autoinjector 10 between a distal housing wall 84 and the drive chassis 24.

152. The autoinjector 10 according to embodiment 151, wherein the drive spring 74 biases the trigger arm 36 in a storage state of the autoinjector 10 with respect to the housing 12 of the autoinjector 10.

153. The autoinjector 10 according to one of embodiments 150 to 152, wherein the drive spring 74 is configured to drive the plunger 26 of the autoinjector 10 in a pre-filled syringe 16 of the autoinjector 10.

154. The autoinjector 10 according to one or more of the preceding embodiments, wherein the drive chassis 24 is linearly guided within a housing 12 of the autoinjector 10 on moving the autoinjector 10 from a storage state into an activated state of the autoinjector 10.

155. The autoinjector 10 according to one or more of the preceding embodiments, wherein the trigger arm 36 is configured to move radially and transversely with respect to the trigger limb 32.

156. The autoinjector 10 according to one or more of the preceding embodiments, wherein the trigger arm 36 is configured to cooperate with a stop feature 54 arranged at the housing 12 in a storage state of the autoinjector 10.

157. The autoinjector 10 according to one or more of the preceding embodiments, wherein the trigger limb 32 and the dispensing limb 22 are arranged in an at least generally U-shaped manner respectively in a U-shaped manner.

158. The autoinjector 10 according to one or more of the preceding embodiments, wherein the trigger limb 32 further comprises at least a first part 56 of an audible end of dose feedback member 58.

159. The autoinjector 10 according to embodiment 157, further comprising a housing 12, wherein the housing 12 further comprises at least one second part 66 of the audible end of dose feedback member 58, optionally wherein the housing 12 is formed by an outer body 82 and an inner body 80 and one of the inner body 80 and the outer body 82 comprises the at least one second part 66 of the audible end of dose feedback member 58.

160. The autoinjector 10 according to embodiment 157 or embodiment 158, wherein the first and second parts 56, 66 of the audible end of dose feedback members 58 are formed by a recess 208 and a latching tongue 62 configured to cooperate with the recess 208.

161. The autoinjector 10 according to one of embodiments 158 to 160, wherein the audible end of dose feedback member 58 is configured to emit a sound once the material has been dispensed from the autoinjector 10.

162. The autoinjector 10 according to one of embodiments 158 to 161, wherein the audible end of dose feedback member 58 is configured to emit a sound between the drive chassis 24 and the housing 12 once the material has been dispensed from the autoinjector 10.

163. The autoinjector 10 according to one or more of the preceding embodiments, wherein the inner body 80 further comprises a first cut-out 174, with the first cut-out 74 being configured to cooperate with a clip arm 184 and a lock-out arm 186 of the needle guard 18.

164. The autoinjector 10 according to embodiment 163, wherein the inner body 80 further comprises a second cut-out 176, with the second cut-out being configured to cooperate with the lock-out arm 186 of the needle guard 18.

165. The autoinjector 10 according to one or more of the preceding embodiments, wherein the drive chassis 24 further comprises a second trigger arm 36.

166. The autoinjector 10 according to embodiment 165, wherein the second trigger arm 36 is arranged at a side of the drive chassis 24 disposed opposite to the first trigger arm 36.

167. The autoinjector 10 according to one or more of the preceding embodiments, wherein the trigger limb 32 comprises a passage 140 formed therein.

168. The autoinjector 10 according to embodiment 167, wherein the passage 140 is configured to receive at least a part of the drive spring 74.

169. The autoinjector 10 according to one or more of the preceding embodiments, wherein the trigger limb 32 comprises a lip 216 at an end disposed opposite to the web 42.

170. The autoinjector 10 according to embodiment 169, wherein the lip 216 is configured to engage clip arms 184 formed at the needle guard 18.

171. The autoinjector 10 according to embodiment 169 or embodiment 170, wherein the lip 216 comprises two tips 218, with each tip 218 being configured to engage a respective one of a clip arm 184 formed at the needle guard 18.

172. The autoinjector 10 according to one or more of the preceding embodiments, wherein the needle shield 78 comprises a needle receptacle 212 configured to receive the needle 34 of the pre-filled syringe 16.

173. The autoinjector 10 according to one or more of the preceding embodiments, wherein the cap 70 comprises a needle shield holder 104 that is configured to receive the needle shield 78.

174. The autoinjector 10 according to one or more of the preceding embodiments, wherein the needle guard 18 further comprises one or more lock-out arms 186.

175. The autoinjector 10 according to embodiment 174, wherein the one or more lock-out arms 186 are configured to cooperate with the inner body 80.

176. The autoinjector 10 according to embodiment 174 or embodiment 175, wherein the one or more lock-out arms 186 are configured to engage one or more bars 178 of the inner body 80 in the lock-out state.

177. The autoinjector 10 according to one of embodiments 174 to 176, wherein the one or more lock-out arms 186 are configured to engage a respective one of one or more cut-outs 176 of the inner body 80 in the lock-out state.

178 The autoinjector 10 according to one of embodiments 174 to 177, wherein the one or more lock-out arms 186 are configured to engage one or more further cut-outs 174 of the inner body 80 in the dispensing state and in the storage state.

179. The autoinjector 10 according to one or more of the preceding embodiments, wherein the needle guard 18 further comprises one or more clip arms 184.

180. The autoinjector 10 according to embodiment 179, wherein the one or more clip arms 184 are configured to cooperate with a respective one of one or more cut-outs 174 of the inner body 80 in the dispensing state.

181. The autoinjector 10 according to embodiment 179 or embodiment 180, wherein the one or more clip arms 184 are deflected inwardly and abut an inner surface 132 of the inner body 80 in the lock-out state.

182. The autoinjector 10 according to one of embodiments 179 to 181, wherein the one or more clip arms 184 are configured to be deflected inwardly by the drive chassis 24 on a proximal movement of the drive chassis 24.

183. The autoinjector 10 according to one or more of the preceding embodiments, wherein the needle guard 18 further comprises a plunger arm 142.

184. The autoinjector 10 according to embodiment 183, wherein the plunger arm 142 comprises one or more blocking ribs 144 arranged at a distal end thereof.

185. The autoinjector 10 according to embodiment 184, wherein the plunger arm 142 comprises two blocking ribs 144, with the two blocking ribs 144 being arranged oppositely disposed to one another.

186. The autoinjector 10 according to embodiment 184 or embodiment 185, wherein the one or more blocking ribs 144 are configured to block a radial movement of the trigger arm 36 in the storage state.

187. The autoinjector 10 according to one of embodiments 185 to 186, wherein the plunger arm 142 comprises one or more cams 162.

188. The autoinjector 10 according to embodiment 187, wherein the one or more cams 162 are configured to engage the one or more trigger arms 36 of the drive chassis 24 on activation of the autoinjector 10.

189. The autoinjector 10 according to embodiment 188, wherein the one or more cams 162 are configured to entrain the one or more trigger arms 36 of the drive chassis 24 in the transverse direction T on activation of the autoinjector 10.

190. The autoinjector 10 according to one or more of the preceding embodiments, wherein the needle guard 18 comprises one or more protrusions 166 cooperating with a respective one of one or more elongate holes 168 present in the inner body 80.

191. The autoinjector 10 according to embodiment 190, wherein the one or more protrusions 166 are provided to ensure a linear guidance of the needle guard 18 relative to the inner body 80.

192. The autoinjector 10 according to one or more of the preceding embodiments, wherein the needle guard 18 further comprises one or more anti-pull off features 170.

193. The autoinjector 10 according to embodiment 192, wherein the one or more anti-pull off features 170 are configured to prevent a removal of the needle guard 18 from the proximal end of the housing 12.

194. The autoinjector 10 according to embodiment 194, wherein the inner body 80 comprises one or more elongate holes 168 each having a proximal stop 172, wherein the proximal stop 172 prevents a respective one of the protrusions 166 from being moved proximally beyond the stop 172.

195. The autoinjector 10 according to one or more of the preceding embodiments, wherein the inner body 80 of the housing 12 further comprises at least a part 66 of an audible end of dose feedback member 58.

196. The autoinjector 10 according to embodiment 195, wherein the part 66 of the audible end of dose feedback member 58 comprises an inner body recess 206 having a distal surface 196 and a proximal surface 198 surrounding the inner body recess 206.

197. The autoinjector 10 according to one or more of the preceding embodiments, wherein the inner body 80 comprises one or more cut-outs 174, 176.

198. The autoinjector 10 according to embodiment 197 and embodiment 195 or 196, wherein the one or more cut-outs 174, 176 are arranged at an end of the inner body 80 disposed opposite to the second part 66 of the audible end of dose feedback member 58.

199. The autoinjector 10 according to one or more of the preceding embodiments, wherein the outer body 82 comprises one or more stop features 54.

200. The autoinjector 10 according to embodiment 199, wherein each stop feature 54 is provided at a respective opening 138.

201. The autoinjector 10 according to embodiment 199 or embodiment 200, wherein the respective stop feature 54 is a component of a respective release mechanism 40 of the autoinjector 10.

202. The autoinjector 10 according to one or more of the preceding embodiments, wherein an outer surface 49 of the trigger limb 32 comprises a first and a second part outer surface 50, 52 whose appearance differ from one another.

204. The autoinjector 10 according to one or more of the preceding embodiments, wherein a block 184' of the clip arm 184 is arranged between a lock-out surface 234 and an extended abutment surface in the lock-out state of the autoinjector 10.

204. The autoinjector 10 according to one or more of the preceding embodiments, wherein a block 184' of the clip arm 184 is arranged moveable within an aperture 174' of the inner body 80.

205. The autoinjector 10 according to one or more of the preceding embodiments, wherein a block 184' of the clip arm 184 is arranged moveable within a long limb 238 and a short limb 236 of an aperture 174' of the inner body 80.

206. The autoinjector 10 according to one or more of the preceding embodiments, wherein a respective trigger arm 36 is configured to engage a respective one of the clip arms 184 for locking the needle guard in the lock-out state.

207. The autoinjector 10 according to one or more of the preceding embodiments, wherein an axial height of the cut-out defines a movement range along the axial direction A of the needle guard 18.

While only selected embodiments have been chosen to illustrate the present invention, it will be apparent to those skilled in the art from this disclosure that various changes and modifications can be made herein without departing from the scope of the invention as defined in the appended claims. For example, unless specifically stated otherwise, the size, shape, location or orientation of the various components can be changed as needed and/or desired so long as the changes do not substantially affect their intended function. Unless specifically stated otherwise, components that are shown directly connected or contacting each other can have intermediate structures disposed between them so long as the changes do not substantially affect their intended function. The functions of one element can be performed by two, and vice versa unless specifically stated otherwise. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

The invention claimed is:

1. An autoinjector comprising:
a housing;
a pre-filled syringe mounted in the housing and fixed relative to the housing during insertion, injection and retraction of a needle;
a drive chassis comprising a dispensing limb axially movable in the housing to move a plunger in the pre-filled syringe to dispense the medicament via the needle of the pre-filled syringe;
a drive spring arranged within the housing and configured to drive a plunger support of the drive chassis into the pre-filled syringe;
a needle guard axially moveable in the housing for movement between a storage state surrounding the needle of the pre-filled syringe, a dispensing state exposing the needle, and a lock-out state surrounding the needle; and
a lock-out spring arranged between the needle guard and the housing, the needle guard being configured to compress the lock-out spring on moving from the storage state to the dispensing state, and the needle guard being configured to be moved by a relaxation of the lock-out spring from the dispensing state to the lock-out state,
the needle guard including at least one arm having an abutment surface configured to engage a first stop surface of the housing to establish a frontmost position of the needle guard with respect to the housing in the storage state, and configured to engage a second stop surface of the housing to establish an offset position of the needle guard with respect to the housing in the lock-out state, the offset position is axially offset with respect to the housing from the frontmost position of the needle guard in a more distal direction.

2. The autoinjector according to claim 1, wherein the needle guard includes a pair of the arms that each has the abutment surface, and the housing includes a pair of the first stop surfaces and a pair of the second stop surfaces.

3. The autoinjector according to claim 2, wherein the first stop surfaces are formed by at least one cut-out in the housing.

4. The autoinjector according to claim 1, wherein the needle guard is configured to engage the drive chassis and releases an engagement of the drive chassis with the housing upon an axial movement of the needle guard towards the dispensing state.

5. The autoinjector according to claim 1, wherein the pre-filled syringe has a proximal end and a distal end, the proximal end is not axially supported from moving towards a proximal end of the housing, and the distal end is axially supported to prevent movement towards the proximal end of the housing.

6. The autoinjector according to claim 1, wherein the housing comprises a first body and a second body which are fixed together.

7. The autoinjector according to claim 6, wherein the first body is an inner body and the second body is an outer body, and the outer body is at least partly arranged to overlap with the inner body.

8. The autoinjector according to claim 1, wherein the needle guard is non-rotatable with respect to the housing.

9. The autoinjector according to claim 1, further comprising
a removable needle shield removably attached to the pre-filled syringe.

10. The autoinjector according to claim 1, wherein the housing includes a stop feature that is engaged with the drive chassis when the needle guard is in the storage state.

11. The autoinjector according to claim 10, further comprising
a release mechanism comprising at least one trigger arm provided to the drive chassis, the at least one trigger arm cooperating with the stop feature arranged at the housing; and
a plunger arm provided to the needle guard being configured to cause deflection of the at least one trigger arm upon a distal axial movement of the needle guard.

12. The autoinjector according to claim 11, wherein the needle guard includes at least one plunger arm that is configured to engage the trigger arm so as to cause the trigger arm to move relative to the stop feature to release the drive chassis for movement relative to the housing.

13. The autoinjector according to claim 1, wherein the housing includes a least one cut-out having a first limb and a second limb, the first stop surface of the housing is formed by an end of the second limb, and the second stop surface of the housing is formed by an end of the first limb.

14. The autoinjector according to claim 13, wherein the first stop surface of the housing and the second stop surface of the housing form a step between the second limb and the first limb.

* * * * *